US009493755B2

(12) United States Patent
Guo et al.

(10) Patent No.: US 9,493,755 B2
(45) Date of Patent: Nov. 15, 2016

(54) BACILLUS, HYALURONIDASE, AND USES THEREOF

(71) Applicant: BLOOMAGE FREDA BIOPHARM CO., LTD., Jinan, Shandong (CN)

(72) Inventors: Xueping Guo, Jinan (CN); Yanli Shi, Jinan (CN); Liping Qiao, Jinan (CN); Ning Feng, Jinan (CN); Guanfeng Wang, Jinan (CN); Haina Li, Jinan (CN); Wei Xue, Jinan (CN); Haiying Wang, Jinan (CN); Yihong Luan, Jinan (CN); Aihua Liu, Jinan (CN)

(73) Assignee: BLOOMAGE FREDA BIOPHARM CO., LTD., Jinan (CN)

( * ) Notice: Subject to any disclaimer, the term of this patent is extended or adjusted under 35 U.S.C. 154(b) by 0 days.

(21) Appl. No.: 14/379,862

(22) PCT Filed: Nov. 29, 2012

(86) PCT No.: PCT/CN2012/085503
§ 371 (c)(1),
(2) Date: Aug. 20, 2014

(87) PCT Pub. No.: WO2013/123791
PCT Pub. Date: Aug. 29, 2013

(65) Prior Publication Data
US 2015/0175991 A1 Jun. 25, 2015

(30) Foreign Application Priority Data

Feb. 21, 2012 (CN) .......................... 2012 1 0039111
Apr. 13, 2012 (CN) .......................... 2012 1 0108194

(51) Int. Cl.
| | |
|---|---|
| A61K 8/66 | (2006.01) |
| C12N 9/26 | (2006.01) |
| C12R 1/07 | (2006.01) |
| A61K 8/73 | (2006.01) |
| A61Q 19/00 | (2006.01) |
| C12P 19/26 | (2006.01) |
| A61Q 17/04 | (2006.01) |
| A61Q 19/08 | (2006.01) |
| A23L 1/305 | (2006.01) |
| A61K 31/728 | (2006.01) |
| A61Q 19/02 | (2006.01) |
| C08B 37/08 | (2006.01) |
| C12P 19/28 | (2006.01) |

(52) U.S. Cl.
CPC ............ *C12N 9/2474* (2013.01); *A23L 1/305* (2013.01); *A61K 8/66* (2013.01); *A61K 8/735* (2013.01); *A61K 31/728* (2013.01); *A61Q 17/04* (2013.01); *A61Q 19/00* (2013.01); *A61Q 19/004* (2013.01); *A61Q 19/02* (2013.01); *A61Q 19/08* (2013.01); *C08B 37/0072* (2013.01); *C12N 9/2408* (2013.01); *C12P 19/26* (2013.01); *C12P 19/28* (2013.01); *C12R 1/07* (2013.01); *A23V 2002/00* (2013.01); *Y02P 20/52* (2015.11)

(58) Field of Classification Search
None
See application file for complete search history.

(56) References Cited

U.S. PATENT DOCUMENTS

| 6,689,349 B1 | 2/2004 | Wohlrab et al. |
| 2003/0104533 A1 | 6/2003 | Weigel et al. |
| 2005/0221446 A1 | 10/2005 | Widner et al. |
| 2007/0202570 A1 | 8/2007 | Kamei |
| 2008/0038780 A1 | 2/2008 | Stocks et al. |
| 2011/0130339 A1 | 6/2011 | Kim et al. |

FOREIGN PATENT DOCUMENTS

| CN | 1304317 A | 7/2001 |
| CN | 1563108 A | 1/2005 |
| CN | 101384724 A | 3/2009 |
| CN | 101426925 A | 5/2009 |
| CN | 101507733 A | 8/2009 |
| CN | 101942037 A | 1/2011 |
| CN | 102304193 A | 1/2012 |
| CN | 102559559 A | 7/2012 |
| EP | 1826274 A1 | 8/2007 |
| EP | 1992645 A1 | 11/2008 |
| JP | 2002-533376 A | 10/2002 |
| JP | 2007-254725 A | 10/2007 |
| JP | 2009-541372 A | 11/2009 |

(Continued)

OTHER PUBLICATIONS

Kreil (Protein Science, 4:1666-1669, 1995).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bai et al., "Research Progress of Preparation and Application of Hyaluronic Acid," Guangdong Chemical Industry, vol. 37, No. 11, Dec. 31, 2010, pp. 243-244, 248, with an English language abstract.

(Continued)

*Primary Examiner* — Brian J Gangle
(74) *Attorney, Agent, or Firm* — Birch, Stewart, Kolasch & Birch, LLP

(57) ABSTRACT

The present invention provides a *bacillus* sp. having a deposit access number of CGMCC NO. 5744 and a hyaluronidase produced by the *bacillus* and the amino acid sequence of the hyaluronidase is shown in SEQ ID NO: 2. The present invention further relates to a process for preparing oligomeric hyaluronic acid or salts thereof or low-molecular-weight hyaluronic acid or salts thereof by using the *bacillus* or the hyaluronidase produced thereby. The produced oligomeric hyaluronates or low-molecular-weight hyaluronates have advantages such as good transdermal absorption ability, high purity, no cytotoxicity, potent antioxidant ability. The present invention also provides use of the *bacillus* having a deposit access number of CGMCC NO. 5744, or the hyaluronidase, oligomeric hyaluronates or salts thereof, low-molecular-weight hyaluronates or salts thereof produced by the *bacillus* in the fields of osmetics, food products and medicines.

23 Claims, 11 Drawing Sheets

(56) References Cited

FOREIGN PATENT DOCUMENTS

| WO | WO 00/38647 A1 | 7/2000 |
| WO | WO 2007/099830 A1 | 9/2007 |
| WO | WO 2008/000260 A1 | 1/2008 |

OTHER PUBLICATIONS

International Search Report (Form PCT/ISA/210) for International Application No. PCT/CN2012/085503, dated Mar. 7, 2013.
Keshri et al., "Uncultured *Bacillus* sp. clone UHAS5.77 16S ribosomalRNA gene, partial sequence," GenBank accession No. JN037948.1, Aug. 11, 2011.
Nakagawa et al., "Bacillus niacinigene for 16S rRNA, partial sequence, strain: NBRC 15566," GenBank accession No. AB680904.1, Jan. 28, 2012.
Extended European Search Report for European Application No. 12869142.5, dated Oct. 7, 2015.
Mo et al., "The influence of hyaluronic acid on vascular endothelial cell proliferation and the relationship with ezrin/merlin expression," Acta Biochimica et Biophysica Sinica Advance Access, Oct. 19, 2011, pp. 1-10, XP55215170.
Cui et al., "Research progress of low molecular weight and oligosaccharides of hyaluronan," Food and Drug, vol. 8, No. 3, Mar. 31, 2006, pp. 6-9, with a partial English translation.
Office Action and English Translation mailed Jan. 6, 2016 for Japanese Application No. 2014-557976.
Korean Office Action dated Apr. 20, 2016, for Korean Application No. 10-2014-7026162 with the English translation.
Nakagawa et al., "Bacillus niacini strain NBRC 15566 16S ribosomal RNA gene, partial sequence," Genbank Accession No. NR_113777, Nov. 10, 2011, 1 pg.

* cited by examiner

BACILLUS, HYALURONIDASE, AND USES THEREOF

TECHNICAL FIELD

The present invention pertains to the fields of enzymology and pharmaceutical chemistry, and relates to a *bacillus* sp., a hyaluronidase, and uses thereof. The present invention further relates to a process for preparing an oligomeric hyaluronic acid or salts thereof or a low-molecular-weight hyaluronic acid or salts thereof, and the uses of the *bacillus* sp., hyaluronidase, oligomeric hyaluronic acid or salts thereof, low-molecular-weight hyaluronic acid or salts thereof.

BACKGROUND ART

Hyaluronic acid (HA) is an acid mucopolysaccharide, a non-branched high molecular weight glycosaminoglycan consists of N-acetylglucosamine and D-glucuronic acid disaccharide repeating units, and exists in the intercellular substances of animal tissues or in the capsule of some bacteria. Hyaluronic acid is widely used in medicines, cosmetics and foods, and usually has molecular weight of $10^5$-$10^7$ Da (Dalton).

Oligomeric hyaluronic acid refers to hyaluronic acid with molecular weight of less than 10 k Da. Researches show that molecular weight remarkably influences the activity of hyaluronic acid, and hyaluronic acids with different molecular weights may have completely reversed activities (GUO, Xueping, et al, Low-molecular-weight and Oligomeric hyaluronic acids, Chinese Journal of Biochemical Pharmaceutics, 2003, 24(3): 148-150).

Researches show that oligomeric hyaluronic acid has the activity of promoting angiogenesis in vivo as well as the activity of promoting proliferation of endothelial cells in vitro, and can promote wound healing (West D C, Kumar S. The effect of hyaluronate and its oligosaccharides on endothelial cell proliferation and monolayer integrity. Exp Cell Res. 1989, 183(1): 179-96). Oligomeric hyaluronates have the biological activity of promoting angiogenesis, promoting wound healing, and possess good application prospect in the fields of medical and pharmaceutical.

During inflammatory process, oligomeric hyaluronic acid has potent activation effect on immunocompetent cells such as dendritic cells and macrophages (Termeer C, Benedix F, Sleeman J, et al. Oligosaccharides of Hyaluronan activate dendritic cells via toll-like receptor 4. J Exp Med. 2002, 195(1):99-111).

In vitro, oligomeric hyaluronic acid can inhibit growth of mice TA3/St breast cancer cells, rat CG neuroglioma cells, human HCT clone tumor cells and human LXI lung cancer cells, and has anti-tumor functions (Ghatak S, Misra S, Toole B P. Hyaluronan constitutively regulates ErbB2 phosphorylation and signaling complex formation in carcinoma cells. J Biol Chem. 2005, 280(10): 8875-83).

In addition, hydroxyl groups, carboxylic groups and other polar groups in oligomeric hyaluronates can form hydrogen band with water molecules so as to binding a large amount of water, thereby having significant water retention effect. Thus, oligomeric hyaluronates can be used in sun protection, anti-aging and moisturizing cosmetics.

At present, the methods for the degradation of hyaluronic acid are mainly divided into three groups: physical degradation, chemical degradation, and biological degradation. Physical degradation methods can hardly degrade hyaluronic acid to 10 k Da or below. Although chemical degradation methods and enzymatic methods can prepare oligomeric hyaluronic acid, chemical degradation methods need rigorous reaction conditions (e.g., high acid and base concentrations) to reach maximum degradation degree in preparing oligomeric hyaluronic acid. At the moment, the glucosidic bonds of saccharide chain are broken, and the structure of monosaccharide (glucuronic acid and acetylglucosamine) residues is broken as well, for example, the removal of acetyl groups by hydrolysis and the breakage of 6-membered ring of monosaccharide (the manifestation is the inconsistence in infrared spectrogram in comparison with the standard spectrum of European Pharmacopoeia), which have effects on biological activity of the obtained oligomeric hyaluronic acid (GUO Xueping, et al, Low-molecular-weight and Oligomeric Hyaluronic Acid, Chinese Journal of Biochemical Pharmaceutics, 2003, 24 (3): 148-150). The oligomeric hyaluronic acids prepared by chemical degradation methods are prone to browning (China Patent Application No. 201110008110.9), and production process thereof may pollute environment. When hyaluronic acid is prepared by enzymatic methods, only glucosidic bonds between monosaccharides are broken, and other structures are not broken. In addition, enzymatic methods employ moderate reaction conditions, and do not use strong acids and strong bases. The obtained oligomeric hyaluronic acids are not prone to browning, environmental pollution is avoided, and the oligomeric hyaluronic acids as prepared by enzymatic methods have integral structure and the infrared spectrum thereof is consistent with the standard spectrum of European Pharmacopoeia. Thus, enzymatic methods are most suitable for preparing oligomeric hyaluronic acid.

Enzymes used for degrading hyaluronic acid are mainly hyaluronidases, which can be divided into 3 groups according to their mechanisms: (1) endo-β-N-acetylglucosaminidase, a hydrolase and acts on) β-1,4-glucosidic bond, the main products are tetrasaccharides, can act on chondroitin or chondroitin sulfate and has transglycosidase activity; (2) hyaluronidase derived from hirudo or hookworm, it is endo-β-glucuronidase, acts on β-1,3-glucosidic bond, is also a hydrolase, the main degradation products are tetrasaccharides, can specifically degrade hyaluronic acid; (3) bacterial hyaluronidase, it is also called as hyaluronate lyase, acts on β-1,4-glucosidic bond, and produces 4,5-unsaturated disaccharides via β-elimination mechanism (Kreil, G, Hyaluronidases—a group of neglected enzymes, Protein Sci, 1995, 4(9): 1666-1669).

At present, methods for industrial production of oligomeric hyaluronic acid or salts thereof are chemical degradation methods. Since the sources of animal tissues containing hyaluronidase are limited, some reports show that microbe-sourced hyaluronidase fermentation broths have lower enzyme activity per unit, and the maximum enzyme activity of fermentation broths is $1.3 \times 10^2$ IU/mL (W02010130810A1; Eileen Ingham, K. T. Holland, G. Gowland and W. J. Cunliffe, Purification and Partial Characterization of Hyaluronate Lyase (EC4.2.2.1) from *Propionibacterium acnes*, Journal of General Microbiology (1979), 115, 411-418), other reports all show the enzyme activity of lower than 100 IU/mL, and hyaluronidase cannot be produced in large scale, and thus oligomeric hyaluronic acid or salts thereof cannot be produced in large scale by enzymatic methods.

In addition, hyaluronic acid with molecular weight of $10^4$ Da-$10^6$ Da is usually called as low-molecular-weight hyaluronic acid (LMW-HA). LMW-HA with molecular weight of 20,000-60,000 can stimulate the proliferation of bone cells cultured in vitro, increase the number of bone cell colonies and the area of single colony in cultural media (U.S. Pat. No. 5,646,129). By using eye drops containing tobramycin and HA with molecular weight of 500,000 in treatment of bacterial keratohelcosis, healing time was significantly shortened in comparison with eye drops containing tobramycin only (Gandolfi S A, Massari A, Orsoni J G. Low-molecular-weight sodium hyaluronate in the treatment of bacterial corneal ulcers s[J]. Graefes Arch Clin Exp Ophthalmol, 1992, 230(1): 20-23). Korea patent (KR20080087941) provides a composition of HA with molecular weight of less than 100,000, the composition is prone to absorption in human body, and oral administration thereof can effectively remove skin wrinkle and improve skin elasticity. Japanese patent (JP2000-103723) provides a composition containing HA with molecular weight of 200,000-400,000, the composition can promote hair growth. However, similar to oligomeric hyaluronic acid or salts thereof, LMW-HA or salts thereof as prepared by enzymatic degradation methods are more integral in structure than those prepared by chemical methods, and LMW-HA or salts thereof as prepared by chemical methods may have ring opening and deacetylation in their structure.

LMW-HA has smaller relative molecular weight, and thus can be well absorbed by skin in external use, promote skin nutrient supply and waste excretion, so as to prevent skin aging, achieve deep moisturizing and maintain beauty, promote proliferation and differentiation of epithelial cells, scavenge free radicals, as well as repair skin injury caused by sun light or ultraviolet light. Oral LMW-HA is prone to absorption, can activate skin cells, keep skin moisture and meanwhile provide well immune-enhancement function and anti-aging function. Thus, the HA used in cosmetics and health foods are usually LMW-HA. In addition, LMW-HA can also promote angiogenesis, cell immunity activation and osteogenesis, has good therapeutic effects in treatment of bacterial keratohelcosis, and thus is widely used in the field of medicine.

LMW-HA is obtained by degrading high molecular weight HA, and degradation methods are mainly 3 groups, i.e., physical degradation, chemical degradation, and biological degradation. Although ultrasonic degradation method as physical degradation method is free of chemical agents and enzymes, it can hardly degrade high molecular weight HA to reach molecular weight of 200 k Da or below (QIN Caifeng, WANG Miao, CHEN Xiaofeng, Studying of Degradation methods and Process Conditions of Hyaluronic Acid, [J]. 2007, 4: 32-36). Mechanical grinding method is also an effective method to reduce relative molecular weight of HA. A patent discloses grinding time at room temperature is 0.5 h-12 h, oscillation frequency is 10 Hz-30 Hz, but it is not suitable for production in large scale (CN101942037A). Chemical degradation method may break structure, which may break not only glucosidic bonds of saccharide chain, but also structure of monosaccharide (glucuronic acid and acetylglucosamine) residues, for example, acetyl groups are removed by hydrolysis and 6-membered ring of monosaccharide is broken.

Some reports show a process for preparing low-molecular-weight HA by enzymatic degradation method, in which HA is firstly isolated and purified from fermentation broth, then hyaluronidase is added for enzymatic degradation, following membrane filtration, ethanol precipitation, dehyarating and drying to obtain low-molecular-weight HA (CN101020724A), the hyaluronidase used in the process is a finished product of hyaluronidase, which is very expensive and can hardly be used for industrial production. At present, some reports show microbe-sourced hyaluronidase fermentation broths have lower enzyme activity per unit, the maximum enzyme activity of fermentation broths is $1.3 \times 10^2$ IU/mL (W02010130810A1), other reports all show enzyme activity of lower than 100 IU/mL, therefore, at present, low-molecular-weight HA can hardly be produced in large scale by enzymatic methods.

CONTENTS OF THE INVENTION

The inventors made efforts in deep research and inventive work and thereby obtained a *bacillus* as well as a hyaluronidase. The hyaluronidase has high activity of up to $10^5$ IU/mL (fermentation broth), and $8 \times 10^6$-$1.5 \times 10^7$ IU/mg after purification, which are far greater than the highest enzyme activity as reported in the current documents. The hyaluronidase has a molecular weight of 123 kDa, a most suitable temperature 42° C. and a most suitable pH 6.5, and has good thermal stability and pH stability. The enzyme can catalytically crack hyaluronic acid and chondroitin sulfate, but cannot degrade sodium alginate, heparin sodium, chitosan, chitin and carboxymethyl cellulose sodium. It has high reaction speed, moderate reaction conditions, less environmental pollution when Using the hyaluronidase to degrade high molecular weight hyaluronic acid, thus it is suitable for industrial production of low-molecular-weight hyaluronic acid and oligomeric hyaluronic acid in large scale, and it can also be used for production of low-molecular-weight chondroitin sulfate (in the present invention, referring to chondroitin sulfate with molecular weight of 1,000-10,000, which is also called as LMW chondroitin sulfate). The hyaluronidase obtained in the present invention by using the *bacillus* in fermentation is useful in degradation of high molecular weight hyaluronic acid or salts thereof, showing high enzyme activity, with moderate conditions, simple in operation and free of environmental pollution; in addition, the obtained oligomeric hyaluronic acid or salts thereof or low-molecular-weight hyaluronic acid or salts thereof have integral structure, and are free of browning. Thus, the following invention is provided.

One aspect of the present invention relates to a *bacillus* sp., which has a deposit access number of CGMCC NO. 5744, deposit date of Feb. 8, 2012, and depositary institution name of China General Microbiological Culture Collection Center (CGMCC).

In order to overcome drawbacks such as low enzyme activity, source limitation and high cost in biological degradation of hyaluronic acid or salts thereof in the prior art, the inventors had isolated from air a *bacillus* (*Bacillus* sp.) A50 that produces hyaluronidase, and this strain had been deposited in China General Microbiological Culture Collection Center (CGMCC) with deposit access number of CGMCC NO. 5744, and deposit date of Feb. 8, 2012.

Another aspect of the present invention relates to a process for preparing hyaluronidase, comprising the step of using the *bacillus* of the present invention; specifically, comprising the following steps:

subjecting the *bacillus* of the present invention to slant culture, seed culture, fermentation culture, centrifugation, ammonium sulfate fractional precipitation, ultrafiltration, to obtain a hyaluronidase.

The process for preparing hyaluronidase according to any one of items of the present invention, comprising the following steps:

(1) subjecting the *bacillus* of the present invention to slant culture to obtain a slant strain;

(2) inoculating the slant strain to a sterilized seed culture medium, and culturing under conditions of 25°-40° C., 100-200 rpm for 10-24 hours, to obtain a seed solution;

(3) inoculating the seed solution to a sterilized fermentation culture medium, and culturing under conditions of 25°-40° C., 100-300 rpm for 12-24 hours, to obtain a hyaluronidase fermentation broth;

(4) separating the fermentation broth by centrifugation to obtain a supernatant;

(5) subjecting the supernatant to ammonium sulfate fractional precipitation, filtration (e.g., filtration using 0.65 μm microfiltration membrane), to obtain a crude hyaluronidase;

(6) dissolving the crude hyaluronidase as precipitated in step (5) in a phosphate buffer solution, removing small molecular impurities by ultrafiltration, to obtain a purified hyaluronidase.

Optionally, the step (6) can be carried out by the following steps (6-1) to (6-3):

(6-1): dissolving the crude hyaluronidase of step (5) in a buffer solution with pH 4.5-8.0 to obtain a crude enzyme solution; loading the crude enzyme solution to a dialysis bag with a molecular cutoff of $3.0 \times 10^3$-$1.4 \times 10^4$ Da, placing in a buffer solution with pH 4.5-8.0, dialyzing at 4° C. overnight;

(6-2): subjecting the dialyzed crude enzyme solution to ion exchange chromatography separation, in which chromatography column packing of DEAE agarose gel FF medium and 0-0.5M NaCl solution for gradient elution are used, and collecting elution peaks;

(6-3): subjecting the hyaluronidase sample obtained in step (6-2) to vacuum freeze drying to obtain white powder as hyaluronidase.

Steps (6-1) to (6-3) are to further purify hyaluronidase.

In the above process for separating and purifying hyaluronidase, the hyaluronidase obtained in step (6-2) has a purity of 97% or more measured by SDS-PAGE electrophoresis.

In the above step (1), per 100 mL of slant culture medium contains the following components: peptone 0.2-2.0 g, yeast powder 0.2-2.0 g, $K_2HPO_4 \cdot 3H_2O$ 0.05-0.15 g, $MgSO_4 \cdot 7H_2O$ 0.05-0.15 g, glucose 0.5-1.5 g, agar powder 2.0 g; pH being adjusted to 6.0-8.0, slant culture temperature being 25° C.-40° C.

In the above step (2), per 100 mL of seed culture medium contains the following components: peptone 0.2-2.0 g, yeast powder 0.2-2.0 g, $K_2HPO_4 \cdot 3H_2O$ 0.05-0.15 g, $MgSO_4 \cdot 7H_2O$ 0.05-0.15 g, glucose 0.5-1.5 g; pH being adjusted to 6.0-8.0.

In the above step (3), per 100 mL fermentation culture medium contains the following components: peptone 0.2-2.0 g, yeast powder 0.2-2.0 g, $K_2HPO_4 \cdot 3H_2O$ 0.05-0.15 g, $MgSO_4 \cdot 7H_2O$ 0.05-0.15 g, glucose 0.5-1.5 g, TWEEN 80 0.05 mL; pH being adjusted to 6.0-8.0.

One or more of hydrochloric acid, sulfuric acid or phosphoric acid are used to adjust pH of the slant culture medium, seed culture medium and fermentation culture medium.

Inoculation amount for slant, seed culture and fermentation can be obtained in the prior art without inventive work. The inoculation amount for seed culture medium is sufficient to obtain inoculation amount of seed solution for fermentation culture, and the inoculation amount for fermentation culture medium is usually 3%-15%.

In the above step (4), the rotation speed of the centrifugation of fermentation broth is 10000-15000 rpm, and the centrifugation time is 10-20 minutes.

In the above step (5), the ammonium sulfate fractional precipitation comprises the following steps: adding to the supernatant with ammonium sulfate, to reach a concentration of 20% w/v-25% w/v, removing the generated precipitate by filtration, then continuously adding with ammonium sulfate, until reaching a concentration of 35%-40% w/v, to obtain a precipitate as hyaluronidase. In the present invention, the "w/v concentration" refers to: mass (g) of ammonium sulfate in per mL of the supernatant.

In the above step (6), phosphate buffer solution has pH of preferably 6.0, concentration preferably of 50 mmol/L, which may change according to circumstances in practice. The ultrafiltration uses ultrafiltration membrane. The ultrafiltration membrane has a molecular cutoff of $3 \times 10^4$ Da.

Further another aspect of the present invention relates to a hyaluronidase, which is obtained by the process for preparing hyaluronidase according to any one of the preceding items.

The hyaluronidase as produced by the *bacillus* of the present invention has a enzyme activity of up to $1 \times 10^5$-$3 \times 10^5$ IU/mL in fermentation broth, which is far greater than the highest enzyme activity ($1.3 \times 10^2$ IU/mL) as reported, and the enzyme has high thermal stability and pH stability. When it is used to degrade high molecular weight hyaluronic acid to produce oligomeric or low-molecular-weight hyaluronic acid, the cost is significantly reduced, and it can be used for production in large scale. Thus, the problem of high cost of hyaluronidase derived from animals is solved. It is promising in application in biological researches and production of oligomeric or low-molecular-weight hyaluronic acid.

The present invention further relates to an isolated polypeptide (or protein), of which the amino acid sequence is shown in SEQ ID NO: 2; specifically, the polypeptide (or protein) is hyaluronidase.

The present invention further relates to an isolated polynucleotide, which encodes the amino acid sequence as shown in SEQ ID NO: 2; specifically, the polynucleotide is the sequence as shown in SEQ ID NO: 3 or the complementary sequence of SEQ ID NO: 3.

The present invention further relates to a recombinant vector, which comprises the polynucleotide of the present invention.

The present invention further relates to a host cell, which comprises the recombinant vector of the present invention.

Further another aspect of the present invention relates to a process for preparing oligomeric hyaluronic acid or oligomeric hyaluronate, comprising the step of degrading hyaluronic acid or salts thereof with molecular weight greater than 10 k Da by using the hyaluronidase according to any one of items of the present invention or the fermentation broth containing the hyaluronidase according to any one of items of the present invention.

The process for preparing oligomeric hyaluronic acid or oligomeric hyaluronate according to the present invention, comprising the following steps:

1) preparing the solution of hyaluronic acid or salts thereof: adding hyaluronic acid or salts thereof with molecular weight greater than 10 k Da to purified water, to obtain a solution with a concentration of 1% w/v-30% w/v;

2) enzymolysis: adjusting the temperature of the solution of step 1) to 20° C.-48° C., pH to 4-9, then adding *bacillus* hyaluronidase to the solution, degrading the hyaluronic acid or salts thereof to a desired molecular weight, to obtain a enzymolysis solution;

3) inactivation: maintaining the enzymolysis solution at 50° C.-90° C. for 10-60 minutes, to inactivate the *bacillus* hyaluronidase;

preferably, further comprising the following steps:

4) filtration: adding a soluble inorganic salt to the inactivated w/v, stirring until completely dissolved, then filtering with 0.45 μm filtration membrane to obtain a filtrate, wherein to per 100 mL of enzymatic hydrolysate, 0.1-10 g of the soluble inorganic salt is added;

5) precipitation: uniformly mixing the filtrate of step 4) with alcohol or ketone in 3-20 times volume of the filtrate, to precipitate oligomeric hyaluronate;

6) dehyarating and drying: separating out the oligomeric hyaluronate precipitate of step 5), dehydrating with a organic solvent, then vacuum drying, to obtain oligomeric hyaluronate.

The process for preparing oligomeric hyaluronic acid or oligomeric hyaluronate according to the present invention, wherein, in step 1), to per 1 kg of hyaluronic acid or salts thereof, $2 \times 10^7$-$5 \times 10^7$ IU of *bacillus* hyaluronidase is added.

The process for preparing oligomeric hyaluronic acid or oligomeric hyaluronate according to the present invention, wherein, in step 2), the temperature for enzymolysis is 35° C.-45° C., the pH for enzymolysis is 5.5-7.5, and hyaluronic acid is enzymolyzed to have a molecular weight of greater than or equal to 3000 Da, and less than $10^4$ Da.

The process for preparing oligomeric hyaluronic acid or oligomeric hyaluronate according to the present invention, which satisfying one or more of the following A-F:

A. in step 1), hyaluronate is selected from the group consisting of sodium salt, potassium salt, magnesium salt, calcium salt and zinc salt of hyaluronic acid;

B. in step 2), an acid or a base is used to adjust pH to 4-9, said acid is selected from the group consisting of hydrochloric acid, glacial acetic acid, sulfuric acid and phosphoric acid, said base is sodium hydroxide or potassium hydroxide;

C. in step 3), the enzymolysis solution is kept at 55° C.-65° C. for 20-30 minutes, to inactivate the *bacillus* hyaluronidase;

D. in step 4), said soluble inorganic salt is selected from the group consisting of sodium salt, potassium salt, calcium salt, zinc salt and magnesium salt; preferably, is chloride, sulfate or nitrate of sodium, potassium, calcium, zinc or magnesium;

E. in step 5), said alcohol or ketone is ethanol, acetone, methanol, propanol, or isopropanol;

F. in step 6), the organic solvent used for dehydrating is ketone or alcohol.

In the above process, the specific activity of the *bacillus* hyaluronidase used i.e. the purified hyaluronidase obtained by fermentation of *bacillus* (*Bacillus* sp.) A50 CGMCC NO. 5744 is $8 \times 10^6$-$1.5 \times 10^7$ IU/mg, and the amount of enzyme to be added for per kg of hyaluronic acid or salts thereof is $2 \times 10^7$ $5 \times 10^7$ IU. The hyaluronidase has a good degradation activity to hyaluronic acid, and hyaluronic acid with any small molecular weight can be obtained by adding a suitable amount of the hyaluronidase, so that during the enzymolysis, hyaluronic acid with desired molecular weight can be obtained by control the length of time period.

In addition, step 4) uses filtration membrane to filter the enzymatic hydrolysate so as to remove impurities such as hyaluronidase and to improve purity of production. The filtration membrane is common filtration membrane in the prior art, as long as it meets requirements of pore diameter of the present invention. The pore diameter of filtration membrane is 0.45 μm, and the material thereof can be cellulose esters, polysulfones, or polyamides.

In the above step 6), the organic solvent used for dehydrating is an organic solvent mutually soluble with water; preferably, the organic solvent is ketone or alcohol, and most preferably, ethanol and/or acetone. Without being bounded by any theory, said organic solvent is added to oligomeric hyaluronate precipitate to remove most of water in the precipitate.

The process for preparing oligomeric hyaluronic acid or salts thereof of the present invention is simple in operation, with moderate conditions, without breaking structure of products, free of environmental pollution, low cost in fermentation-derived hyaluronidase, suitable for industrial production in large scale, and the prepared oligomeric hyaluronate has integral structure, good transdermal absorption, high purity, no cytotoxicity, strong antioxidant ability, and can be widely used in cosmetics, foods and medicines.

Further another aspect of the present invention relates to an oligomeric hyaluronic acid or oligomeric hyaluronate, which is obtained by the process for preparing oligomeric hyaluronic acid or oligomeric hyaluronate according to any one items of the present invention.

Further another aspect of the present invention relates to an oligomeric hyaluronic acid or oligomeric hyaluronate, which has N-acetylglucosamine and D-glucuronic acid disaccharide in amount of ≥65%, ≥70%, ≥80%, ≥85%, ≥90% or ≥95% (w/w); specifically, the amount of N-acetylglucosamine and D-glucuronic acid disaccharide is measured by HPLC method. More specifically, the conditions of HPLC are as follows: using saccharide analysis column to perform high performance liquid chromatography measurement; mobile phase being 0.4 mol/L $NaH_2PO_4$ solution; flow rate being 0.6 ml/min, column temperature being 35° C.; detection wavelength being 232 nm; and sample size being 20 μL.

For example, the following steps can be used:

a. standard control solution: weighing an amount of standard control (Hyaluronic acid disaccharide ΔDiHA sodium salt, H9649, Sigma), dissolving with phosphate buffer solution (pH6.0, 5 mmol/L) to formulate 1 mg/mL solution, and thus obtaining standard control solution;

b. sample pretreatment: weighing an amount of sample to be tested (prepared by Comparative Examples 1-7, Examples 13-26), dissolving with phosphate buffer solution (pH6.0, 5 mmol/L) to formulate 1 mg/mL solution. 1 mL of sample solution is added with 1000 IU of hyaluronidase (can be prepared by Examples 10-12), subjected to 42° C. water bath for 2 h; after enzymolysis, the enzymolysis solution is boiled for 2 minutes to inactivate the enzyme, and thus obtain sample enzymolysis solution.

The sample enzymolysis solution is transferred to a 20 mL volumetric flask, added with mobile phase to the scale, mixed uniformly, and filtered to obtain a solution to be tested.

c. treatment of standard control solution: 1 mL of standard control solution is diluted with mobile phase by 20 times, and filtered for standby use.

d. chromatography conditions: using saccharide analysis column to perform high performance liquid chromatography measurement; mobile phase being 0.4 mol/L $NaH_2PO_4$ solution; flow rate being 0.6 ml/min; column temperature being 35° C.; detection wavelength being 232 nm; sample size being 20 μL;

e. result calculation: using high performance liquid chromatography to perform chromatography separation of standard control and sample to be tested, and calculating hyaluronic acid disaccharide peak area by external standard method; specifically, using the following formula to calculate the content of oligomeric hyaluronic acid or salts thereof (expressed in the content of N-acetylglucosamine and D-glucuronic acid disaccharide):

The content of oligomeric hyaluronic acid or salts thereof:

$$C(\%) = \frac{A_X \times C_R \times 100}{A_R \times W_X \times (100-h)} \times 100\%$$

$A_X$: peak area of hyaluronic acid disaccharide of the sample to be tested;

$A_R$: peak area of hyaluronic acid disaccharide of the standard control;

Wx: amount of the sample to be tested, mg;

$C_R$: concentration of the standard control solution, mg/mL;

h(%) is drying loss of the sample to be tested.

Specific method can also be read in China Patent Application with publication number of CN102323344A, which all contents are incorporated into the present invention by reference.

Regarding to the oligomeric hyaluronic acid or oligomeric hyaluronate according to any one of items of the present invention, its content as measured by HPLC method and its content as measured by carbazole method has a difference of less than 1%.

The oligomeric hyaluronic acid or oligomeric hyaluronate according to any one of items of the present invention has a molecular weight of greater than or equal to 3000 Da, and less than $10^4$ Da. Specifically, the oligomeric hyaluronic acid or oligomeric hyaluronate is prepared by enzymolysis method (enzyme digestion method); more specifically, prepared by using hyaluronidase of the present invention.

The oligomeric hyaluronate according to any one of items of the present invention is white powder or granules, its content is greater than 95%, and its 0.1% aqueous solution has pH of 6-8. Its infrared spectrum is in consistent with the standard spectrum of European Pharmacopoeia, its property is good, and its structure is not broken.

Further another aspect of the present invention relates to a process for preparing a low-molecular-weight hyaluronic acid or low-molecular-weight hyaluronate, comprising the step of degrading hyaluronic acid or salts thereof with molecular weight of greater than 1000 k Da using the hyaluronidase according to any one of items of the present invention or the fermentation broth containing the hyaluronidase according to any one of items of the present invention.

The process for preparing low-molecular-weight hyaluronic acid or low-molecular-weight hyaluronate according to any one of items of the present invention, comprising the following steps:

1) preparing a solution of hyaluronic acid or salts thereof: adding hyaluronic acid or salts thereof with molecular weight of greater than 1000 k Da to purified water, to obtain a solution with a concentration of 0.1% w/v-2% w/v;

2) enzymolysis: adjusting the temperature of the solution of step 1) to 20° C.-48° C., pH to 4-9, then adding *bacillus* hyaluronidase to the solution, degrading the hyaluronic acid or salts thereof to a desired molecular weight, to obtain a enzymolysis solution;

3) inactivation: keeping the enzymolysis solution at 50° C.-90° C. for 10-60 minutes, to inactivate the *bacillus* hyaluronidase;

preferably, further comprising the following steps:

4) filtration: adding a soluble inorganic salt to the inactivated enzymolysis solution, stirring until it is completely dissolved, then filtering with 0.45 μm filtration membrane to obtain a filtrate, wherein to per 100 mL of ° C., 0.1-10 g of the soluble inorganic salt is added;

5) precipitation: uniformly mixing the filtrate of step 4) with alcohol or ketone in 1-10 times volume of the filtrate, to precipitate low-molecular-weight hyaluronate;

6) dehydrating and drying: separating out the low-molecular-weight hyaluronate precipitate of step 5), dehydrating with an organic solvent, then vacuum drying, to obtain low-molecular-weight hyaluronate.

The process for preparing low-molecular-weight hyaluronic acid or low-molecular-weight hyaluronate according to any one of items of the present invention, wherein, in step 1), to per 1 kg of hyaluronic acid or salts thereof, $10^6$-$10^7$ IU of *bacillus* hyaluronidase is added.

The process for preparing low-molecular-weight hyaluronic acid or low-molecular-weight hyaluronate according to any one of items of the present invention, wherein, in step 2), the temperature for enzymolysis is 35° C.-45° C., pH for enzymolysis is 5.5-7.5, and the hyaluronic acid is enzymolyzed to a molecular weight of 10 kDa-1000 kDa; preferably 10 kDa-770 kDa or 10 kDa-700 kDa or 10 kDa-600 kDa or 10 kDa-500 kDa; more preferably 10 kDa-400 kDa; more preferably 10 kDa-300 kDa, 10 kDa-200 kDa, 10 kDa-150 kDa, 10 kDa-100 kDa, 10 kDa-50 kDa or 10 kDa-30 kDa.

The process for preparing low-molecular-weight hyaluronic acid or low-molecular-weight hyaluronate according to any one of items of the present invention, which satisfying one or more of the following A-F:

A. in step 1), hyaluronate is selected from the group consisting of sodium salt, potassium salt, magnesium salt, calcium salt and zinc salt of hyaluronic acid;

B. in step 2), an acid or a base is used to adjust pH to 4-9, said acid is selected from the group consisting of hydrochloric acid, glacial acetic acid, sulfuric acid and phosphoric acid, said base is sodium hydroxide or potassium hydroxide;

C. in step 3), the enzymolysis solution is kept at 55° C.-65° C. for 20-30 minutes, to inactivate the *bacillus* hyaluronidase;

D. in step 4), the soluble inorganic salt is selected from the group consisting of sodium salt, potassium salt, calcium salt, zinc salt and magnesium salt; preferably, is chloride, sulfate or nitrate of sodium, potassium, calcium, zinc or magnesium;

E. in step 5), said alcohol or ketone is ethanol, acetone, methanol, propanol, or isopropanol;

F. in step 6), the organic solvent used for dehydrating is ketone or alcohol.

Further another aspect of the present invention relates to a low-molecular-weight hyaluronic acid or low-molecular-weight hyaluronate, which is prepared by the process for preparing low-molecular-weight hyaluronic acid or low-molecular-weight hyaluronate according to any one of items of the present invention.

Further another aspect of the present invention relates to a low-molecular-weight hyaluronic acid or low-molecular-weight hyaluronate, which has N-acetylglucosamine and D-glucuronic acid disaccharide in amount of ≥90% or ≥95% (w/w); specifically, the amount of N-acetylglucosamine and D-glucuronic acid disaccharide is measured by HPLC method. More specifically, the conditions of HPLC are as follows: using saccharide analysis column to perform high performance liquid chromatography measurement; mobile phase being 0.4 mol/L $NaH_2PO_4$ solution; flow rate being 0.6 ml/min, column temperature being 35° C.; detection wavelength being 232 nm; and sample size being 20 μL.

Specific method can also refer to the above method for measuring the content of oligomeric hyaluronic acid or salts thereof (content of N-acetylglucosamine and D-glucuronic acid disaccharide).

The low-molecular-weight hyaluronic acid or low-molecular-weight hyaluronate according to any one of items of the present invention has a molecular weight of 10 kDa-1000 kDa; preferably 10 kDa-770 kDa or 10 kDa-700 kDa or 10 kDa-600 kDa or 10 kDa-500 kDa; more preferably 10 kDa-400 kDa; more preferably 10 kDa-300 kDa, 10 kDa-200 kDa, 10 kDa-150 kDa, 10 kDa-100 kDa, 10 kDa-50 kDa or 10 kDa-30 kDa. Specifically, the low-molecular-weight hyaluronic acid or low-molecular-weight hyaluronate is prepared by enzymolysis method (enzyme digestion method); more specifically, prepared by using the hyaluronidase of the present invention.

Regarding to the low-molecular-weight hyaluronic acid or low-molecular-weight hyaluronate according to any one of items of the present invention, its content as measured by HPLC method and its content as measured by carbazole method has a difference of less than 1%.

Without being bounded by any theory, when the same amount of enzyme is used, hyaluronic acid with different molecular weight can be obtained by controlling different enzymolysis time, i.e., low-molecular-weight hyaluronic acid or oligomeric hyaluronate can be obtained by controlling a suitable enzymolysis time. However, in practice, enzyme activity may decrease after long period of time, and solution of hyaluronate may be contaminated with bacteria, so preferably, hyaluronic acid with different molecular weight is obtained by controlling addition of different amount of enzyme, for example, the preparation of low-molecular-weight hyaluronate needs less amount of enzyme, while the preparation of oligomeric hyaluronate need more amount of enzyme.

The molecular weight of the product can be measured by sampling in a interval manner. The molecular weight of oligomeric hyaluronate and low-molecular-weight hyaluronate can be measured by GPC-MALLS method or Laurent method (GPC-MALLS method is more convenient); those skilled in the art can select suitable time interval for detection according to the knowledge in the art.

Further another aspect of the present invention relates to a composition, which comprises the hyaluronidase according to any one of items of the present invention, the polynucleotide of the present invention, the recombinant vector of the present invention, the recombinant host cell of the present invention, or the low-molecular-weight hyaluronic acid or low-molecular-weight hyaluronate according to any one of items of the present invention; optionally, which further comprises a pharmaceutically acceptable or bromatologically acceptable carrier or excipient; specifically, the composition being cosmetic, food, or drug; more specifically, the cosmetic being sun protection, post-sunburn repairing, anti-aging, or moisturizing cosmetic.

Further aspect of the present invention relates to a use of the *bacillus* of the present invention, the polynucleotide of the present invention, the recombinant vector of the present invention, or the recombinant host cell of the present invention in the manufacture of hyaluronidase.

Using the technical means known in the art, the polynucleotide encoding hyaluronidase according to the present invention can be cloned to an expression vector, transduced to a suitable host cell, to express the hyaluronidase of the present invention.

The present invention further relates to a use of the hyaluronidase according to any one of items of the present invention in manufacture of oligomeric acid or oligomeric hyaluronate, low-molecular-weight hyaluronic acid or low-molecular-weight hyaluronate, or low-molecular-weight chondroitin sulfate.

The present invention further relates to a use of the oligomeric acid or oligomeric hyaluronate according to any one of items of the present invention, or the low-molecular-weight hyaluronic acid or low-molecular-weight hyaluronate according to any one of items of the present invention in the manufacture of a medicament for promoting angiogenesis and/or promoting wound healing, or antioxidation, or scavenging free radical, or sun protection, or post-sunburn repairing, or promoting proliferation of HUVEC cells, or anti-tumor (such as breast tumor, lung cancer, or neurospongioma), or enhancing immunity, or in the manufacture of a food or health care product or cosmetic; specifically, the cosmetic being a sun protection, post-sunburn repairing, anti-aging, or moisturizing cosmetic.

Further another aspect of the present invention relates to a method for promoting angiogenesis and/or promoting wound healing, or antioxidation, or scavenging free radical, or promoting proliferation of HUVEC cells, or inhibiting tumor (such as breast tumor, lung cancer, or neurospongioma), in vivo or in vitro, comprising the step of administering to a subject or using an effective amount of the oligomeric acid or oligomeric hyaluronate according to any one of items of the present invention, or the low-molecular-weight hyaluronic acid or low-molecular-weight hyaluronate according to any one of items of the present invention; specifically, the subject being a mammal, more specifically, the subject being a human.

In the present invention, unless otherwise specified, "oligomeric hyaluronic acid or oligomeric hyaluronate" can also be briefly called as "oligomeric hyaluronic acid or salts thereof", oligomeric hyaluronic acid or oligomeric hyaluronate has a molecular weight of less than 10 kDa; preferably, greater than or equal to 3000 Da, and less than $10^4$ Da. The kind of oligomeric hyaluronate is not specifically limited, comprising but not being limited to: sodium salt, potassium salt, calcium salt, magnesium salt, zinc salt, and so on.

In the present invention, unless otherwise specified, "low-molecular-weight hyaluronic acid or low-molecular-weight hyaluronate" can also be briefly called as "low-molecular-weight hyaluronic acid or salts thereof", low-molecular-weight hyaluronic acid or low-molecular-weight hyaluronate has a molecular weight of 10 kDa-1000 kDa; preferably, 10 kDa-500 kDa; more preferably 10 kDa-400 kDa; further preferably 10 kDa-300 kDa, 10 kDa-200 kDa, 10 kDa-150 kDa, 10 kDa-100 kDa, 10 kDa-50 kDa or 10 kDa-30 kDa. The kind of low-molecular-weight hyaluronate is not specifically limited, comprising but not being limited to: sodium salt, potassium salt, calcium salt, magnesium salt, zinc salt, and so on.

In the present invention, regarding to the percentage of content of certain component, unless otherwise specified, it refers to weight percentage (w/w).

Some other terms of the present invention are shown in the below.

Expression Vector

The present invention also relates to a recombinant expression vector comprising the nucleotide sequence of the present invention, a promoter as well as transcription and translation termination signals. The above various nucleic acids and regulatory sequences can be linked together to prepare the recombinant expression vector, the vector can comprise one or more convenient restriction sites, so as to insert or substitute nucleotide sequence encoding hyaluronidase at these sites. Or, the nucleotide sequence of the present invention can be expressed by inserting the nucleotide sequence or a nucleotide construct containing the sequence into a suitable expression vector. When preparing the expression vector, the encoding sequence can be located in the vector so as to be operationally linked to a suitable expression regulatory sequence.

The recombinant expression vector can be any vector (e.g., plasmid or virus) suitable for performing recombinant DNA operation and expressing the nucleotide sequence. The vector is usually selected according to the compatibility of the vector and the host cell to which it would be introduced. The vector can be linear or closed loop plasmid.

The vector can be self-replicating vector (i.e., extrachromosomal unbroken structure, which can be replicated without chromosome), such as plasmid, extrachromosomal element, micro-chromosome, or artificial chromosome. The vector can contain any mechanism for self-replication. Or, the vector is such a vector, when it is introduced in a host cell, it is integrated in genome and replicated together with the chromosome to which it is integrated. In addition, single vector or plasmid, or two or more vectors or plasmids generally contain whole DNA to be introduced to the host cell genome, or transposons can also be used.

Preferably, the vector of the present invention comprises one or more selective markers for selecting transformed cells. The selective marker is a gene that gives the product a resistance against biocide or virus, a resistance against a heavy metal, or gives auxotrophic prototrophy. Examples of bacterial selective markers can be dal gene of *bacillus subtilis*, or *bacillus licheniformis*, or resistance markers for antibiotics such as ampicillin, kanamycin, chloromycetin or tetracycline.

Preferably, the vector of the present invention comprises elements ensuring stable integration of the vector into host cell genome, or ensuring the self-replication of the vector in cell without depending on cell genome.

Regarding to self-replication, the vector can comprise replication origin so as to ensure the self-replication in the target host cell. The replication origin can comprise mutation that changes it into temperature-sensitive type in host cell (see, for example, fEhrlich, 1978, Proceedings of the National Academy of Sciences 75: 1433).

One or more copies of the nucleotide sequence of the present invention can be inserted in host cells so as to increase the yield of genetic products. The increase of copy number of the nucleotide can be carried out by inserting at least one additional copy of the sequence into host cell genome, or inserting a selective marker capable of amplification together with the nucleotide sequence, culturing cell in presence of a suitable selective agent, picking out selective marker gene containing amplified copies, so as to obtain cells containing additional copies of the nucleotide sequence.

The operations for linking the above elements to construct the recombinant expression vector of the present invention are well known in the art (see, for example, Sambrook, et al, Molecular Cloning Manual, $2^{nd}$ Edition, Cold Spring Harbor Laboratory Press, Cold Spring Harbor, N.Y., 1989).

Host Cell

The present invention further relates to a recombinant host cell for recombination of the nucleotide sequence (polynucleotide) of the present invention for production of hyaluronidase. The vector containing the nucleotide sequence of the present invention can be introduced into a host cell, so that the vector is maintained in form of the chromosome integrant or self-replicating extrachromosomal vector. The term "host cell" covers all off-springs different from parent cell due to mutations during replication. The selection of host cell mainly depends on gene encoding hyaluronidase and source thereof.

The host cell can be prokaryotic cell or eukaryotic cell, such as bacterial or yeast cells. The vector can be introduced into the host cell by technologies known by those skilled in the art.

Preparation Method

The present invention further relates to a method for recombination production of hyaluronidase of the present invention, comprising: (a) culturing host cells containing nucleotide construct under conditions suitable for generation of hyaluronidase, the nucleotide construct comprising the nucleotide sequence encoding the hyaluronidase; and (b) recovering the peptide.

In the preparing method of the present invention, cells are cultured in culture medium suitable for production of hyaluronidase. For example, in a suitable culture medium, under conditions allowing expression and/or separation of hyaluronidase, cells are cultured in shake flasks, laboratory or industrial fermentation tanks for fermentation in small or large scale (including, continuous, in batches, batch charge, or solid state fermentation). In suitable culture medium containing carbon source and nitrogen source as well as inorganic salts, steps known in the art are used for culturing. Suitable culture medium can be provided by manufacturer or prepared according to known composition (e.g., those in catalog of American Type Culture Collection). If hyaluronidase is secreted into the culture medium, it can be directly recovered from the culture medium. If hyaluronidase is not secreted, it can be recovered from cell lysis products.

The produced hyaluronidase can be recovered by known methods in the art. For example, it can be recovered from culture medium by conventional operation (including, but not being limited to centrifugation, filtration, extraction, spray drying, evaporation or precipitation).

The hyaluronidase of the present invention can be purified by steps known in the art, and these steps include but are not limited to chromatography (e.g., ion exchange chromatography, affinity chromatography, hydrophobic interaction chromatography, chromatofocusing, and size exclusion chromatography), HPLC, electrophoresis (e.g., preparative isoelectric focusing), differential solubility (e.g., ammonium sulfate precipitation), SDS-PAGE or extraction (see, for example, Protein Purification, edited by J. C. Janson and Lars Ryden, VCH Publishers, New York, 1989).

Beneficial Effects of the Invention

In the present invention, the process of using *bacillus* to produce oligomeric hyaluronic acid or salts thereof or low-molecular-weight hyaluronic acid or salts thereof is simple in operations, with moderate conditions, no damage to the structure of the products, no environmental pollution, and low cost for hyaluronidase from fermentation source, and suitable for industrial production in large scale. The oligomeric hyaluronate or low-molecular-weight hyaluronate of the present invention has advantages such as integral structure, high purity, no cytotoxicity, potent antioxidant ability, no browning in color, and can be used in fields of cosmetics, foods and medicines.

BRIEF DESCRIPTION OF DRAWINGS

FIG. 2: infrared spectra of oligomeric hyaluronate prepared by different methods, wherein:

FIG. 3: effects of temperature on hyaluronidase activity and experimental results of thermal stability of hyaluronidase.

FIG. 4: effects of pH on hyaluronidase activity and experimental results of pH stability of hyaluronidase.

Figure 1:
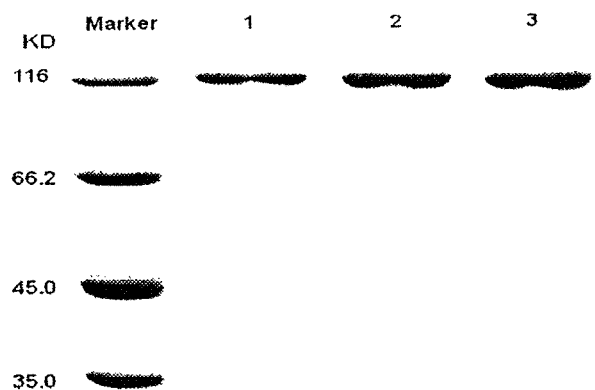
FIG. 1: SDS-PAGE electrophoretogram, in which, Marker is Unstained Protein Molecular Weight Marker; lanes 1, 2, 3 are hyaluronidase prepared in Examples 10, 11, 12 respectively.

Deposited biological materials related to the present invention:

The bacillus (Bacillus sp.) A50 of the present invention was deposited on Feb. 8, 2012 in China General Microbiological Culture Collection Center (CGMCC) with a deposit access number of CGMCC NO. 5744, and the deposit address is Institute of Microbiology of Chinese Academy of Sciences, 3#, Buld. 1, West Beichen Road, Chaoyang District, Beijing, 100101.

Specific Models for Carrying Out the Invention

Some embodiments of the present invention are illustrated in detail in conjunction with the following examples, but those skilled in the art would understand that the following examples are merely intended to illustrate the invention, but should not be deemed as limitation to the scope of the present invention. Those specific techniques or conditions that were not indicated in the examples were carried out according to the techniques or conditions described in the documents in the art (e.g., J. Sambrook, et al., translated by HUANG Peitang, et al, "Molecular Cloning", 3$^{rd}$ Edition, Science Press) or according to specifications of products. Those reagents or instruments of which manufacturers were not given were all conventional products commercially available.

In the following Examples or Comparative Examples, the molecular weight of oligomeric hyaluronate and low-molecular-weight hyaluronate were measured by GPC-MALLS method; the contents were measured by HPLC method or carbazole method. The oligomeric hyaluronic acid or low-molecular-weight hyaluronic acid and the hyaluronic acid as prepared by direct fermentation (structure was not broken) were all consist of N-acetylglucosamine and D-glucuronic acid disaccharide repeating units, so that their contents were equal to their disaccharide contents, the oligomeric hyaluronic acid or low-molecular-weight hyaluronic acid or normal hyaluronic acid could be degraded into disaccharides with bacillus hyaluronidase, the disaccharide contents could be determined by HPLC method so as to obtain the contents of oligomeric hyaluronate or low-molecular-weight hyaluronate. The contents of oligomeric hyaluronate or low-molecular-weight hyaluronate can also be determined by carbazole method (LING Peixue, Hyaluronic Acid [M]. Beijing: China Light Industry Press, 2002). If the structure of hyaluronic acid or salts thereof was broken, hyaluronidase would not crack glucosidic bond of broken parts, so that this would result in the decrease of disaccharide content. The mechanism of carbazole method comprises determining the content of hexuronic acid, then the contents of oligomeric hyaluronic acid or low-molecular-weight hyaluronic acid or hyaluronic acid obtained by direct fermentation could be derived therefrom. Therefore, the difference of contents as measured by these two methods could be used to indirectly observe whether the structure of hyaluronic acid or salts thereof was broken as well as the breakage degree thereof.

The hyaluronidase (i.e., bacillus hyaluronidase, hereinafter) used for degradation of hyaluronic acid or salts thereof in the present invention was obtained by: preparing a hyaluronidase fermentation broth obtained by bacillus A50 fermentation, following steps such as centrifugation, ammonium sulfate fractional precipitation, ultrafiltration, and so on. The preparation process comprised: taking slant strain (Bacillus sp. A50 CGMCC NO. 5744) and inoculating in sterilized seed culture medium, cultured at 25° C.-40° C., 100-200 rpm for 10-24 hours, then inoculating the seed solution into sterilized fermentation culture medium, inoculation amount being 3%-15%, culturing at 25° C.-40° C., 100-300 rpm for 12-24 hours, maintaining pH at 6.0-8.0 during fermentation procedure using an acid, to obtain hyaluronidase fermentation broth after end of the fermentation; centrifuging the fermentation broth under 10000-15000 rpm for 10-20 minutes to obtain supernatant, adding to the supernatant with ammonium sulfate to reach a concentration of 20% w/v-25% w/v, removing the generated precipitate by filtration, then continuously adding ammonium sulfate, until the concentration being 35% w/v-40% w/v, dissolving the obtained precipitate i.e. hyaluronidase in phosphate buffer solution, and finally removing small molecular impurities with $3 \times 10^4$ Da ultrafiltration membrane to obtained hyaluronidase useful in enzymolysis.

The used culture media were:

slant culture medium (100 mL): peptone 0.2-2.0 g, yeast powder 0.2-2.0 g, $K_2HPO_4 \cdot 3H_2O$ 0.05-0.15 g, MgSO$_4$.7H$_2$O 0.05-0.15 g, glucose 0.5-1.5 g, agar powder 2.0 g; pH being adjusted to 6.0-8.0, water, slant culture temperature being 25° C.-40° C.

seed culture medium (100 mL): peptone 0.2-2.0 g, yeast powder 0.2-2.0 g, K$_2$HPO$_4$.3H$_2$O 0.05-0.15 g, MgSO$_4$.7H$_2$O 0.05-0.15 g, glucose 0.5-1.5 g; pH being adjusted to 6.0-8.0.

fermentation culture medium (100 mL): peptone 0.2-2.0 g, yeast powder 0.2-2.0 g, K$_2$HPO$_4$.3H$_2$O 0.05-0.15 g, MgSO$_4$.7H$_2$O 0.05-0.15 g, glucose 0.5-1.5 g, TWEEN 80 0.05 mL; pH being adjusted to 6.0-8.0.

The fermentation broth prepared by the above method was measured by the method of Chinese Pharmacopoeia (see: Chinese Pharmacopoeia, 2010 Edition, Appendix VII. C. Measurement of hyaluronidase) and the hyaluronidase activity thereof was $1\times10^5$-$3\times10^5$ IU/mL, and the specific activity of the purified hyaluronidase was $8\times10^6$-$1.5\times10^7$ IU/mg.

EXAMPLE 1

Acquisition and Identification of *Bacillus* (*Bacillus* sp.) A50

1. Acquisition of *bacillus* (*Bacillus* sp.) A50

Open the cover dish of a petri dish which contains enrichment culture medium, place the dish in air to collect settled bacteria from air, the cover dish was closed after 1 h, the dish was then placed in 25° C.-40° C. incubator for aerobic culture, after 24 hours of culture, the single colony obtained by separation was inoculated in screen culture medium, aerobic culture was performed at 25° C.-40° C., 150 rpm, for 12-16 hours, the hyaluronidase activity thereof was measured by the method of Chinese Pharmacopoeia, the strain with the highest enzyme activity was chosen as the strain of the present invention, and the enzyme activity of the strain could be up to $10^5$ IU/mL.

The compositions of the above used culture media were as follows:

Enrichment culture medium (100 mL): peptone 0.2-2.0 g, yeast powder 0.2-2.0 g, K$_2$HPO$_4$.3H$_2$O 0.05-0.15 g, MgSO$_4$.7H$_2$O 0.05-0.15 g, sodium hyaluronate 0.01-1 g, agar powder 2.0 g.

Screen culture medium (100 mL): peptone 0.2-2.0 g, yeast powder 0.2-2.0 g, K$_2$HPO$_4$.3H$_2$O 0.05-0.15 g, MgSO$_4$.7H$_2$O 0.05-0.15 g, sodium hyaluronate 0.01-1 g.

The obtained *bacillus* (*Bacillus* sp.) A50 was deposited on Feb. 8, 2012 in China General Microbiological Culture Collection Center (CGMCC) with a deposit access number of CGMCC NO. 5744, and the deposit address was Institute of Microbiology of Chinese Academy of Sciences, 3#, Buld. 1, West Beichen Road, Chaoyang District, Beijing, 100101.

2. Morphological Characteristics of *Bacillus* (*Bacillus* sp.) A50

The *bacillus* had rod-like shape, in single or chain form. The bacterial colony was milk white, and had wrinkles.

3. Identification of Molecular Biological Characteristics of *Bacillus* (*Bacillus* sp.) A50

Bacterial 16S rDNA universal primer was synthesized according to Weisburg method:

```
Primer 1:
                              (SEQ ID NO: 4)
5'-AGAGTTTGATCCTGGCTCAG-3';;
```

```
Primer 2:
                              (SEQ ID NO: 5)
5'-GGTTACCTTGTTACGACTT-3'.
```

The total DNA of strain A50 (extracted using column type bacterial DNAout kit of Beijing Tiandz, Inc.) was used as template, its 16S rDNA fragment was amplified, and the PCR amplification reaction system was as follows:

| | |
|---|---|
| 10 × PCR buffer solution | 5.0 µl |
| dNTP (10 mM) | 1.0 µl |
| Primer 1(10 µM) | 1.0 µl |
| Primer 2 (10 µM) | 1.0 µl |
| Taq DNA polymerase (5 U/µL) | 0.5 µl |
| DNA template (50 ng/µL) | 0.5 µl |
| Added with deionized water to total volume | 50 µl |

The PCR reaction conditions were as follows:

| | | |
|---|---|---|
| 95° C. | 5 min | |
| 94° C. | 30 s | |
| 56° C. | 1 min | } 30 cycles |
| 72° C. | 6 min | |
| 72° C. | 10 min | |
| 4° C. | termination of reaction. | |

The PCR product was detected with agarose gel electrophoresis and sequenced (Weisburg W G, Barns S M, Pelletier D A, et al. 16S ribosomal DNA amplification for phylogenetic study [J]. Journal of Bacteriology, 1991, 173 (2): 697-703). The sequence of the obtained 16S rDNA (SEQ ID NO: 1, 1418 bp) was as follows:

```
                                            (SEQ ID NO: 1)
    gcggctggct  ccttacggtt  accccaccga  cttcgggtgt tacaaactct  cgtggtgtga  cgggcggtgt  gtacaaggcc cgggaacgta  ttcaccgcgg  catgctgatc  cgcgattact agcgattccg  gcttcatgca  ggcgagttgc  agcctgcaat ccgaactgag  aatggtttta  tgggattggc  taaacctcgc ggtcttgcag  ccctttgtac  catccattgt  agcacgtgtg tagcccaggt  cataaggggc  atgatgattt  gacgtcatcc ccaccttcct  ccggtttgtc  accggcagtc  accttagagt gcccaactga  atgctggcaa  ctaagatcaa  gggttgcgct cgttgcggga  cttaacccaa  catctcacga  cacgagctga cgacaaccat  gcaccacctg  tcactctgtc  ccccgaaggg gaacgtccta  tctctaggag  tgtcagagga  tgtcaagacc tggtaaggtt  cttcgcgttg  cttcgaatta  aaccacatgc tccaccgctt  gtgcgggccc  ccgtcaattc  ctttgagttt cagccttgcg  gccgtactcc  ccaggcggag  tgcttaatgc gttagctgca  gcactaaagg  gcggaaaccc  tctaacactt agcactcatc  gtttacgcg   tggactacca  gggtatctaa tcctgtttgc  tccccacgct  ttcgcgcctc  agcgtcagtt acagaccaga  aagccgcctt  cgccactggt  gttcctccac
```

-continued

```
atctctacgc atttcaccgc tacacgtgga attccgcttt cctcttctgt actcaagtcc cccagtttcc aatgaccctc cacggttgag ccgtgggctt tcacatcaga cttaaaggac cgcctgcgcg cgctttacgc ccaataattc cggacaacgc ttgccaccta cgtattaccg cggctgctgg cacgtagtta gccgtggctt tctggttagg taccgtcaag gtaccggcag ttactccggt acttgttctt ccctaacaac agagctttac gacccgaagg ccttcatcgc tcacgcggcg ttgctccgtc agactttcgt ccattgcgga agattccta ctgctgcctc ccgtaggagt ctgggccgtg tctcagtccc agtgtggccg atcaccctct caggtcggct acgcatcgtc gccttggtga gccgttacct caccaactag ctaatgcgcc gcgggcccat ctgtaagtgt cagcgtaaac cgactttcag cttttcctca tgagaggaaa aggattatcc ggtattagct ccggtttccc gaagttatcc cagtcttaca ggcaggttgc ccacgtgtta ctcacccgtc cgccgctaac caagaggtgc aagcacctca agattcgctc gacttgca.
```

EXAMPLE 2

Clone and Sequence Analysis of Hyaluronidase

Genomic DNA of the bacillus (Bacillus) A50 was extracted by Bacteria Genomic DNA Extraction Kit, the result of genomic DNA extraction was detected with 1% agarose gel electrophoresis. The genome was sequenced to obtain the whole genome shotgun sequence of the strain. In the meantime, the isolated and purified hyaluronidase from bacillus (Bacillus) A50 fermentation broth was subjected to N-terminal sequencing and internal peptide segment sequencing after trypsin degradation, so as to obtain partial amino acid sequence of the hyaluronidase. The whole genome shotgun sequence and the partial amino acid sequence were blast using BLAST tools of NCBI, so as to find out gene segment with 100% similarity to the amino acid sequence, and thus find rough position of the gene encoding hyaluronidase. Subsequently, based on the N-terminal sequence of hyaluronidase, size of SDS-PAGE electrophoretic bands, and analysis of open reading frame (ORF) with GeneTool software, the specific position and integral nucleotide sequence of target gene were determined, and the nucleotide sequence was translated into amino acid sequence by using BioEdit software.

The amino acid sequence of the hyaluronidase (SEQ ID NO: 2, 1106 aa) was as follows:

```
                                          (SEQ ID NO: 2)
NESTLLLNTSFEETEAPKSGWDQLGAPKWGVWRPTGSPIVTITKEA

SRTGEYGLKIAAAQSARAAVSQDVPVQGGQTYQLGTWLKTDNIVSG

QGARLRVVLYEGTQQLGLLYSSRLTGTHDWSQIKMEVKTPANADSI

RVQLFFETGTGTALFDDVSLQLIQPATSIAIEESEITIKEQETGLL

HAQMVPADASSKVSWVSADPSIATVDNGKVTGVNPGGTTIMAFTDN

GLAATSTVKVIKNDGIERPEVTQLDLQPKELELGSGQVRLLQAIIA

PATADAEKLVWSSSNEAVASIQKGLIEAKASGTAVITVETEDGSLK

SESQITVTDAVVDEYDQLRKKWKSLMTGLDSYDPTNVRMNEMIQNQ

TKSAETLWKTMFKNNDRSFLWINFASTDNSADIRDSYRNLTTMAKA

FANEHSSLYRNPQLLKDITEALEWLYQNRYNESIAQYSNWWHWEIG

VPNELNSLMVLLYDYLDQDSIHRYLKWDHFQPDPTKSGATTPEKYR

EALGANRIDVSKVVGVRGVIVKDATKIAAARDALSQTFENVTEGDG

FYEDGSFVQHENIAYNGSYGIVLIEGLTDMLELLSNSTWQVTDPKV

TNVYDWIETAYEPFMYKGALMDMVRGRAISRNFLQDHQAGHTIIKS

VIRMAQFAPEPYAEKYNSMAKYWLQEDTYLDYFKNAGNFRDITLAK

QLLEKQEVTPRGDLDFHKTFASMDRVVHRKSGYAFGISMYSNRIQN

YEDMNDENRKGWYTGEGMTYLYNGDLAQYSDDFWPTVDPYRMPGTT

VDTMRRADGSGEHRSSESWTGGSTLKNFGSAGMSYDAWNSSLIAKK

SWFMFDNEIVALGAGITSSEDRNVESIVENRKIRNDGSNQLVINGE

TLNLSNGGQNQTMAAKWAFLEGNVPGADIGYYFPEGKMLTIKKEER

TGAWKDINYGGPAEAIKRSYTTMWFDHGVRPEQDTYSYVLLPGLNK

EQTHQYSQNPDITILRNDSAVQAVQDVKENIIGANFWKDEKQSAGP

LTVYQKASVTMQEKDGVLEIAVCDPTMENKGSIEIEIDGKAFKVLE

ADESITVENTKPSIKLKVNVNEAKGKTFTAKLKMIPSQKGNSPNSI

R
```

The nucleotide sequence of the gene encoding hyaluronidase (SEQ ID NO: 3, 3324 bp, encoding 1106 amino acids) was as follows:

```
                                          (SEQ ID NO: 3)
AATGAATCTACTTTACTATTGAATACTAGTTTTGAAGAGACGGAGG

CGCCAAAATCAGGCTGGGATCAATTAGGTGCACCAAAATGGGGTGT

CTGGAGACCTACCGGAAGCCCCATTGTAACCATTACAAAGGAAGCA

AGCCGTACGGGTGAGTATGGTTTAAAAATTGCCGCGGCGCAATCTG

CTAGAGCTGCCGTGTCACAGGATGTACCTGTTCAGGGCGGGCAGAC

CTATCAGTTAGGCACCTGGCTGAAGACAGATAATATCGTCAGCGGT

CAAGGGGCGCGGCTGAGGGTTGTTTTATATGAAGGAACCCAGCAGC

TGGGCTTACTTTACTCTTCAAGATTAACTGGGACCCACGATTGGTC

GCAAATAAAAATGGAGGTAAAGACTCCTGCCAATGCCGATAGCATC

CGTGTCCAGCTTTTCTTTGAAACAGGAACGGGTACAGCCCTATTTG

ATGATGTTTCACTGCAGCTCATCCAGCCAGCTACGTCGATTGCTAT

CGAAGAAAGTGAAATCACCATCAAAGAGCAGGAAACAGGTTTATTG

CATGCACAGATGGTTCCTGCTGATGCCAGCTCCAAAGTATCTTGGG

TGTCGGCGGATCCATCGATTGCCACCGTTGATAACGGTAAGGTTAC

GGGTGTAAATCCCGGGGGGACAACGATTATGGCTTTTACCGATAAC

GGGCTTGCTGCCACTAGTACCGTAAAAGTGATCAAAAATGATGGTA
```

-continued
TTGAACGGCCGGAGGTAACACAGTTGGATCTACAACCAAAGGAACT

CGAGCTTGGATCAGGTCAAGTGCGATTGCTTCAGGCAATTATCGCA

CCAGCCACTGCCGATGCAGAAAAGTTGGTATGGAGCTCTTCCAATG

AAGCAGTCGCTTCTATTCAAAAAGGACTTATTGAAGCGAAAGCCTC

AGGAACTGCTGTGATTACCGTAGAAACGGAAGATGGCAGCTTAAAG

AGTGAAAGCCAGATTACCGTTACCGATGCAGTCGTAGATGAATATG

ATCAACTTCGGAAAAAGTGGAAAAGCCTGATGACTGGTCTTGATTC

GTACGACCCGACGAATGTGCGGATGAACGAAATGATTCAGAACCAG

ACAAAATCAGCGGAAACCCTTTGGAAAACAATGTTTAAAAATAACG

ATCGTTCGTTCTTATGGATTAACTTTGCAAGCACTGACAATTCGGC

TGATATTCGCGACAGCTACCGGAATCTAACGACCATGGCTAAAGCG

TTTGCCAATGAACACTCCAGCCTTTATCGAAATCCGCAATTGCTAA

AGGATATCACGGAGGCGCTAGAGTGGCTGTACCAAAATCGCTATAA

CGAAAGTATTGCTCAATATAGCAATTGGTGGCATTGGGAAATCGGT

GTCCCGAATGAATTAAACAGTTTAATGGTTCTTCTATATGATTATT

TGGATCAAGATAGTATTCATCGCTACTTGAAAGTAGTCGACCACTT

TCAACCAGATCCAACGAAATCCGGAGCCACCACTCCCGAGAAATAC

CGGGAAGCTCTTGGCGCCAATCGGATTGATGTCAGCAAGGTAGTCG

GTGTGCGAGGGGTAATTGTGAAGGACGCCACGAAAATTGCGGCTGC

ACGAGATGCCCTAAGCCAAACTTTTGAAAACGTAACTGAAGGAGAC

GGTTTTTATGAAGATGGCTCCTTCGTTCAGCATGAGAATATCGCCT

ATAACGGGTCATACGGCATTGTCTTAATTGAAGGCTTGACTGACAT

GCTCGAACTCTTAAGTAATTCTACTTGGCAAGTGACTGACCCTAAG

GTTACCAATGTTTATGACTGGATTGAAACTGCCTATGAACCATTTA

TGTATAAAGGTGCTTTGATGGATATGGTGAGAGGAAGAGCGATTTC

ACGTAATTTCCTTCAGGATCATCAGGCTGGACACACCATTATCAAA

AGTGTGATTCGAATGGCACAATTTGCTCCAGAGCCATATGCAGAGA

AGTATAATTCCATGGCAAAATACTGGCTTCAAGAAGATACTTACCT

GGATTATTTTAAAAACGCGGGTAACTTCCGCGATATCACTCTTGCA

AAGCAGCTTTTGGAAAAACAAGAGGTCACCCCTCGCGGAGATCTTG

ATTTTCATAAGACTTTCGCCTCCATGGACCGGGTTGTCCACAGAAA

ATCGGGCTATGCGTTTGGTATCAGTATGTATTCAAACAGGATTCAA

AATTATGAAGACATGAATGATGAAAACCGCAAAGGCTGGTATACCG

GAGAAGGGATGACCTACTTATATAATGGTGACCTCGCTCAATATAG

TGATGATTTCTGGCCGACAGTGGACCCGTACCGGATGCCAGGGACA

ACGGTTGATACGATGAGACGAGCGGATGGAAGTGGTGAGCACAGGT

CGTCAGAGTCATGGACTGGCGGTTCAACCCTAAAGAATTTTGGTTC

TGCAGGAATGTCTTATGATGCTTGGAATAGTTCATTGATTGCCAAA

AAGTCATGGTTTATGTTCGATAACGAAATCGTTGCCCTTGGTGCAG

GGATTACTAGCAGTGAAGACCGGAATGTTGAGAGTATTGTCGAAAA

CCGAAAGATTCGAAATGACGGTTCCAATCAATTGGTCATCAATGGT

-continued
GAAACGCTGAATTTAAGCAATGGTGGTCAAAACCAAACGATGGCCG

CTAAATGGGCTTTTCTTGAAGGGAATGTCCCAGGAGCAGATATTGG

TTACTATTTCCCAGAAGGTAAAATGCTGACGATTAAAAAAGAAGAA

CGTACCGGTGCATGGAAAGATATTAATTATGGCGGTCCAGCTGAAG

CGATCAAGCGATCCTACACAACGATGTGGTTTGACCATGGTGTCCG

TCCTGAGCAGGATACGTACTCCTATGTTCTATTGCCAGGTTTAAAT

AAGGAACAAACACACCAATATTCTCAAAATCCTGATATTACGATTT

TACGAAATGATTCTGCTGTCCAAGCGGTACAAGACGTAAAGGAGAA

TATCATAGGGGCTAATTTCTGGAAGGATGAAAAGCAAAGTGCTGGT

CCGTTAACTGTTTATCAAAAAGCCTCCGTGACCATGCAGGAGAAGG

ATGGAGTCCTTGAGATTGCTGTATGTGATCCGACGATGGAAAACAA

GGGTTCTATCGAAATCGAAATTGATGGCAAGGCGTTCAAGGTTTTA

GAAGCCGATGAAAGTATCACGGTAGAAAATACGAAGCCGTCAATCA

AGTTGAAGGTCAATGTGAATGAGGCAAAAGGGAAAACGTTCACAGC

GAAATTGAAAATGATTCCGAGCCAAAAGGGCAATAGCCCGAACTCA

ATCAGATAATAA

The analysis of amino acid sequence homology based on NCBI/BLAST software showed: the protein having the highest similarity with the amino acid sequence of SEQ ID NO:2 was a xanthan lyase XaIB precursor of a *bacillus* (*Paenibacillus alginolyticus*), the similarity was up to 46%, the proteins with similarity of 31%-46% were mostly hyaluronate lyases, as well as xanthan lyases, polysaccharide lyase-8 family, and some other assumed or unnamed proteins, which all belonged to mucopolysaccharide (GAG) lyase family.

The analysis of gene sequence homology based on NCBI/BLAST software showed: there was no homologous sequence to the nucleotide sequence of SEQ ID NO: 3, which indicated that the gene encoding hyaluronidase with the nucleotide sequence of SEQ ID NO: 3 was a novel gene.

EXAMPLE 3

Preparation of Hyaluronidase (1)

Slant culture medium composition (100 mL): peptone 0.2 g, yeast powder 2.0 g, $K_2HPO_4 \cdot 3H_2O$ 0.05 g, $MgSO_4 \cdot 7H_2O$ 0.05 g, glucose 0.5 g, agar powder 2.0 g; hydrochloric acid being used to adjust pH to 6.0.

Seed culture medium composition (100 mL): peptone 0.2 g, yeast powder 2.0 g, $K_2HPO_4 \cdot 3H_2O$ 0.05 g, $MgSO_4 \cdot 7H_2O$ 0.05 g, glucose 0.5 g; hydrochloric acid being used to adjust pH to 6.0.

Fermentation culture medium composition (100 mL): peptone 0.2 g, yeast powder 2.0 g, $K_2HPO_4 \cdot 3H_2O$ 0.05 g, $MgSO_4 \cdot 7H_2O$ 0.05 g, glucose 0.5 g, TWEEN-80 0.05 mL.

Slant strain (*Bacillus* sp. A50, CGMCC NO. 5744) was inoculated in sterilized seed culture medium, cultured at 25° C., 150 rpm for 24 hours, then the seed solution was inoculated in sterilized fermentation culture medium, inoculation amount being 10%, cultured at 25° C., 200 rpm for 24 hours, sulfuric acid was used during fermentation process to maintain pH at 6.0, hyaluronidase fermentation broth was obtained by fermentation, the fermentation broth was centrifuged under 10000 rpm for 20 minutes to obtain supernatant, the supernatant was added with ammonium sulfate to reach a concentration of 20%, precipitate was removed by filtration, then ammonium sulfate was continuously added until the concentration thereof reached 35%, the obtained precipitate was taken as hyaluronidase, the obtained hyaluronidase precipitate was dissolved in phosphate buffer solution (pH6.0, 50 mmol/L), and finally, small molecular impurities were removed with $3 \times 10^4$ Da ultrafiltration membrane to obtain the purified hyaluronidase.

The hyaluronidase activity in the fermentation broth was $1.0 \times 10^5$ IU/mL, and the specific activity of the purified hyaluronidase was $8.0 \times 10^6$ IU/mg, measured by using the method in Chinese Pharmacopoeia.

EXAMPLE 4

Preparation of Hyaluronidase (2)

Slant culture medium composition (100 mL): peptone 1.0 g, yeast powder 1.0 g, $K_2HPO_4 \cdot 3H_2O$ 0.1 g, $MgSO_4 \cdot 7H_2O$ 0.1 g, glucose 1.0 g, agar powder 2.0 g; phosphoric acid being used to adjust pH to 7.0.

Seed culture medium composition (100 mL): peptone 1.0 g, yeast powder 1.0 g, $K_2HPO_4 \cdot 3H_2O$ 0.1 g, $MgSO_4 \cdot 7H_2O$ 0.1 g, glucose 1.0 g; phosphoric acid being used to adjust pH to 7.0.

Fermentation culture medium composition (100 mL): peptone 1.0 g, yeast powder 1.0 g, $K_2HPO_4 \cdot 3H_2O$ 0.1 g, $MgSO_4 \cdot 7H_2O$ 0.1 g, glucose 1.0 g, TWEEN-80 0.05 mL.

Slant strain (*Bacillus* sp. A50, CGMCC NO. 5744) was taken and inoculated in sterilized seed culture medium, cultured at 30° C., 100 rpm for 15 hours, then the seed solution was inoculated in sterilized fermentation culture medium, inoculation amount being 10%, cultured at 35° C., 300 rpm for 16 hours, sulfuric acid was used during fermentation process to maintain pH at 7.0, hyaluronidase fermentation broth was produced and obtained by fermentation, the fermentation broth was centrifuged under 15000 rpm for 10 minutes to obtain supernatant, the supernatant was added with ammonium sulfate to reach concentration of 22%, precipitate was removed by filtration, then ammonium sulfate was continuously added until its concentration was up to 38%, the obtained hyaluronidase precipitate was dissolved in phosphate buffer solution (pH6.0, 50 mmol/L), and finally small molecular impurities were removed with $3 \times 10^4$ Da ultrafiltration membrane to obtain the purified hyaluronidase.

The hyaluronidase activity in the fermentation broth was $3.0 \times 10^5$ IU/mL, and the specific activity of the purified hyaluronidase was $9.5 \times 10^6$ IU/mg, measured by using the method in Chinese Pharmacopoeia.

EXAMPLE 5

Preparation of Hyaluronidase (3)

Slant culture medium composition (100 mL): peptone 1.5 g, yeast powder 1.5 g, $K_2HPO_4 \cdot 3H_2O$ 0.15 g, $MgSO_4 \cdot 7H_2O$ 0.15 g, glucose 1.5 g, agar powder 2.0 g; sulfuric acid being used to adjust pH to 8.0.

Seed culture medium composition (100 mL): peptone 1.5 g, yeast powder 1.5 g, $K_2HPO_4 \cdot 3H_2O$ 0.15 g, $MgSO_4 \cdot 7H_2O$ 0.15 g, glucose 1.5 g; sulfuric acid being used to adjust pH to 8.0.

Fermentation culture medium composition (100 mL): peptone 0.5 g, yeast powder 1.5 g, $K_2HPO_4 \cdot 3H_2O$ 0.1 g, $MgSO_4 \cdot 7H_2O$ 0.05 g, glucose 1.5 g, Tween-80 0.05 mL.

Slant strain (*bacillus* (*Bacillus* sp.) A50, CGMCC NO. 5744) was taken and inoculated in sterilized seed culture medium, cultured at 35° C., 200 rpm for 13 hours, then the seed solution was inoculated in sterilized fermentation culture medium, inoculation amount being 10%, cultured at 40° C., 100 rpm for 12 hours, hydrochloric acid was used during fermentation to maintain pH at 7.0, the hyaluronidase fermentation broth was obtained by fermentation, the fermentation broth was centrifuged under 12000 rpm for 15 minutes to obtain supernatant, the supernatant was added with ammonium sulfate to reach concentration of 25%, the generated precipitate was removed by filtration, then ammonium sulfate was added continuously until its concentration reached 35%, the obtained hyaluronidase precipitate was taken and dissolved in phosphate buffer solution (pH6.0, 50 mmol/L), and finally small impurities were removed with $3 \times 10^4$ Da ultrafiltration membrane to obtain the purified hyaluronidase.

The hyaluronidase activity in the fermentation broth was $1.2 \times 10^5$ IU/mL, and the specific activity of the purified hyaluronidase was $9.0 \times 10^6$ IU/mg, measured by using the method in Chinese Pharmacopoeia.

EXAMPLE 6

Preparation of Hyaluronidase (4)

Slant culture medium composition (100 mL): peptone 2.0 g, yeast powder 0.5 g, $K_2HPO_4 \cdot 3H_2O$ 0.05 g, $MgSO_4 \cdot 7H_2O$ 0.05 g, glucose 1.0 g, agar powder 2.0 g, sulfuric acid being used to adjust pH to 6.5.

Seed culture medium composition (100 mL): peptone 2.0 g, yeast powder 0.5 g, $K_2HPO_4 \cdot 3H_2O$ 0.05 g, $MgSO_4 \cdot 7H_2O$ 0.05 g, glucose 1.0 g, sulfuric acid being used to adjust pH to 6.5.

Fermentation culture medium composition (100 mL): peptone 1.5 g, yeast powder 0.2 g, $K_2HPO_4 \cdot 3H_2O$ 0.15 g, $MgSO_4 \cdot 7H_2O$ 0.15 g, glucose 1.5 g, TWEEN-80 0.05 mL.

Slant strain (*Bacillus* sp. A50, CGMCC NO. 5744) was taken and inoculated in sterilized seed culture medium, cultured at 40° C., 180 rpm for 10 hours, then the seed solution was inoculated in sterilized fermentation culture medium, inoculation amount being 10%, cultured at 36° C., 280 rpm for 15 hours, phosphoric acid was used during fermentation to maintain pH at 8.0, the hyaluronidase fermentation broth was obtained by fermentation, the fermentation broth was centrifuged under 10000 rpm for 20 minutes to obtain supernatant, the supernatant was added with ammonium sulfate to reach concentration of 20%, the generated precipitate was removed by filtration, the ammonium sulfate was added continuously until its concentration reached 40%, the obtained hyaluronidase was taken and dissolved in phosphate buffer solution (pH6.0, 50 mmol/L), and finally small molecular impurities were removed with $3 \times 10^4$ Da ultrafiltration membrane to obtain the purified hyaluronidase.

The hyaluronidase activity in the fermentation broth was $1.5 \times 10^5$ IU/mL, and the specific activity of the purified hyaluronidase was $8.2 \times 10^6$ IU/mg, measured by using the method in Chinese Pharmacopoeia.

EXAMPLE 7

Preparation of Hyaluronidase (5)

Slant culture medium composition (100 mL): peptone 0.5 g, yeast powder 1.5 g, $K_2HPO_4 \cdot 3H_2O$ 0.15 g, $MgSO_4 \cdot 7H_2O$ 0.1 g, glucose 0.5 g, agar powder 2.0 g; phosphoric acid being used to adjust pH to 7.5.

Seed culture medium composition (100 mL): peptone 0.5 g, yeast powder 1.5 g, $K_2HPO_4·3H_2O$ 0.15 g, $MgSO_4·7H_2O$ 0.1 g, glucose 0.5 g; phosphoric acid being used to adjust pH to 7.5.

Fermentation culture medium composition (100 mL): peptone 2.0 g, yeast powder 0.2 g, $K_2HPO_4·3H_2O$ 0.05 g, $MgSO_4·7H_2O$ 0.05 g, glucose 0.5 g, Tween-80 0.05 mL.

Slant strain (*Bacillus* sp. A50, CGMCC NO. 5744) was taken and inoculated in sterilized seed culture medium, cultured at 36° C., 120 rpm for 14 hours, then the seed solution was inoculated in sterilized fermentation culture medium, inoculation amount being 10%, cultured at 30° C., 180 rpm for 20 hours, phosphoric acid was used during fermentation to maintain pH at 7.5, the hyaluronidase fermentation broth was obtained by fermentation, the fermentation broth was centrifuged under 10000 rpm for 20 minutes to obtain supernatant, the supernatant was added with ammonium sulfate to reach concentration of 25%, the generated precipitate was removed by filtration, then ammonium sulfate was added continuously until its concentration reached 40%, the obtained hyaluronidase precipitate was taken and dissolved in phosphate buffer solution (pH6.0, 50 mmol/L), and finally small impurities were removed with $3\times10^4$ Da ultrafiltration membrane to obtain purified hyaluronidase.

The hyaluronidase activity in the fermentation broth was $2.0\times10^5$ IU/mL, and the specific activity of the purified hyaluronidase was $9.3\times10^6$ IU/mg, measured by using the method in Chinese Pharmacopoeia.

EXAMPLE 8

Preparation of Hyaluronidase (6)

Slant culture medium composition (100 mL): peptone 1.0 g, yeast powder 1.0 g, $K_2HPO_4·3H_2O$ 0.1 g, $MgSO_4·7H_2O$ 0.15 g, glucose 1.5 g, agar powder 2.0 g; hydrochloric acid being used to adjust pH to 7.0.

Seed culture medium composition (100 mL): peptone 1.0 g, yeast powder 1.0 g, $K_2HPO_4·3H_2O$ 0.1 g, $MgSO_4·7H_2O$ 0.15 g, glucose 1.5 g; hydrochloric acid being used to adjust pH to 7.0.

Fermentation culture medium composition (100 mL): peptone 1.5 g, yeast powder 0.5 g, $K_2HPO_4·3H_2O$ 0.05 g, $MgSO_4·7H_2O$ 0.15 g, glucose 1.5 g, TWEEN-80 0.05 mL.

Slant strain (*Bacillus* sp. A50, CGMCC NO. 5744) was taken and inoculated in sterilized seed culture medium, cultured at 32° C., 150 rpm for 18 hours, then the seed solution was inoculated in sterilized fermentation culture medium, inoculation amount being 10%, cultured at 28° C., 200 rpm for 22 hours, hydrochloric acid was used during fermentation to maintain pH at 8.0, the hyaluronidase fermentation broth was obtained by fermentation, the fermentation broth was centrifuged under 15000 rpm for 10 minutes to obtain supernatant, the supernatant was added with ammonium sulfate to reach concentration of 24%, the generated precipitate was removed by filtration, then ammonium sulfate was added continuously until its concentration reached 36%, the obtained hyaluronidase precipitate was taken and dissolved in phosphate buffer solution (pH6.0, 50 mmol/L), and finally small impurities were removed with $3\times10^4$ Da ultrafiltration membrane to obtain the purified hyaluronidase.

The hyaluronidase activity in the fermentation broth was $1.8\times10^5$ IU/mL, and the specific activity of the purified hyaluronidase was $8.4\times10^6$ IU/mg, measured by using the method in Chinese Pharmacopoeia.

EXAMPLE 9

Preparation of Hyaluronidase (7)

Slant culture medium composition (100 mL): peptone 2.0 g, yeast powder 1.5 g, $K_2HPO_4·3H_2O$ 0.05 g, $MgSO_4·7H_2O$ 0.15 g, glucose 0.5 g, agar powder 2.0 g, phosphoric acid being used to adjust pH to 7.0.

Seed culture medium composition (100 mL): peptone 2.0 g, yeast powder 1.5 g, $K_2HPO_4·3H_2O$ 0.05 g, $MgSO_4·7H_2O$ 0.15 g, glucose 0.5 g; phosphoric acid being used to adjust pH to 7.0.

Fermentation culture medium composition (100 mL): peptone 0.5 g, yeast powder 1.5 g, $K_2HPO_4·3H_2O$ 0.15 g, $MgSO_4·7H_2O$ 0.1 g, glucose 1.0 g, Tween-80 0.05 mL.

Slant strain (*Bacillus* sp. A50, CGMCC NO. 5744) was taken and inoculated in sterilized seed culture medium, cultured at 30° C., 200 rpm for 20 hours, then the seed solution was inoculated in sterilized fermentation culture medium, inoculation amount being 10%, cultured at 34° C., 220 rpm for 14 hours, phosphoric acid was used during fermentation to maintain pH at 7.5, the hyaluronidase fermentation broth was obtained by fermentation, the fermentation broth was centrifuged under 12000 rpm for 15 minutes to obtain supernatant, the supernatant was added with ammonium sulfate to reach concentration of 25%, the generated precipitate was removed by filtration, then ammonium sulfate was added continuously until its concentration reached 38%, the obtained hyaluronidase precipitate was taken and dissolved in phosphate buffer solution (pH6.0, 50 mmol/L), and finally small impurities were removed with $3\times10^4$ Da ultrafiltration membrane to obtain the purified hyaluronidase.

The hyaluronidase activity in the fermentation broth was $1.2\times10^5$ IU/mL, and the specific activity of the purified hyaluronidase was $8.1\times10^6$ IU/mg, measured by using the method in Chinese Pharmacopoeia.

EXAMPLE 10

Preparation of Hyaluronidase (8)

The fermentation broth of *Bacillus* sp. A50 (for example, the fermentation broth of any one of Examples 3-9) was centrifuged at 4° C. to remove bacteria, and supernatant was collected. To the supernatant, ammonium sulfate solid powder was added slowly until its concentration was up to 20% w/v, the precipitate was removed by filtration, ammonium sulfate solid powder was continuously added to the filtrate until its concentration was up to 40% w/v, and the precipitate was collected by filtration. The precipitate was dissolved in $Na_2HPO_4$-citric acid buffer solution with pH of 4.5, so as to obtain crude enzyme solution. The crude enzyme solution was loaded to dialysis bag with molecular weight cutoff of $3.0\times10^3$ Da, placed in pH4.5 $Na_2HPO_4$-citric acid buffer solution, and dialyzed at 4° C. overnight. The solution in the dialysis bag was subjected to ion exchange chromatography separation, the chromatographic column packing was DEAE agarose gel FF medium, gradient elution was carried out with 0-0.5M NaCl solution, and elution peaks were collected. The finally collected eluent was subjected to SDS-PAGE electrophoresis to detect effects of separation and purification. The electrophoresis results were shown as lane 1 in FIG. 1: hyaluronidase purity was 97.6%. In the meantime, the finally collected target protease eluent was subjected to vacuum freeze drying to obtain white powder as hyaluronidase. The obtained hyaluronidase has a specific activity of $1.3 \times 10^7$ IU/mg.

EXAMPLE 11

Preparation of Hyaluronidase (9)

The fermentation broth of *Bacillus* sp. A50 (for example, the fermentation broth of any one of Examples 3-9) was centrifuged at 4° C. to remove bacteria, and supernatant was collected. To the supernatant, ammonium sulfate solid powder was added slowly so that its concentration was up to 25% w/v, the precipitate was removed by filtration, ammonium sulfate solid powder was continuously added to the filtrate until its concentration was up to 40% w/v, and the precipitate was collected by filtration. The precipitate was dissolved in 50 mM $Na_2HPO_4$—$NaH_2PO_4$ buffer solution with pH of 6.5, so as to obtain crude enzyme solution. The crude enzyme solution was loaded to dialysis bag with molecular weight cutoff of $1.0 \times 10^4$ Da, placed in 50 mM pH6.5 $Na_2HPO_4$—$NaH_2PO_4$ buffer solution, and dialyzed at 4° C. overnight. The solution in the dialysis bag was subjected to ion exchange chromatography separation, the chromatographic column packing was DEAE agarose gel FF medium, gradient elution was carried out with 0-0.5M NaCl solution, and elution peaks were collected. The finally collected eluent was subjected to SDS-PAGE electrophoresis to detect effects of separation and purification. The electrophoresis results were shown as lane 2 in FIG. 1: hyaluronidase purity was 98.1%. In the meantime, the finally collected target protease eluent was subjected to vacuum freeze drying to obtain white powder as hyaluronidase. The obtained hyaluronidase has a specific activity of $1.4 \times 10^7$ IU/mg.

EXAMPLE 12

Preparation of Hyaluronidase (10)

The fermentation broth of *Bacillus* sp. A50 (for example, the fermentation broth of any one of Examples 3-9) was centrifuged at 4° C. to remove bacteria, and supernatant was collected. To the supernatant, ammonium sulfate solid powder was added slowly so that its concentration was up to 20%, the precipitate was removed by filtration, ammonium sulfate solid powder was continuously added to the filtrate until its concentration was up to 40% w/v, and the precipitate was collected by filtration. The precipitate was dissolved in 50 mM pH8.0 $Na_2HPO_4$—$NaH_2PO_4$ buffer solution, so as to obtain crude enzyme solution. The crude enzyme solution was loaded to dialysis bag with molecular weight cutoff of $1.4 \times 10^4$ Da, placed in 50 mM pH8.0 $Na_2HPO_4$—$NaH_2PO_4$ buffer solution, and dialyzed at 4° C. overnight. The solution in the dialysis bag was subjected to ion exchange chromatography separation, the chromatographic column packing was DEAE agarose gel FF medium, gradient elution was carried out with 0-0.5M NaCl solution, and elution peaks were collected. The finally collected eluent was subjected to SDS-PAGE electrophoresis to detect effects of separation and purification. The electrophoresis results were shown as lane 3 in FIG. 1: hyaluronidase purity was 97.5%. In the meantime, the finally collected target protease eluent was subjected to vacuum freeze drying to obtain white powder as hyaluronidase. The obtained hyaluronidase has a specific activity of $1.5 \times 10^7$ IU/mg.

The hyaluronidase of the present invention has high enzyme activity, good thermal stability and pH stability, can meet the enzyme dosage requirement for industrial degradation of hyaluronic acid in large scale, and the process for preparing the enzyme is simple, with moderate conditions and low cost, and overcome the drawbacks such as environmental pollution of chemical degradation, enzyme source limitation of biological degradation, as well as low activity and high cost.

The following examples illustrated the preparation of oligomeric hyaluronate or low-molecular-weight hyaluronate via enzyme digestion method using the hyaluronidase with enzyme activity of $8 \times 10^6$-$1.5 \times 10^7$ IU/mg of the present invention.

EXAMPLE 13

Preparation of Oligomeric Sodium Hyaluronate

Figure 2A:
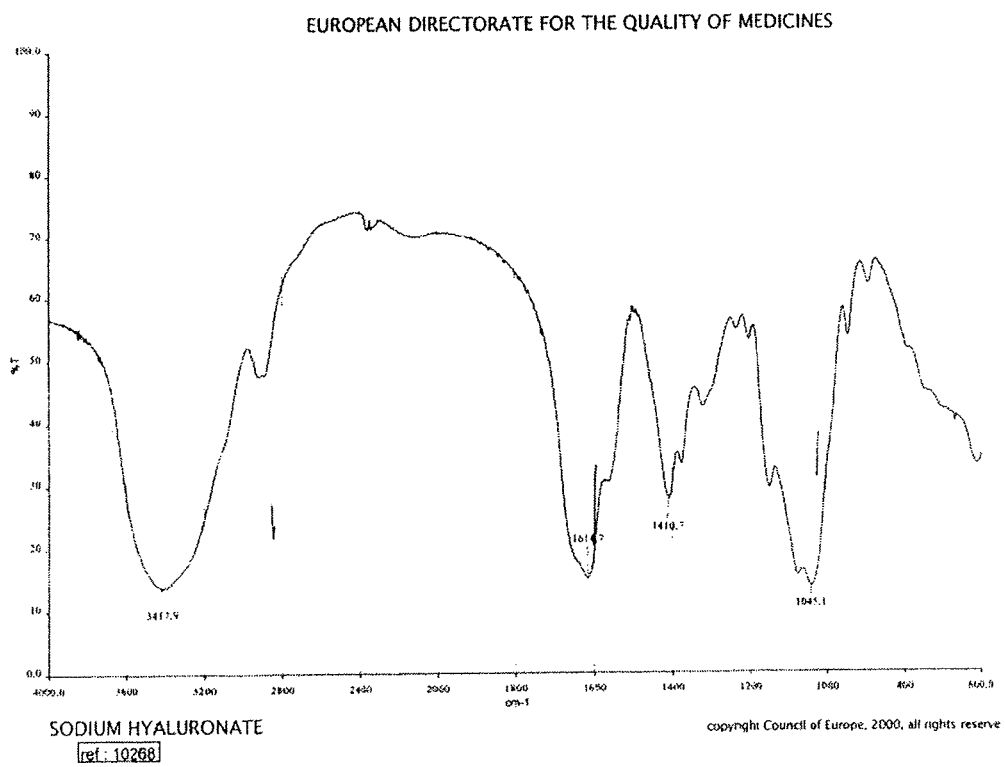
FIG. 2(A) is standard infrared spectrum of sodium hyaluronate according to European Pharmacopoeia.
Figure 2B:
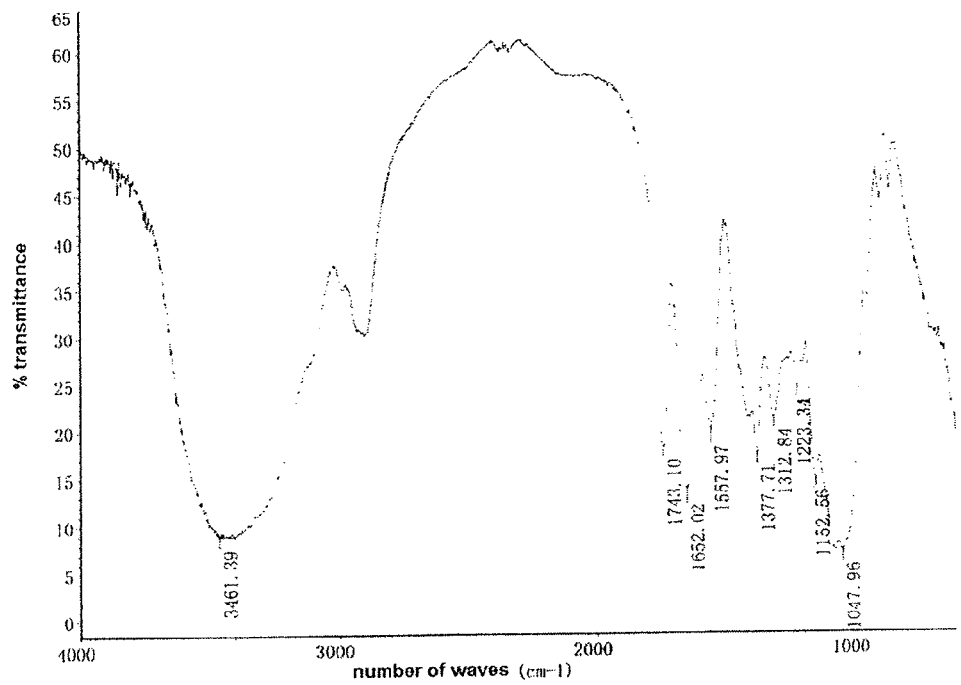
FIG. 2(B) is infrared spectrum of oligomeric hyaluronate prepared in Comparative Example 1.
Figure 2C:
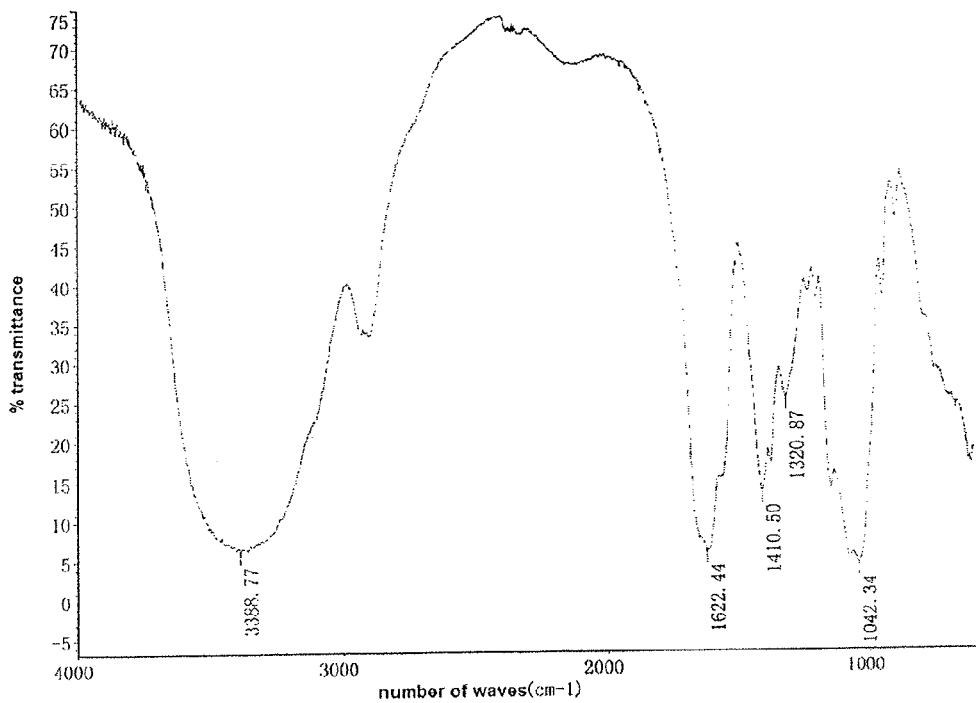
FIG. 2(C) is infrared spectrum of oligomeric hyaluronate prepared in Example 13.
Figure 2D:
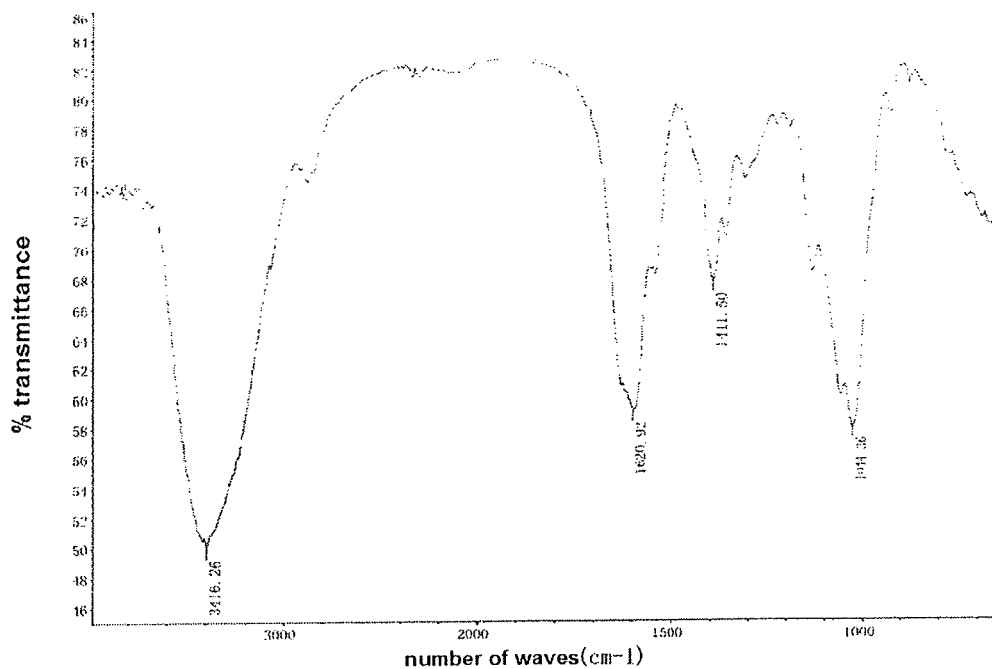
FIG. 2(D) is infrared spectrum of oligomeric hyaluronate prepared in Example 14.

To 1 $m^3$ stain-less steel dissolution tank, 1 $m^3$ of purified water was added, 300 kg of sodium hyaluronate with molecular weight of $2 \times 10^4$ Da was added under stirring to the dissolution tank, after completely dissolved, pH was adjusted to 4.0 with glacial acetic acid, the temperature was elevated to 20° C., $1.35 \times 10^{10}$ IU of *bacillus* hyaluronidase (prepared in Example 3) was added, enzymolysis was continued until molecular weight was less than $10^4$ Da (during the period, continuously sampling and detecting via GPC-MALLS method), the temperature was elevated to 50° C., and kept for 60 minutes, 1 kg of NaCl was added, the enzymolysis solution was filtered with 0.45 μm mixed cellulose filtration membrane, then 20 $m^3$ of ethanol was used for precipitation to obtain sodium hyaluronate precipitate, the precipitate was dehydrated with ethanol, then vacuum dried to obtain oligomeric sodium hyaluronate. The oligomeric sodium hyaluronate was white granules, its content as measured by HPLC method was 96.8%; its content as measured by carbazole method was 97.5%; it had a molecular weight of 8.6 kDa, pH 6.8. Its infrared spectrum was shown in FIG. 2(C), which was in consistent with the standard spectrum of European Pharmacopoeia FIG. 2(A) (the sample of standard spectrum of European Pharmacopoeia was undegraded).

EXAMPLE 14

Preparation of Oligomeric Potassium Hyaluronate

To 1 $m^3$ stain-less steel dissolution tank, 1 $m^3$ of purified water was added, 10 kg of potassium hyaluronate with molecular weight of $3 \times 10^6$ Da was added under stirring to the dissolution tank, after completely dissolved, pH was adjusted to 9.0 with sodium hydroxide, the temperature was elevated to 48° C., $4 \times 10^8$ IU of *bacillus* hyaluronidase (prepared in Example 4) was added, enzymolysis was continued until molecular weight was less than $10^4$ Da, the temperature was elevated to 90° C., and kept for 10 minutes, 100 kg of KCl was added, the enzymolysis solution was filtered with 0.45 μm polysulfone filtration membrane, then 5 $m^3$ of ketone was used for precipitation to obtain potassium hyaluronate precipitate, the precipitate was dehydrated with acetone, then vacuum dried to obtain oligomeric potassium hyaluronate. The oligomeric potassium hyaluronate was white powder, its content as measured by HPLC method was 98.8%; its content as measured by carbazole method was 98.3%; it had a molecular weight of 3.2 kDa, pH 6.5. Its infrared spectrum was shown in FIG. 2(D), which was in consistent with the standard spectrum of European Pharmacopoeia.

EXAMPLE 15

Preparation of Oligomeric Sodium Hyaluronate

Figure 2E:
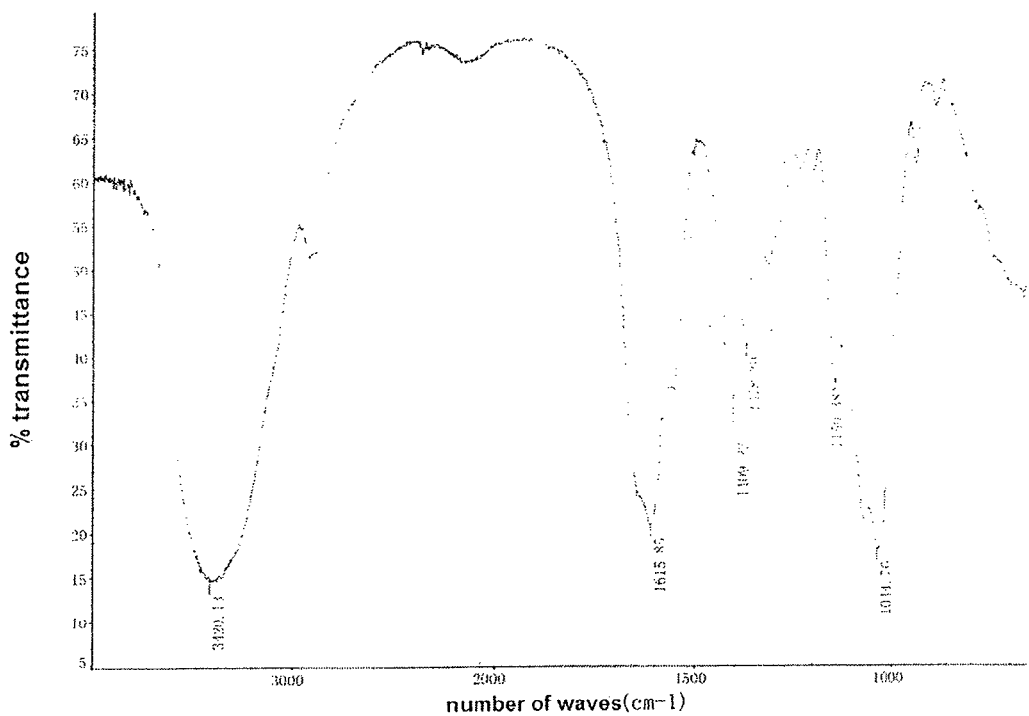
FIG. 2(E) is infrared spectrum of oligomeric hyaluronate prepared in Example 15.

To 1 m$^3$ stain-less steel dissolution tank, 1 m$^3$ of purified water was added, 30 kg of sodium hyaluronate with molecular weight of 1.6×10$^6$ Da was added under stirring to the dissolution tank, after completely dissolved, pH was adjusted to 8.0 with potassium hydroxide, the temperature was elevated to 40° C., 1.2×10$^9$ IU of *bacillus* hyaluronidase (prepared in Example 5) was added, enzymolysis was continued until molecular weight was less than 10$^4$ Da, the temperature was elevated to 60° C., and kept for 60 minutes, 50 kg of NaCl was added, the enzymolysis solution was filtered with 0.45 μm nylon filtration membrane, then 10 m$^3$ of propanol was used for precipitation to obtain sodium hyaluronate precipitate, the precipitate was dehydrated with propanol, then vacuum dried to obtain oligomeric sodium hyaluronate. The oligomeric sodium hyaluronate was white powder, its content as measured by HPLC method was 97.6%; its content as measured by carbazole method was 97.8%; its molecular weight was 6.2 kDa, pH was 7.1. Its infrared spectrum was shown in FIG. 2(E), which was in consistent with the standard spectrum of European Pharmacopoeia.

EXAMPLE 16

Preparation of Oligomeric Calcium Hyaluronate

Figure 2F:
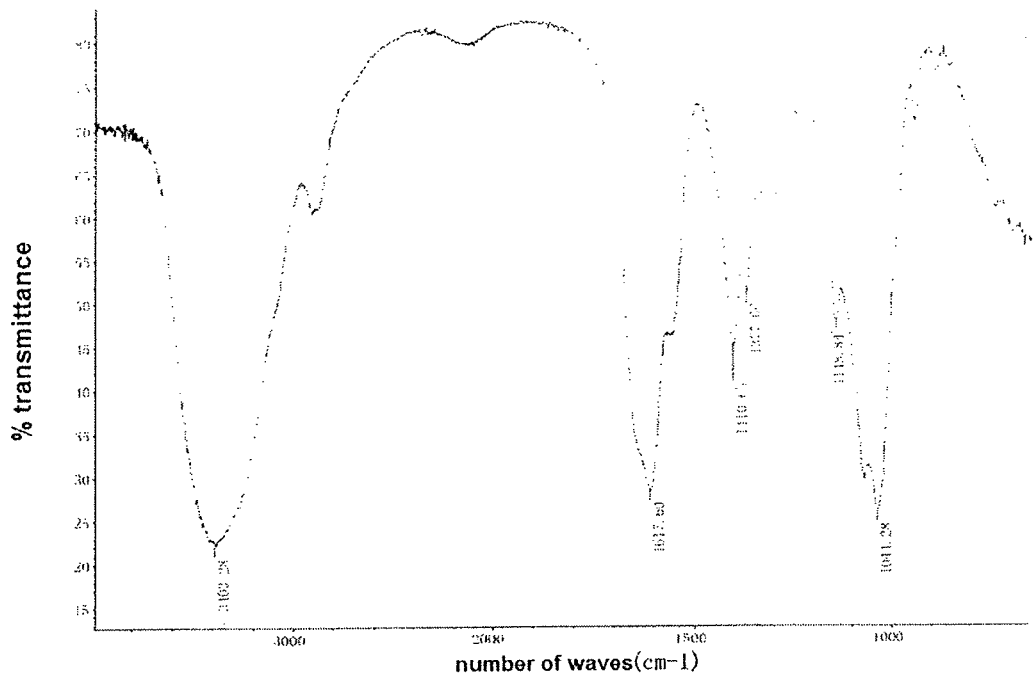
FIG. 2(F) is infrared spectrum of oligomeric hyaluronate prepared in Example 16.

To 1 m$^3$ stain-less steel dissolution tank, 1 m$^3$ of purified water was added, 60 kg of calcium hyaluronate with molecular weight of 8×10$^6$ Da was added under stirring to the dissolution tank, after completely dissolved, pH was adjusted to 7.0 with glacial acetic acid, the temperature was elevated to 35° C., 2.4×10$^9$ IU of *bacillus* hyaluronidase (prepared in Example 6) was added, enzymolysis was continued until molecular weight was less than 10$^4$ Da, the temperature was elevated to 70° C., and kept for 30 minutes, 35 kg of CaCl$_2$ was added, the enzymolysis solution was filtered with 0.45 μm polyether sulfone filtration membrane, then 3 m$^3$ of isopropanol was used for precipitation to obtain calcium hyaluronate precipitate, the precipitate was dehydrated with isopropanol, then vacuum dried to obtain oligomeric calcium hyaluronate. The oligomeric calcium hyaluronate was white powder, its content as measured by HPLC method was 96.6%; its content as measured by carbazole method was 97.3%; its molecular weight was 5.6 kDa, pH was 6.5. Its infrared spectrum was shown in FIG. 2(F), which was in consistent with the standard spectrum of European Pharmacopoeia.

EXAMPLE 17

Preparation of Oligomeric Sodium Hyaluronate

Figure 2G:
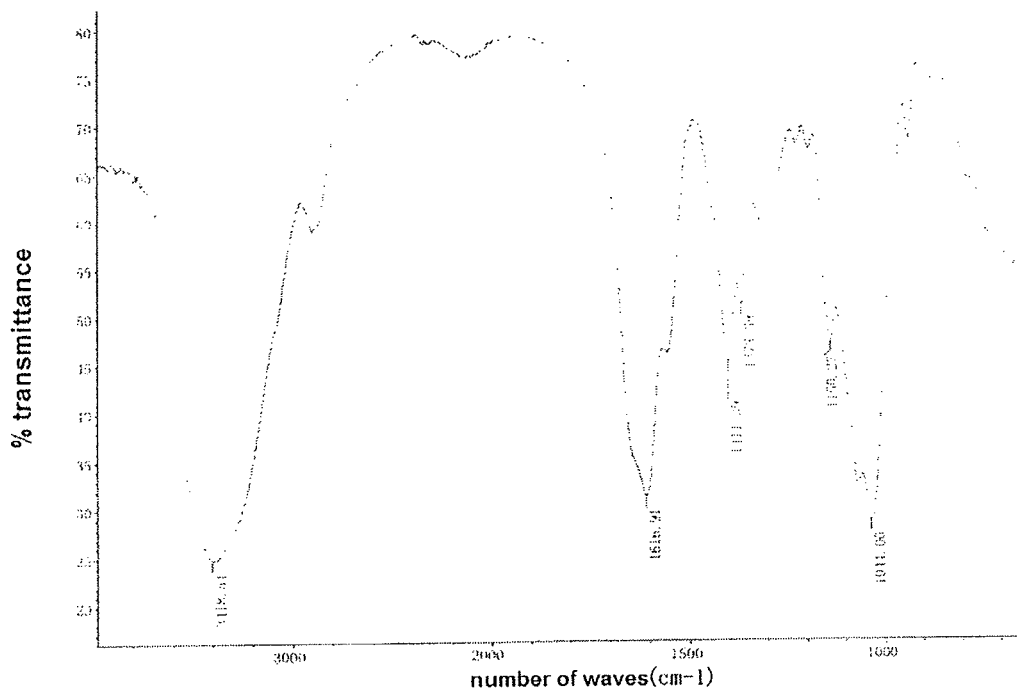
FIG. 2(G) is infrared spectrum of oligomeric hyaluronate prepared in Example 17.

To 1 m$^3$ stain-less steel dissolution tank, 1 m$^3$ of purified water was added, 200 kg of sodium hyaluronate with molecular weight of 2×10$^5$ Da was added under stirring to the dissolution tank, after completely dissolved, pH was adjusted to 6.0 with sulfuric acid, the temperature was elevated to 25° C., 8×10$^9$ IU of *bacillus* hyaluronidase (prepared in Example 7) was added, enzymolysis was continued until molecular weight was less than 10$^4$ Da, the temperature was elevated to 80° C., and kept for 20 minutes, 60 kg of NaCl was added, the enzymolysis solution was filtered with 0.45 μm polyether sulfone filtration membrane, then 6 m$^3$ of methanol was used for precipitation to obtain sodium hyaluronate precipitate, the precipitate was dehydrated with methanol, then vacuum dried to obtain oligomeric sodium hyaluronate. The oligomeric sodium hyaluronate was white powder, its content as measured by HPLC method was 98.7%; its content as measured by carbazole method was 98.3%; its molecular weight was 7.6 kDa, pH was 7.3. Its infrared spectrum was shown in FIG. 2(G), which was in consistent with the standard spectrum of European Pharmacopoeia.

EXAMPLE 18

Preparation of Oligomeric Zinc Hyaluronate

Figure 2H:
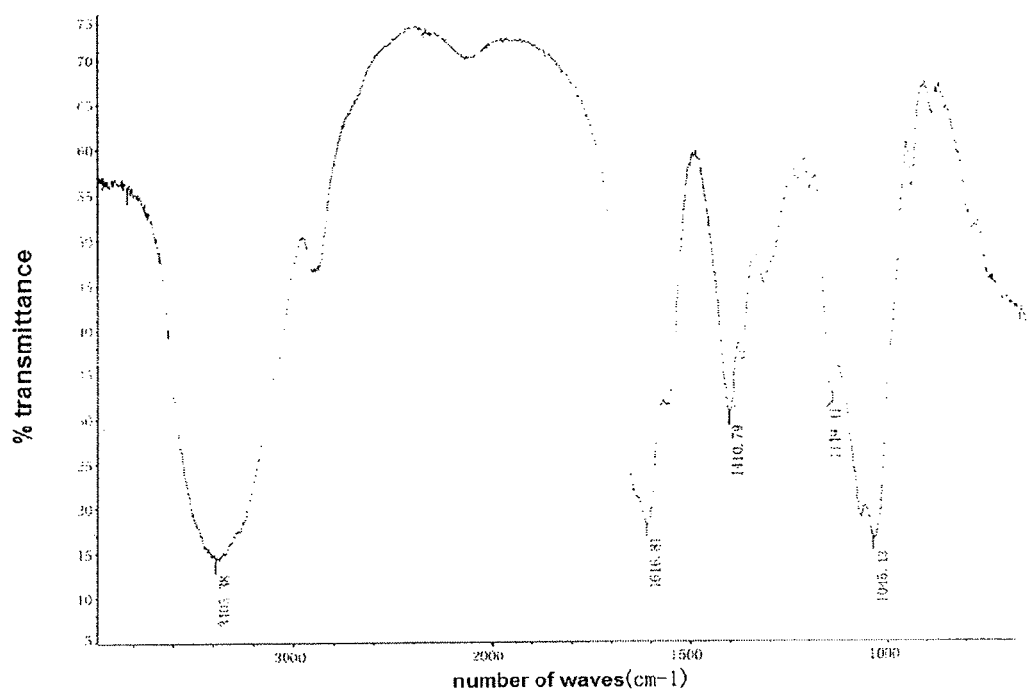
FIG. 2(H) is infrared spectrum of oligomeric hyaluronate prepared in Example 18.

To 1 m$^3$ stain-less steel dissolution tank, 1 m$^3$ of purified water was added, 100 kg of sodium hyaluronate with molecular weight of 10$^5$ Da was added under stirring to the dissolution tank, after completely dissolved, pH was adjusted to 5.0 with sodium hydroxide, the temperature was elevated to 20° C., 4×10$^9$ IU of *bacillus* hyaluronidase (prepared in Example 8) was added, enzymolysis was continued until molecular weight was less than 10$^4$ Da, the temperature was elevated to 55° C., and kept for 40 minutes, 20 kg of ZnCl$_2$ was added, the enzymolysis solution was filtered with 0.45 μm nitrocellulose filtration membrane, then 4.5 m$^3$ of ethanol was used for precipitation to obtain zinc hyaluronate precipitate, the precipitate was dehydrated with ethanol, then vacuum dried to obtain oligomeric zinc hyaluronate. The oligomeric zinc hyaluronate was white powder, its content as measured by HPLC method was 96.8%; its content as measured by carbazole method was 97.6%; its molecular weight was 9.1 kDa, pH was 6.8. Its infrared spectrum was shown in FIG. 2(H), which was in consistent with the standard spectrum of European Pharmacopoeia.

EXAMPLE 19

Preparation of Low-Molecular-Weight Sodium Hyaluronate (1)

To 1 m$^3$ stain-less steel dissolution tank, 1 m$^3$ of purified water was added, 1 kg of sodium hyaluronate with molecular weight of 3×10$^6$ Da was added under stirring to the dissolution tank, after completely dissolved, the temperature was controlled at 48° C., pH was adjusted to 9.0 with sodium hydroxide, 10$^7$ IU of *bacillus* hyaluronidase (prepared in Example 9) was added under stirring for enzymolysis. The enzymolysis was continued until the desired molecular weight was achieved; the temperature was elevated to 50° C., and kept for 60 minutes. 2 kg of NaCl was added, filtration was performed with 0.45 μm polypropylene filtration core after completely dissolved, then 1 m$^3$ of acetone was used for precipitation to obtain low-molecular-weight sodium hyaluronate precipitate, the precipitate was dehydrated with acetone, then vacuum dried to obtain low-molecular-weight sodium hyaluronate. The low-molecular-weight sodium hyaluronate was white powder, its content as measured by HPLC method was 98.3%; its content as measured by carbazole method was 98.5%; and its molecular weight was 931 kDa.

EXAMPLE 20

Preparation of Low-Molecular-Weight Potassium Hyaluronate

To 1 m$^3$ stain-less steel dissolution tank, 1 m$^3$ of purified water was added, 20 kg of potassium hyaluronate with molecular weight of 1×10$^6$ Da was added under stirring to the dissolution tank, after completely dissolved, the temperature was controlled at 20° C., pH was adjusted to 4.0 with glacial acetic acid, 10$^8$ IU of *bacillus* hyaluronidase (prepared in Example 7) was added under stirring for enzymolysis. The enzymolysis was continued until the desired molecular weight was achieved; the temperature was elevated to 90° C., and kept for 10 minutes. 100 kg of KCl was added, filtration was performed with 0.45 µm nitrocellulose filtration core after completely dissolved, then 10 m$^3$ of ethanol was used for precipitation to obtain low-molecular-weight potassium hyaluronate precipitate, the precipitate was dehydrated with ethanol, then vacuum dried to obtain low-molecular-weight potassium hyaluronate. The low-molecular-weight potassium hyaluronate was white powder, its content as measured by HPLC method was 96.8%; its content as measured by carbazole method was 97.5%; and its molecular weight was 15 kDa.

EXAMPLE 21

Preparation of Low-Molecular-Weight Zinc Hyaluronate

To 1 m$^3$ stain-less steel dissolution tank, 1 m$^3$ of purified water was added, 12 kg of sodium hyaluronate with molecular weight of 1.61×10$^6$ Da was added under stirring to the dissolution tank, after completely dissolved, the temperature was controlled at 45° C., pH was adjusted to 5.0 with glacial acetic acid, 2×10$^7$ IU of *bacillus* hyaluronidase (prepared in Example 8) was added under stirring for enzymolysis. The enzymolysis was continued until the desired molecular weight was achieved; the temperature was elevated to 80° C., and kept for 20 minutes. 40 kg of ZnCl$_2$ was added, filtration was performed with 0.45 µm polyether sulfone filtration core after completely dissolved, then 3 m$^3$ of methanol was used for precipitation to obtain low-molecular-weight zinc hyaluronate precipitate, the precipitate was dehydrated with methanol, then vacuum dried to obtain low-molecular-weight zinc hyaluronate. The low-molecular-weight zinc hyaluronate was white powder, its content as measured by HPLC method was 98.5%; its content as measured by carbazole method was 98.2%; and its molecular weight was 754 kDa.

EXAMPLE 22

Preparation of Low-Molecular-Weight Potassium Hyaluronate

To 1 m$^3$ stain-less steel dissolution tank, 1 m$^3$ of purified water was added, 10 kg of potassium hyaluronate with molecular weight of 1.77×10$^6$ Da was added under stirring to the dissolution tank, after completely dissolved, the temperature was controlled at 38° C., pH was adjusted to 6.0 with phosphoric acid, 5×10$^7$ IU of *bacillus* hyaluronidase (prepared in Example 9) was added under stirring for enzymolysis. The enzymolysis was continued until the desired molecular weight was achieved; the temperature was elevated to 60° C., and kept for 30 minutes. 30 kg of K$_2$SO$_4$ was added, filtration was performed with 0.45 µm polyether sulfone filtration core after completely dissolved, then 5 m$^3$ of isopropanol was used for precipitation to obtain low-molecular-weight potassium hyaluronate precipitate, the precipitate was dehydrated with isopropanol, then vacuum dried to obtain low-molecular-weight potassium hyaluronate. The low-molecular-weight potassium hyaluronate was white powder, its content as measured by HPLC method was 96.3%; its content as measured by carbazole method was 97.3%; and its molecular weight was 421 kDa.

EXAMPLE 23

Preparation of Low-Molecular-Weight Magnesium Hyaluronate

To 1 m$^3$ stain-less steel dissolution tank, 1 m$^3$ of purified water was added, 8 kg of magnesium hyaluronate with molecular weight of 2.55×10$^6$ Da was added under stirring to the dissolution tank, after completely dissolved, the temperature was controlled at 42° C., pH was adjusted to 5.5 with sulfuric acid, 3×10$^7$ IU of *bacillus* hyaluronidase (prepared in Example 6) was added under stirring for enzymolysis. The enzymolysis was continued until the desired molecular weight was achieved; the temperature was elevated to 55° C., and kept for 50 minutes. 60 kg of MgCl$_2$ was added, filtration was performed with 0.45 µm polypropylene filtration core after completely dissolved, then 2.5 m$^3$ of propanol was used for precipitation to obtain low-molecular-weight magnesium hyaluronate precipitate, the precipitate was dehydrated with propanol, then vacuum dried to obtain low-molecular-weight magnesium hyaluronate. The low-molecular-weight magnesium hyaluronate was white powder, its content as measured by HPLC method was 97.2%; its content as measured by carbazole method was 98.1%; and its molecular weight was 538 kDa.

EXAMPLE 24

Preparation of Low-Molecular-Weight Calcium Hyaluronate

To 1 m$^3$ stain-less steel dissolution tank, 1 m$^3$ of purified water was added, 5 kg of calcium hyaluronate with molecular weight of 2.46×10$^6$ Da was added under stirring to the dissolution tank, after completely dissolved, the temperature was controlled at 40° C., pH was adjusted to 7.0 with glacial acetic acid, 5×10$^7$ IU of *bacillus* hyaluronidase (prepared in Example 5) was added under stirring for enzymolysis. The enzymolysis was continued until the desired molecular weight was achieved; the temperature was elevated to 65° C., and kept for 40 minutes. 50 kg of CaCl$_2$ was added, filtration was performed with 0.45 µm polypropylene filtration core after completely dissolved, then 4.5 m$^3$ of acetone was used for precipitation to obtain low-molecular-weight calcium hyaluronate precipitate, the precipitate was dehydrated with acetone, then vacuum dried to obtain low-molecular-weight calcium hyaluronate. The low-molecular-weight calcium hyaluronate was white powder, its content as measured by HPLC method was 98.1%; its content as measured by carbazole method was 98.2%; and its molecular weight was 205 kDa.

EXAMPLE 25

Preparation of Low-Molecular-Weight Sodium Hyaluronate

To 1 m$^3$ stain-less steel dissolution tank, 1 m$^3$ of purified water was added, 2 kg of sodium hyaluronate with molecular weight of 2.78×10⁶ Da was added under stirring to the dissolution tank, after completely dissolved, the temperature was controlled at 35° C., pH was adjusted to 6.5 with glacial acetic acid, 2×10⁷ IU of *bacillus* hyaluronidase (prepared in Example 4) was added under stirring for enzymolysis. The enzymolysis was continued until the desired molecular weight was achieved; the temperature was elevated to 58° C., and kept for 50 minutes. 70 kg of $Na_2SO_4$ was added, filtration was performed with 0.45 μm nitrocellulose filtration core after completely dissolved, then 4.8 m³ of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight_sodium hyaluronate was white powder, its content as measured by HPLC method was 98.6%; its content as measured by carbazole method was 98.3%; and its molecular weight was 332 kDa.

EXAMPLE 26

Preparation of Low-Molecular-Weight Sodium Hyaluronate

To 1 m³ stain-less steel dissolution tank, 1 m³ of purified water was added, 15 kg of sodium hyaluronate with molecular weight of 1.41×10⁶ Da was added under stirring to the dissolution tank, after completely dissolved, the temperature was controlled at 43° C., pH was adjusted to 8.0 with sodium hydroxide, 4×10⁷ IU of *bacillus* hyaluronidase (prepared in Example 3) was added under stirring for enzymolysis. The enzymolysis was continued until the desired molecular weight was achieved; the temperature was elevated to 65° C., and kept for 40 minutes. 80 kg of NaCl was added, filtration was performed with 0.45 μm polysulfone filtration core after completely dissolved, then 8 m³ of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight_sodium hyaluronate was white powder, its content as measured by HPLC method was 98.2%; its content as measured by carbazole method was 99.1%; and its molecular weight was 38 kDa.

EXAMPLE 27

Use of Hyaluronidase in Preparation of Low-Molecular-Weight Chondroitin Sulfate

In 1 m³ stain-less steel dissolution tank, 1 m³ of pH 6.0 phosphate buffer solution was prepared, 50 kg of chondroitin sulfate with molecular weight of 5×10⁴ Da was added under stirring to the dissolution tank, after completely dissolved, the temperature was controlled at 37° C., 9×10⁸ IU of *bacillus* hyaluronidase (for example, the hyaluronidase as prepared in any one of Examples 3-9) was added, the enzymolysis was continued until the molecular weight was 5000 Da, the temperature was elevated to 50° C., and kept for 60 minutes, the enzymolysis solution was filtered with 0.45 μm filtration core, then 20 m³ of ethanol was used for precipitation to obtain low-molecular-weight chondroitin sulfate precipitate, the precipitate was dehydrated with ethanol, then vacuum dried to obtain low-molecular-weight chondroitin sulfate. The low-molecular-weight chondroitin sulfate was white powder, its content was 95.8%; its molecular weight was 5.1 kDa; and its pH was 6.8.

COMPARATIVE EXAMPLE 1

Preparation of Oligomeric Sodium Hyaluronate by Chemical Degradation Method (1)

To 1 L beaker, 1 L of purified water was added, 50 g of sodium hyaluronate with molecular weight of 8×10⁵ Da was added under stirring to the beaker, after completely dissolved, 10 mL of concentrated hydrochloric acid was added, when degradation was processed until the molecular weight was less than 10⁴ Da, pH was adjusted to 6.2 with sodium hydroxide, the degradation solution was filtered with 0.45 μm mixed cellulose filtration membrane, then 10 L of ethanol was used for precipitation to obtain sodium hyaluronate precipitate, the precipitate was dehydrated with ethanol, then vacuum dried to obtain oligomeric sodium hyaluronate. The oligomeric sodium hyaluronate was light yellow powder, its content as measured by HPLC method was 63.8%; its content as measured by carbazole method was 98.9%; its molecular weight was 8.1 kDa, pH was 4.8. Its infrared spectrum was shown in FIG. 2(B), which was not in consistent with the standard spectrum of European Pharmacopoeia.

COMPARATIVE EXAMPLE 2

Preparation of Oligomeric Sodium Hyaluronate by Chemical Degradation Method (2)

To 1 L beaker, 1 L of purified water was added, 100 g of sodium hyaluronate with molecular weight of 5×10⁵ Da was added under stirring to the beaker, after completely dissolved, 10 mL of concentrated hydrochloric acid was added, when degradation was processed until the molecular weight was less than 10⁴ Da, pH was adjusted to 6.5 with sodium hydroxide, the degradation solution was filtered with 0.45 μm polysulfone filtration membrane, then 10 L of ethanol was used for precipitation to obtain sodium hyaluronate precipitate, the precipitate was dehydrated with ethanol, then vacuum dried to obtain oligomeric sodium hyaluronate. The oligomeric sodium hyaluronate was light yellow powder, its content as measured by HPLC method was 60.2%; its content as measured by carbazole method was 99.2%; its molecular weight was 7.6 kDa, pH was 4.2.

COMPARATIVE EXAMPLE 3

Preparation of Low-Molecular-Weight Sodium Hyaluronate by Chemical Degradation Method (1)

To 1 L beaker, 1 L of purified water was added, 10 g of sodium hyaluronate with molecular weight of 1×10⁶ Da was added under stirring to the beaker, after completely dissolved, 5 g of sodium hydroxide was added, the temperature was elevated to 65° C., when degradation was processed until the desired molecular weight was achieved, pH was adjusted to 6.5 with glacial acetic acid, the degradation solution was filtered with 0.45 μm polysulfone filtration membrane, then 5 L of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight sodium hyaluronate was light yellow powder, its content as measured by HPLC method was 68.2%; its content as measured by carbazole method was 97.5%; its molecular weight was 15 kDa, pH was 6.9.

COMPARATIVE EXAMPLE 4

Preparation of Low-Molecular-Weight Sodium Hyaluronate by Chemical Degradation Method (2)

To 1 L beaker, 1 L of purified water was added, 15 g of sodium hyaluronate with molecular weight of $1.41 \times 10^6$ Da was added under stirring to the beaker, after completely dissolved, 6 g of sodium hydroxide was added, the temperature was elevated to 65° C., when degradation was processed until the desired molecular weight was achieved, pH was adjusted to 6.2 with hydrochloric acid, the degradation solution was filtered with 0.45 μm polysulfone filtration membrane, then 4 L of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight sodium hyaluronate was light yellow powder, its content as measured by HPLC method was 70.5%; its content as measured by carbazole method was 96.8%; its molecular weight was 39.2 kDa, pH was 6.4.

COMPARATIVE EXAMPLE 5

Preparation of Low-Molecular-Weight Sodium Hyaluronate by Chemical Degradation Method (3)

To 1 L beaker, 1 L of purified water was added, 8 g of sodium hyaluronate with molecular weight of $1.61 \times 10^6$ Da was added under stirring to the beaker, after completely dissolved, 6 g of sodium hydroxide was added, the temperature was elevated to 60° C., when degradation was processed until the desired molecular weight was achieved, pH was adjusted to 6.8 with glacial acetic acid, the degradation solution was filtered with 0.45 μm polysulfone filtration membrane, then 4 L of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight sodium hyaluronate was light yellow powder, its content as measured by HPLC method was 73.2%; its content as measured by carbazole method was 98.5%; its molecular weight was 330 kDa, pH was 6.2.

COMPARATIVE EXAMPLE 6

Preparation of Low-Molecular-Weight Sodium Hyaluronate by Chemical Degradation Method (4)

To 1 L beaker, 1 L of purified water was added, 5 g of sodium hyaluronate with molecular weight of $2.25 \times 10^6$ Da was added under stirring to the beaker, after completely dissolved, 5 g of sodium hydroxide was added, the temperature was elevated to 60° C., when degradation was processed until the desired molecular weight was achieved, pH was adjusted to 6.6 with glacial acetic acid, the degradation solution was filtered with 0.45 μm polysulfone filtration membrane, then 2 L of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight sodium hyaluronate was light yellow powder, its content as measured by HPLC method was 89.9%; its content as measured by carbazole method was 96.8%; its molecular weight was 530 kDa, pH was 7.5.

COMPARATIVE EXAMPLE 7

Preparation of Low-Molecular-Weight Sodium Hyaluronate by Chemical Degradation Method (5)

To 1 L beaker, 1 L of purified water was added, 4 g of sodium hyaluronate with molecular weight of $2.46 \times 10^6$ Da was added under stirring to the beaker, after completely dissolved, 4 g of sodium hydroxide was added, the temperature was elevated to 60° C., when degradation was processed until the desired molecular weight was achieved, pH was adjusted to 6.2 with hydrochloric acid, the degradation solution was filtered with 0.45 μm polysulfone filtration membrane, then 3 L of ethanol was used for precipitation to obtain low-molecular-weight sodium hyaluronate precipitate, the precipitate was dehydrated with ethanol, then vacuum dried to obtain low-molecular-weight sodium hyaluronate. The low-molecular-weight sodium hyaluronate was light yellow powder, its content as measured by HPLC method was 95.8%; its content as measured by carbazole method was 98.5%; its molecular weight was 770 kDa, pH was 7.6.

EXPERIMENTAL EXAMPLE 1

Comparison of Structure of Oligomeric Hyaluronates as Prepared by Enzymolysis (Enzyme Digestion) and by Chemical Degradation All of oligomeric hyaluronic acid or low-molecular-weight hyaluronic acid as well as normal hyaluronic acid consist of N-acetylglucosamine and D-glucuronic acid disaccharide repeating units, so that their contents were equal to their disaccharide contents, the oligomeric hyaluronic acid or low-molecular-weight hyaluronic acid or normal hyaluronic acid could be degraded into disaccharides with *bacillus* hyaluronidase, the disaccharide contents could be determined by HPLC method so as to obtain the contents of oligomeric hyaluronate or low-molecular-weight hyaluronate. In the meantime, the contents of oligomeric hyaluronate or low-molecular-weight hyaluronate were also determined by carbazole method. If the structure of hyaluronic acid or salts thereof was broken, hyaluronidase would not crack glucosidic bond of the broken parts, so that this would result in the decrease of disaccharide content. The greater the difference of the measured values between HPLC method and carbazole method, the greater the broken parts of oligomeric hyaluronate or low-molecular-weight hyaluronate.

Specific method can also be read in China Patent Application with publication number of CN102323344A, which all contents are incorporated into the present invention by reference.

For example, the HPLC could be performed by the following steps:

a. standard control solution: an amount of standard control (Hyaluronic acid disaccharide ΔDiHA sodium salt, H9649, Sigma) was weighed, dissolved with phosphate buffer solution (pH6.0, 5 mmol/L) to formulate 1 mg/mL solution, and thus obtaining standard control solution;

b. sample pretreatment: an amount of sample to be tested (prepared by Comparative Examples 1-7, Examples 13-26) was weighed, dissolved with phosphate buffer solution (pH6.0, 5 mmol/L) to formulate 1 mg/mL solution. 1 mL of sample solution was added with 1000 IU of hyaluronidase (can be prepared by Examples 10-12), subjected to 42° C. water bath for 2 hours; after enzymolysis, the enzymolysis solution was boiled for 2 minutes to inactivate the enzyme, and thus obtained sample enzymolysis solution.

The sample enzymolysis solution was transferred to a 20 mL volumetric flask, added with mobile phase to the scale, mixed uniformly, and filtered to obtain a solution to be tested.

c. treatment of standard control solution; 1 mL of standard control solution was diluted with mobile phase by 20 times, and filtered for standby use.

d. chromatography conditions: saccharide analysis column was used to perform high performance liquid chromatography measurement; mobile phase was 0.4 mol/L $NaH_2PO_4$ solution; flow rate was 0.6 ml/min; column temperature was 35° C.; detection wavelength was 232 nm; sample size was 20 μL;

e. result calculation: high performance liquid chromatography was used to perform chromatography separation of standard control and sample to be tested, respectively, and hyaluronic acid disaccharide peak area was calculated by external standard method; specifically, the following formula was used to calculate the content of oligomeric hyaluronic acid or salts thereof:

The content of hyaluronate:

$$C(\%) = \frac{A_X \times C_R \times 100}{A_R \times W_X \times (100 - h)} \times 100\%$$

$A_X$: peak area of hyaluronic acid disaccharide of the sample to be tested;

$A_R$: peak area of hyaluronic acid disaccharide of the standard control;

Wx: amount of the sample to be tested, mg;

$C_R$: concentration of the standard control solution, mg/mL;

h(%) is drying loss of the sample to be tested.

The comparison of contents of oligomeric hyaluronates obtained in Comparative Example 1-2 and Example 13-18 were shown in Table 1.

TABLE 1

Contents of oligomeric hyaluronates

| | Comparative Example | | Example | | | | | |
|---|---|---|---|---|---|---|---|---|
| | 1 | 2 | 13 | 14 | 15 | 16 | 17 | 18 |
| Content (HPLC method, %) | 63.8 | 60.2 | 96.8 | 98.8 | 97.6 | 96.6 | 98.7 | 96.8 |
| Content (carbazole method, %) | 98.9 | 99.2 | 97.5 | 98.3 | 97.8 | 97.3 | 98.3 | 97.6 |
| Content difference (%) | 35.1 | 39 | 0.7 | 0.5 | 0.2 | 0.7 | 0.4 | 0.8 |

It can be seen in Table 1 that there are relatively great differences of contents of oligomeric hyaluronates prepared via chemical degradation method as measured by HPLC method and carbazole method, while there are no significant differences of contents of oligomeric hyaluronates prepared via enzymolysis method as measured by HPLC method and carbazole method, that is, they are all smaller than 1%. This indicates that the oligomeric hyaluronates prepared by enzymolysis method have integral structure, while the structure of hyaluronates prepared by chemical degradation method has been broken to a relative great extent.

In the meantime, the infrared spectra show that the oligomeric hyaluronate prepared by enzyme digestion method are in consistent with the standard spectrum of European Pharmacopoeia, while the oligomeric hyaluronates prepared by chemical degradation method are significantly different from the standard spectrum of European Pharmacopoeia at wave number around 1610 $cm^{-1}$, which indicates that the structure of the oligomeric hyaluronates prepared by chemical degradation method are broken, while the oligomeric hyaluronates prepared by enzyme digestion method are integral.

EXPERIMENTAL EXAMPLE 2

Comparison of Structure of Low-Molecular-Weight Hyaluronates as Prepared by Enzymolysis (Enzyme Digestion) and by Chemical Degradation The comparison of contents of low-molecular-weight hyaluronates obtained in Comparative Example 3-7 and Example 19-26 were shown in Tables 2-3.

Specific steps referred to Experimental Example 1.

TABLE 2

Contents of low-molecular-weight hyaluronates (Comparative Example 3-7)

| Comparative Example | 3 | 4 | 5 | 6 | 7 |
|---|---|---|---|---|---|
| Molecular weight (KDa) | 15 | 39.2 | 330 | 530 | 770 |
| Content (HPLC method, %) | 68.2 | 70.5 | 73.2 | 89.9 | 95.8 |
| Content (carbazole method, %) | 97.5 | 96.8 | 98.5 | 96.8 | 98.5 |
| Difference (%) | 29.3 | 26.3 | 25.3 | 6.9 | 2.7 |

TABLE 3

Contents of low-molecular-weight hyaluronates (Example 19-26)

| Example | 20 | 26 | 24 | 25 | 22 | 23 | 21 | 19 |
|---|---|---|---|---|---|---|---|---|
| Molecular weight (KDa) | 15 | 38 | 205 | 332 | 421 | 538 | 754 | 931 |
| Content (HPLC method, %) | 96.8 | 98.2 | 98.1 | 98.6 | 96.3 | 97.2 | 98.5 | 98.3 |
| Content (carbazole method, %) | 97.5 | 99.1 | 98.2 | 98.3 | 97.3 | 98.1 | 98.2 | 98.5 |
| Difference (%) | 0.7 | 0.9 | 0.1 | 0.3 | 1.0 | 0.9 | 0.3 | 0.2 |

It can be seen from Tables 2 and 3 that when the molecular weight of low-molecular-weight hyaluronate prepared by chemical degradation method was lower than 770,000, the difference of contents as measured by two methods increased with the decrease of molecular weight; while the difference of contents as measured by two methods was always very small when the molecular weight of low-molecular-weight hyaluronate prepared by enzymolysis method changed, that was, all less than 1%. This phenomenon shows the structure of low-molecular-weight hyaluronic acid prepared by enzymolysis method is integral; while when the molecular weight of low-molecular-weight hyaluronic acid prepared by chemical degradation method was less than 770,000, the lower the molecular weight, the greater extent of damage of structure.

The oligomeric hyaluronate obtained by animal enzyme degradation has biological activities such as promoting angiogenesis, promoting wound healing, combating tumors and regulating immune. The biological activities of oligomeric hyaluronate obtained by microbe-sourced hyaluronidase degradation have not been reported. However, the following experimental researches show that the oligomeric hyaluronates obtained in the present invention are free of cytotoxicity, and in comparison with the oligomeric hyaluronate obtained by chemical degradation method, they have potent effects in scavenging free radicals, potent reduction ability, potent effects in sun protection and post-sunburn repairing, and thus can be used in cosmetics; the oligomeric hyaluronates have small molecular weight, and are prone to intestinal absorption, thus can be used in foods; in the meantime, the oligomeric hyaluronates have functions in promoting angiogenesis and promoting wound healing, thus can be used in the field of medicines.

The biological activities of low-molecular-weight hyaluronate obtained by microbe-sourced hyaluronidase degradation have not been reported, either. However, the above Examples 19-26 show that the low-molecular-weight hyaluronates prepared by enzyme digestion have integral structure, and the following experimental researchers show that the low-molecular-weight hyaluronates obtained in the present invention have potent effects in scavenging free radicals, potent reduction ability, potent effects in sun protection and post-sunburn repairing, and thus can be used in cosmetics and medicines; and the low-molecular-weight hyaluronates can also be used in foods, to maintain lubricity and elasticity of skin.

EXPERIMENTAL EXAMPLE 3

Figure 3A:
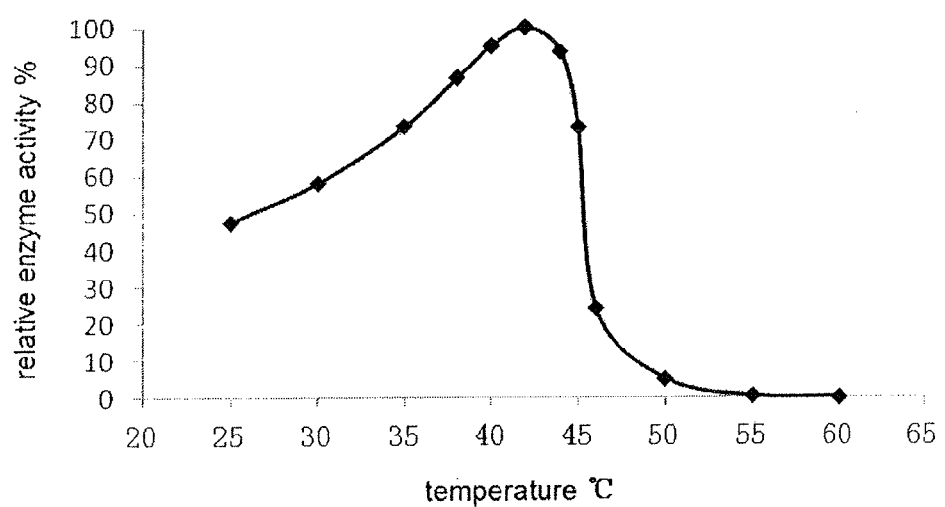
FIG. 3(A), effects of temperature on enzyme activity.

Effects of Temperature on Hyaluronidase Activity and Tests of Thermal Stability of Hyaluronidase Phosphate buffer solution with pH6.0 was used to prepare HA solution with final concentration of 2 mg/mL, 9.9 mL was taken and used as substrate solution, and 100 µL of appropriately diluted (as long as absorption value at 232 nm was 0.3-0.7) hyaluronidase solution (for example, the hyaluronidase prepared in any one of Examples 3-12) was added, the reaction under water-bath was performed at different temperature for 30 minutes, then boiled for 2 minutes, the pre-inactivated diluted enzyme solution was used as control, when they were cooled to room temperature, absorption values at 232 nm were measured (these values represented the activity of hyaluronidase), and the results were shown in FIG. 3(A), in which the most appropriate reaction temperature was 42° C.

Figure 3B:
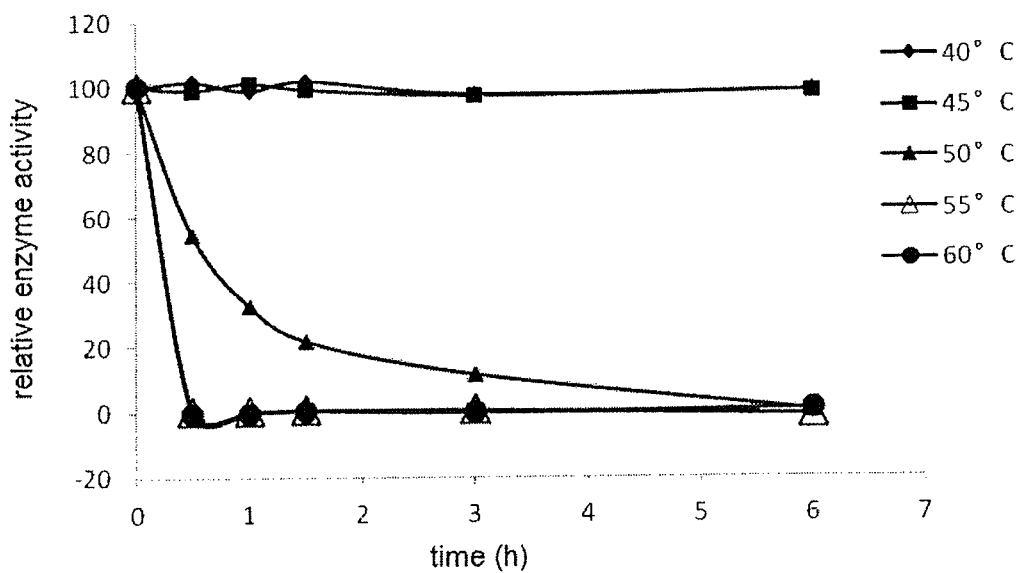
FIG. 3(B), experimental results of thermal stability of hyaluronidase.

The hyaluronidase solution was kept at constant temperature of 40° C., 45° C., 50° C., 55° C., 60° C., respectively, for different time periods, then residual enzyme activities were measured, and the results were shown in FIG. 3(B): the enzyme activity was relatively stable at 40° C. and 45° C., and almost did not change within 6 hours, which shows that the hyaluronidase activity was very stable at 45° C. or below, and it could satisfy requirements of industrial production at room temperature.

EXPERIMENTAL EXAMPLE 4

Figure 4A:
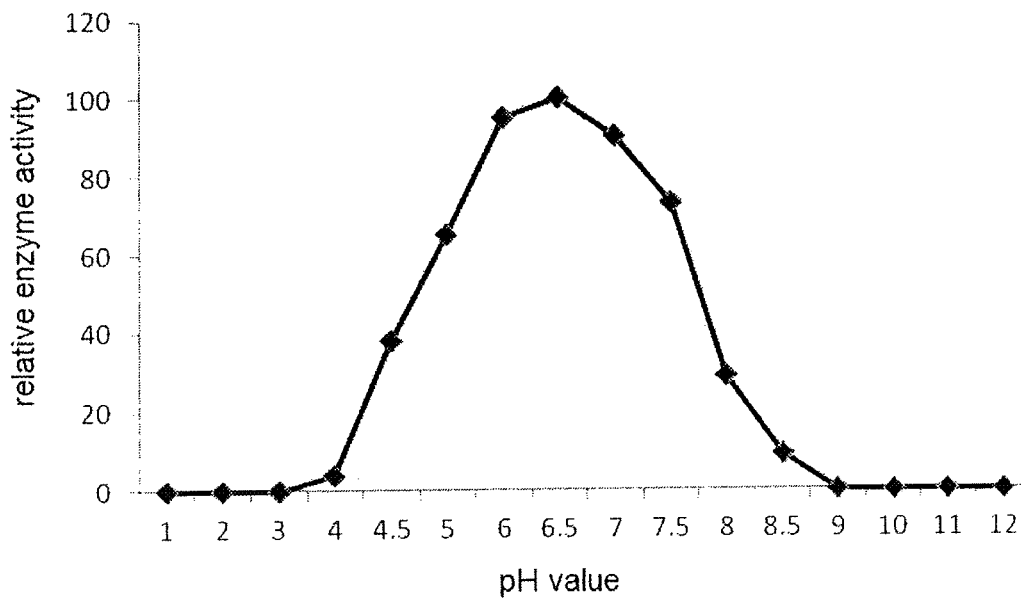
FIG. 4(A), effects of pH on enzyme activity.

Effects of pH on Hyaluronidase Activity and the Test of pH Stability of Hyaluronidase Buffer solutions of pH1.0-pH12.0 were prepared, respectively, and these buffer solutions were used to prepare 2 mg/mL hyaluronic acid solutions with corresponding pH, 9.9 mL HA solution of different pH was taken separately and used as substrate solution, and 100 µL of appropriately diluted (as long as absorption value at 232 nm was 0.3-0.7) hyaluronidase solution (for example, the hyaluronidase prepared in any one of Examples 3-12) was added, the reaction under water-bath was performed for 30 minutes, then boiled for 2 minutes, the pre-inactivated diluted enzyme solution was used as control, when they were cooled to room temperature, absorption values at 232 nm were measured, and the results were shown in FIG. 4(A): the most suitable pH for the enzyme was 6.5, and the enzyme had no activity when pH≤4.0 or pH≥9.0.

Figure 4B:
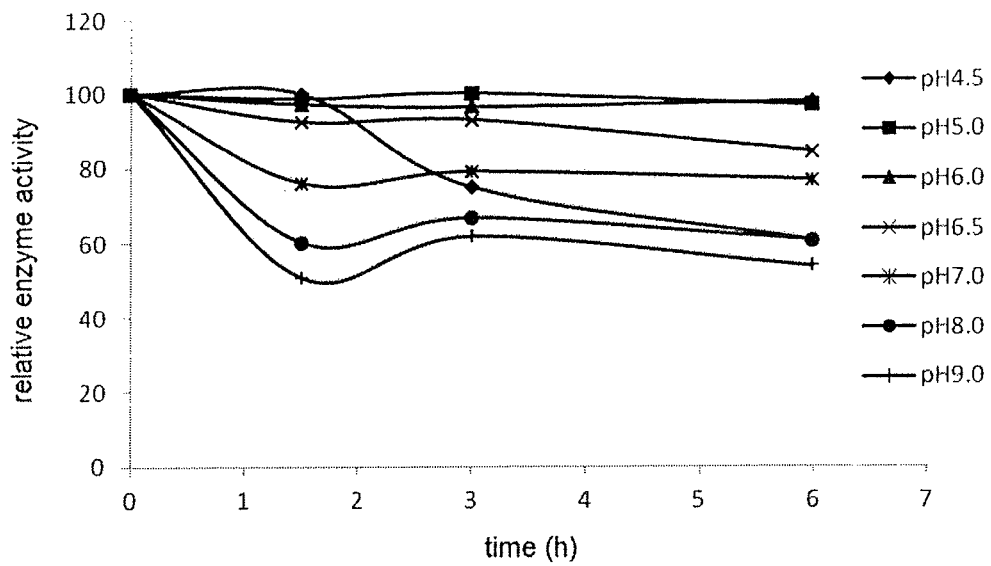
FIG. 4(B), experimental results of pH stability of hyaluronidase.

The hyaluronidase (for example, the hyaluronidase prepared in any one of Examples 3-12) was appropriately diluted with buffer solutions with different pH, then residual enzyme activities were measured, and the results were shown in FIG. 4(B): the enzyme activity was relatively stable at pH 5.0-6.0, which almost did not decrease within 6 h.

It can be seen that the hyaluronidase of the present invention has high enzyme activity, good thermal stability and pH stability, can satisfy requirements of enzyme amount for industrial degradation of hyaluronic acid in large scale, and the process for preparing the enzyme is simple, moderate in conditions, low in cost, and overcomes drawbacks such as environmental pollution of chemical degradation, limitation of source of biological degradation enzyme, low activity and high price.

EXPERIMENTAL EXAMPLE 5

Tests of Substrate Specificity of Enzyme

Solutions of chondroitin sulfate, sodium alginate, heparin sodium, chitosan, chitin and carboxymethyl cellulose sodium with final concentration of 10 mg/mL were separately prepared with pH 6.0 phosphate buffer solution, from each 9.9 mL was taken as substrate solution, and 100 µL of appropriately diluted (as long as absorption value at 232 nm was 0.3-0.7) hyaluronidase solution (for example, the hyaluronidase prepared in any one of Examples 3-12) was added, the reaction under water-bath was performed at 42° C. for 30 minutes, then boiled for 2 minutes, the pre-inactivated diluted enzyme solution was used as control, when they were cooled to room temperature, absorption values at 232 nm were measured. The results were shown in Table 4.

TABLE 4

| Substrate specificity of hyaluronidase | |
|---|---|
| Substrate | $A_{232}$ |
| Chondroitin sulfate | 1.0813 |
| Sodium alginate | 0 |
| Heparin sodium | 0 |
| Chitosan | 0 |
| Chitin | 0 |
| Carboxymethyl cellulose sodium | 0 |

The results showed the hyaluronidase can catalytically crack hyaluronic acid, as well as act on chondroitin sulfate, but cannot degrade sodium alginate, heparin sodium, chitosan, chitin and carboxymethyl cellulose sodium.

EXPERIMENTAL EXAMPLE 6

Comparison of Cytotoxicity of Oligomeric Hyaluronates Prepared by Chemical Degradation Method and Enzyme Digestion Method The experiment used L929 mouse fibroblast cells (purchased from the Cell Bank of the Committee on Type Culture Collection of Chinese Academy of Sciences) were used as observation cells, RPMI-1640 culture medium added with 10% fetal bovine serum was used as complete medium, the negative control was the complete medium without any sample to be tested, the positive control was 5 g/L phenol solution (dissolved in the complete medium), the blank control was cell-free complete medium, and the sample to be tested was complete medium added with oligomeric sodium hyaluronate sample. After culturing for 72 h, the relative growth rate (RGR) was calculated by the following formula.

$$RGR(\%) = \frac{A}{A_0} \times 100\%$$

wherein:
RGR—relative growth rate, %;
A—absorbance of the group of sample to be tested (the negative group, the positive group), with deduction of blank;
$A_0$—absorbance of the negative control group, with deduction of blank.

The grade of cytotoxicity was determined according RGR grading standard in Table 5. When the positive control group was at least grade 3 reaction, and the cytotoxicity reaction degree of the sample was not greater than grade 2, it was considered that its cytotoxicity was acceptable.

TABLE 5

Cytotoxicity reaction grades (according to United States Pharmacopeia)

| Grade | 0 | 1 | 2 | 3 | 4 |
|---|---|---|---|---|---|
| RGR(%) | ≥100 | 80-99 | 50-79 | 30-49 | 0-29 |

TABLE 6

Experimental results of cytotoxicity of oligomeric sodium hyaluronate

| Sample | Sample concentration (%, w/v) | OD$_{570}$ ($\bar{X} \pm SD$) | RGR (%) | Cytotoxicity grade |
|---|---|---|---|---|
| Comparative Example 1 | 0.25 | 0.762 ± 0.062 | 84.36 | 1 |
| | 0.5 | 0.681 ± 0.092 | 74.43 | 2 |
| | 1.0 | 0.629 ± 0.057 | 68.14 | 2 |
| | 2.0 | 0.452 ± 0.052 | 46.61 | 3 |
| | 3.0 | 0.357 ± 0.023 | 35.14 | 3 |
| | 4.0 | 0.193 ± 0.024 | 15.21 | 4 |
| Example 13 | 0.25 | 0.985 ± 0.063 | 110.94 | 0 |
| | 0.5 | 1.147 ± 0.059 | 130.43 | 0 |
| | 1.0 | 1.075 ± 0.041 | 121.74 | 0 |
| | 2.0 | 0.929 ± 0.095 | 104.21 | 0 |
| | 3.0 | 0.646 ± 0.038 | 70.20 | 2 |
| | 4.0 | 0.471 ± 0.039 | 49.19 | 3 |
| Example 14 | 0.25 | 1.012 ± 0.057 | 113.58 | 0 |
| | 0.5 | 1.107 ± 0.044 | 124.24 | 0 |
| | 1.0 | 0.998 ± 0.045 | 112.01 | 0 |
| | 2.0 | 0.935 ± 0.026 | 104.94 | 0 |
| | 3.0 | 0.742 ± 0.030 | 83.28 | 1 |
| | 4.0 | 0.520 ± 0.030 | 58.36 | 2 |
| Example 15 | 0.25 | 0.898 ± 0.060 | 100.79 | 0 |
| | 0.5 | 0.997 ± 0.045 | 111.90 | 0 |
| | 1.0 | 0.925 ± 0.038 | 103.82 | 0 |
| | 2.0 | 0.832 ± 0.041 | 93.38 | 1 |
| | 3.0 | 0.605 ± 0.058 | 67.90 | 2 |
| | 4.0 | 0.450 ± 0.049 | 50.51 | 2 |
| Example 16 | 0.25 | 1.015 ± 0.029 | 113.92 | 0 |
| | 0.5 | 1.090 ± 0.035 | 122.33 | 0 |
| | 1.0 | 0.985 ± 0.038 | 110.55 | 0 |
| | 2.0 | 0.886 ± 0.055 | 99.44 | 1 |
| | 3.0 | 0.721 ± 0.032 | 80.92 | 1 |
| | 4.0 | 0.489 ± 0.033 | 54.88 | 2 |
| Example 17 | 0.25 | 0.932 ± 0.054 | 104.60 | 0 |
| | 0.5 | 1.005 ± 0.067 | 112.79 | 0 |
| | 1.0 | 0.974 ± 0.051 | 109.32 | 0 |
| | 2.0 | 0.889 ± 0.055 | 99.78 | 1 |
| | 3.0 | 0.719 ± 0.042 | 80.70 | 1 |
| | 4.0 | 0.530 ± 0.039 | 59.48 | 2 |
| Example 18 | 0.25 | 1.033 ± 0.055 | 115.94 | 0 |
| | 0.5 | 1.213 ± 0.048 | 136.14 | 0 |
| | 1.0 | 1.098 ± 0.029 | 123.23 | 0 |
| | 2.0 | 0.980 ± 0.028 | 109.99 | 0 |
| | 3.0 | 0.726 ± 0.030 | 81.48 | 1 |
| | 4.0 | 0.501 ± 0.037 | 56.23 | 2 |
| Negative control | | 0.891 ± 0.030 | 100.00 | 0 |
| Positive control | | 0.071 ± 0.010 | 0.43 | 4 |

The results show that the oligomeric sodium hyaluronate prepared by chemical degradation method is not cytotoxic when its concentration is not greater than 1.0%; while the oligomeric sodium hyaluronate prepared by enzyme digestion method is not cytotoxic when its concentration is not greater than 3.0%. In comparison with the oligomeric sodium hyaluronate of chemical degradation method, the oligomeric sodium hyaluronate with the same concentration prepared by enzyme digestion method has significant effects on promoting cell proliferation ($p<0.05$).

EXPERIMENTAL EXAMPLE 7

Studying on Transdermal Absorption, Antioxidant Activity and Reduction Ability of Hyaluronate Prepared by Enzyme Digestion Method 1. Studying on Transdermal Absorption of Oligomeric Hyaluronate Prepared by Enzyme Digestion Method Skin material of hairless mice was fixed on diffusion cell of transdermal absorption instrument, 0.5% oligomeric hyaluronate (separately being prepared in Examples 13-18) solution was added to donor side of the diffusion cell, sample was taken per 3 hours and the content of oligomeric hyaluronate in received solution was measured. The results were shown in FIG. 5 (A). This diagram showed the oligomeric hyaluronate could enter into skin interior and be absorbed.

2. Studying on Antioxidant Activity of Oligomeric Hyaluronate and Low-Molecular-Weight Hyaluronate The oligomeric hyaluronates and low-molecular-weight hyaluronates prepared by enzyme digestion method and chemical degradation method were separately studied preliminarily on their ability of scavenging DPPH free radicals and their reduction ability.

The used reagents and cell strains were as follows:

Hyaluronate with different molecular weights:

Enzyme digestion oligomeric hyaluronates: prepared in Example 13-18;

Chemical method oligomeric hyaluronates: prepared according to Comparative Examples 1-2;

Enzyme digestion low-molecular-weight hyaluronates: prepared in Examples 19-26;

Chemical method low-molecular-weight hyaluronates: prepared in Comparative Examples 3-7;

High-molecular-weight sodium hyaluronate (molecular weight: 1610,000, HA-1610 k): produced by Huaxi Furuida Biological Medicine Co., Ltd.

1) Studying on Ability of Scavenging Free Radicals

The mechanism for measuring ability of scavenging DPPH free radicals: diphenyl-picrylhydrazine (DPPH) was a stable free radical with nitrogen center, the methanol solution or ethanol solution of DPPH was violet color, had maximum absorbance at wavelength of 510-530 nm, and its concentration was in linear relation with its absorbance. When there was free radical scavenger, free radical scavenger provided 1 electron to pair the lone pair electrons of DPPH and thus resulting in color fading, and the color fading degree is in quantitative relation with the received electrons, that was, the color of solution changed to light, and absorbance was reduced (Alisi, C. S., et al., Free radical scavenging and in-vitro antioxidant effects of ethanol extract of the medicinal herb *Chromolaena odorata* Linn. *British Journal of Pharmaceutical Research*, 2011, 1 (4), 141-155.). The greater the ability of free radical scavenger, the smaller the absorbance. 5.0 mL of 0.1 mM DPPH (2-methyl-2,3-dihydro-5,6-diphenylpyrazine) ethanol solution and 5.0 mL of oligomeric hyaluronate or low-molecular-weight hyaluronate with different concentrations were separately metered precisely, placed in plugged test tubes, and mixed uniformly. The isometric mixed solution of water and 95% ethanol was used as blank control. After standing at room temperature for 30 minutes, solution light absorbance values were separately measured at 523 nm.

$$scavenging\_rate(\%) = 1 - \frac{absorbance\_after\_reaction\_of\_HA\_and\_DPPH}{absorbance\_of\_DPPH\_alone}$$

Figure 5A:
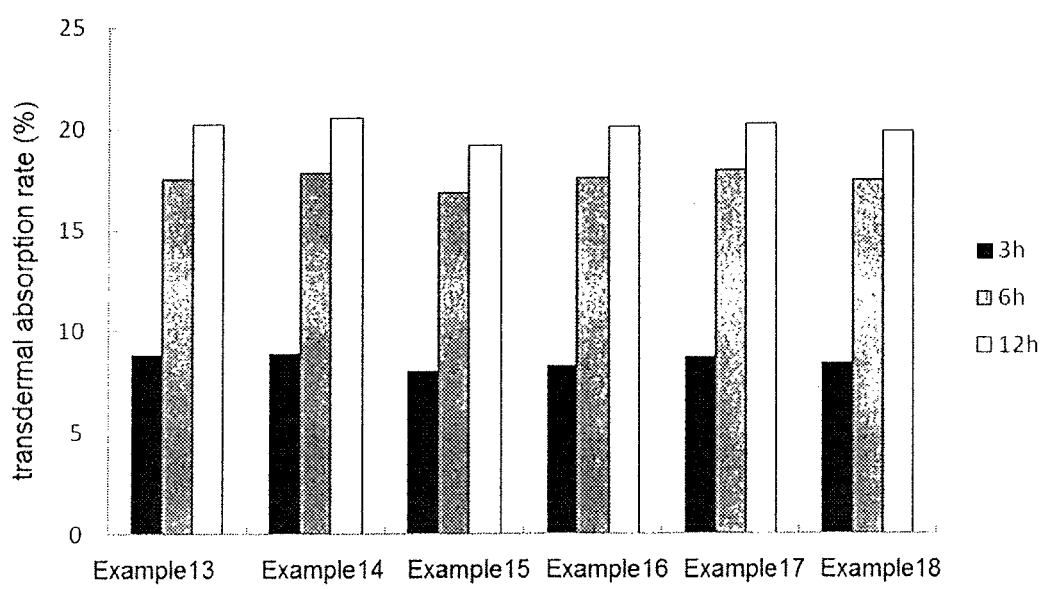
FIG. 5(A): graph of transdermal absorption rate of oligomeric hyaluronate.
Figure 5B:
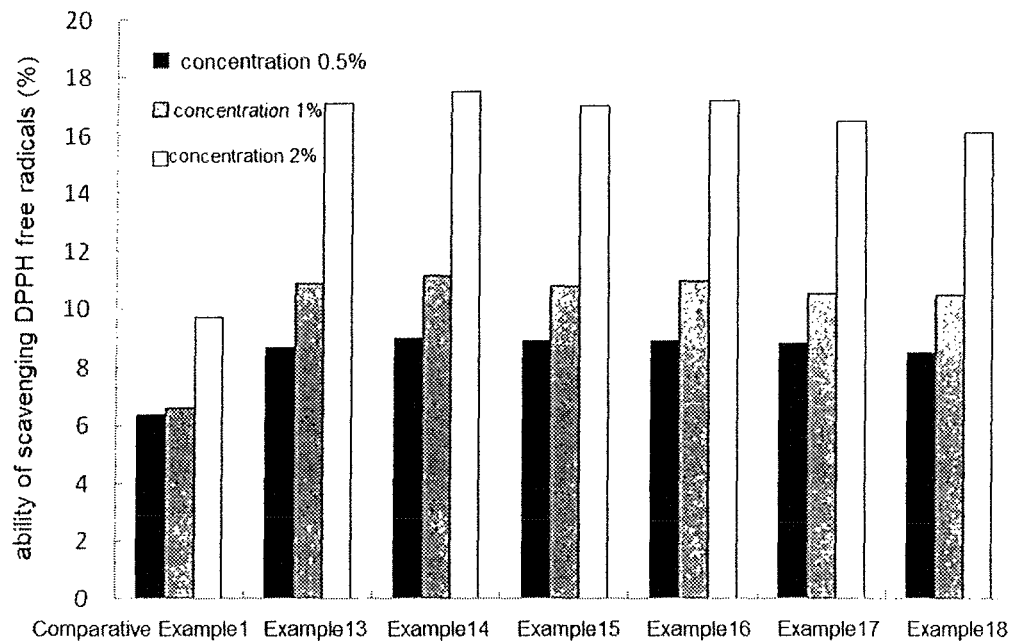
FIG. 5(B): graph of DPPH free radical scavenging capacity of oligomeric hyaluronate.
Figure 5C:
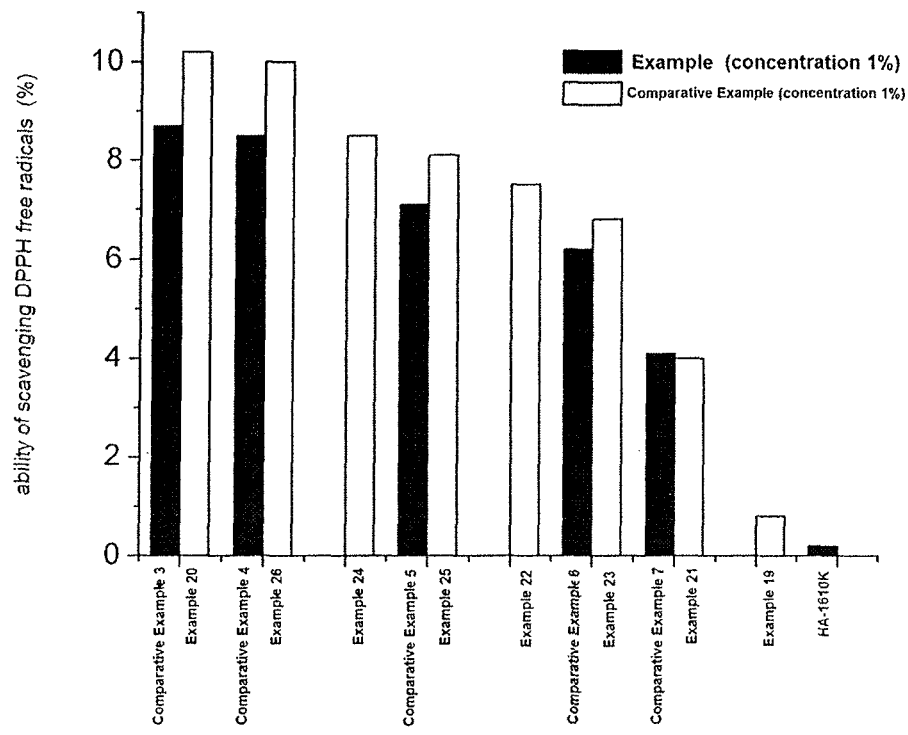
FIG. 5(C): graph of DPPH free radical scavenging capacity of low-molecular-weight hyaluronate.
Figure 5D:
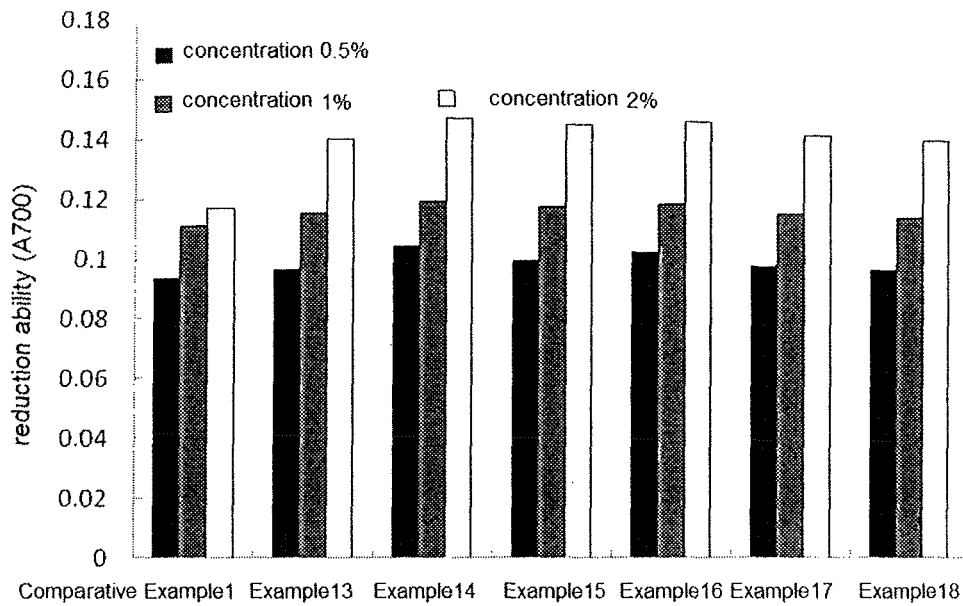
FIG. 5(D): graph of reduction ability of oligomeric hyaluronate.
Figure 5E:
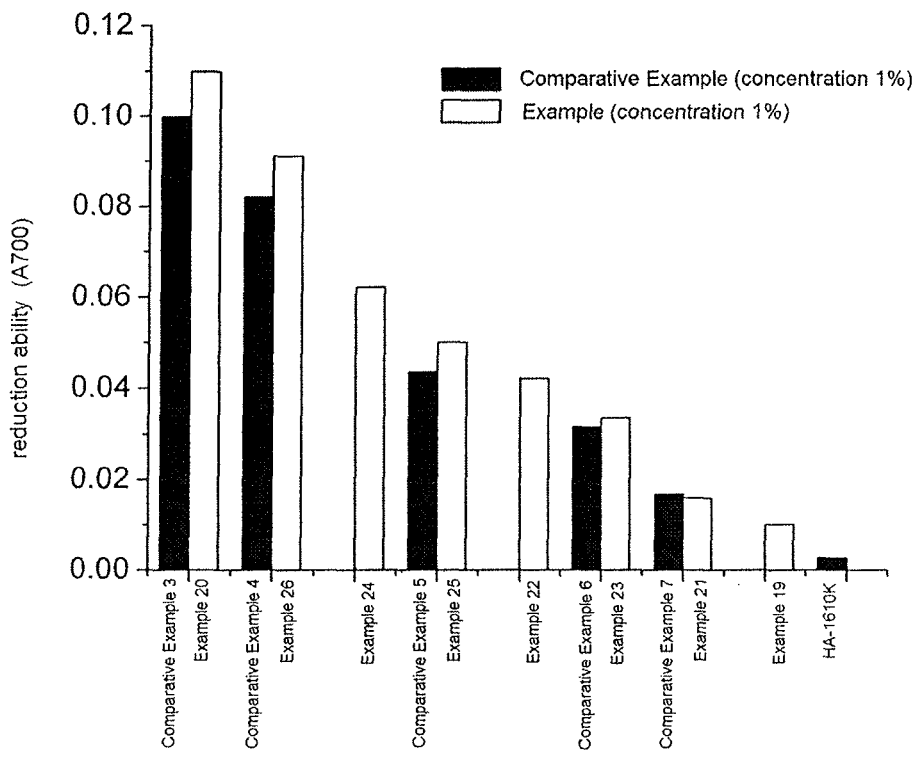
FIG. 5(E): graph of reduction ability of low-molecular-weight hyaluronate.
Figure 6A:
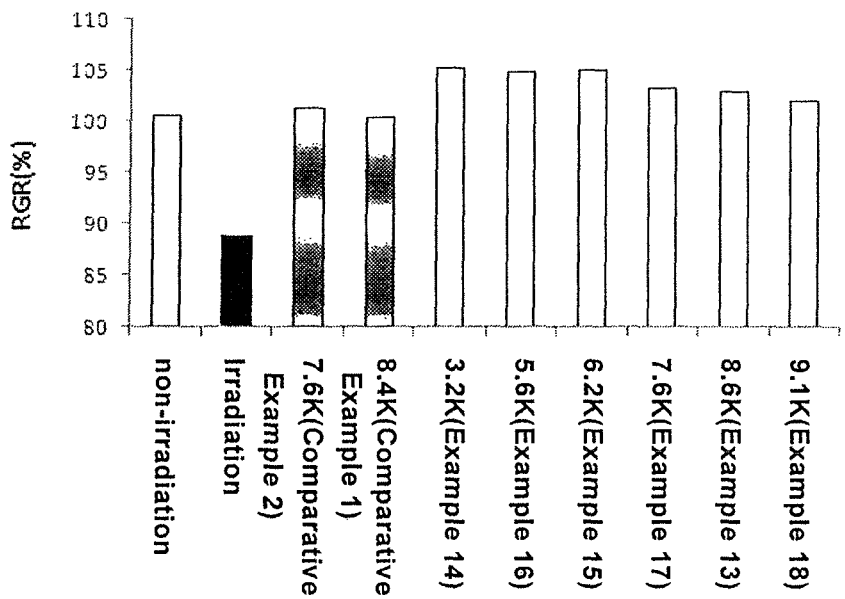
FIG. 6(A): repairing effects of oligomeric hyaluronate on L929 cells after UVA irradiation.
Figure 6B:
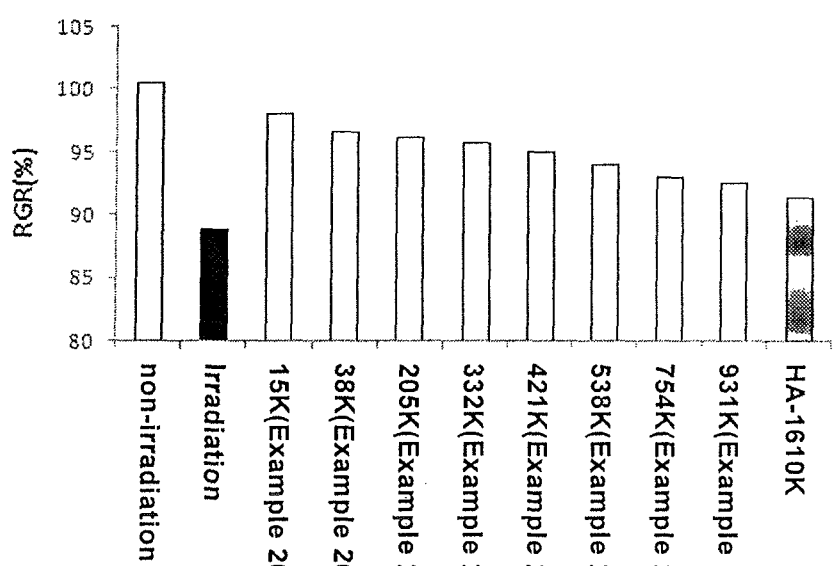
FIG. 6(B): repairing effects of low-molecular-weight hyaluronate on L929 cells after UVA irradiation.
Figure 6C:
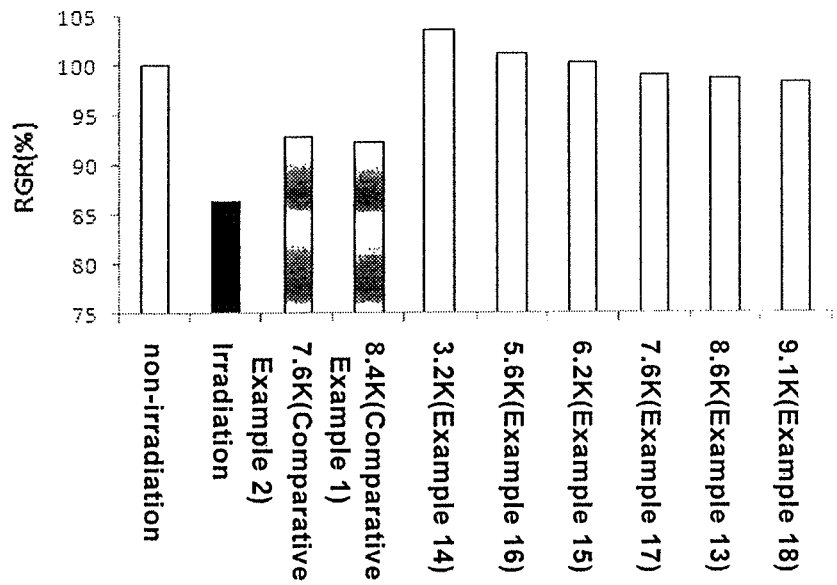
FIG. 6(C): protective effects of oligomeric hyaluronate on L929 cells against UVA irradiation.
Figure 6D:
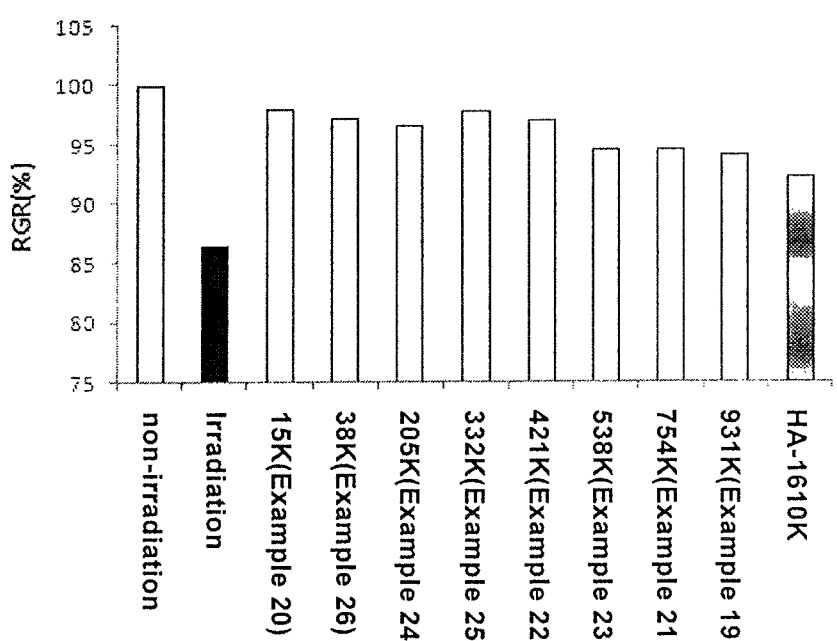
FIG. 6(D): protective effects of low-molecular-weight hyaluronate on L929 cells against UVA irradiation.

The experimental results of oligomeric hyaluronates were shown in FIG. 5(B), and it can be seen that in comparison with the chemical degradation oligomeric sodium hyaluronates (prepared in Comparative Example 1 or Comparative Example 2), the enzyme digestion oligomeric sodium hyaluronates (prepared in Examples 13-18) of the same concentration had greater ability of scavenging DPPH free radicals, p<0.05.

The experimental results of low-molecular-weight hyaluronates were shown in FIG. 5 (C).

The diagram showed that the ability of scavenging free radicals increased with the decrease of molecular weight in either chemical degradation low-molecular-weight hyaluronates or enzyme digestion low-molecular-weight hyaluronates. However, regarding to low-molecular-weight hyaluronates with similar molecular weight, the enzyme digestion low-molecular-weight hyaluronates had greater ability of scavenging free radicals in comparison with the chemical degradation low-molecular-weight hyaluronates. Hyaluronates with molecular weight of greater than 1000,000 almost had no ability of scavenging free radicals.

2) Measurement of Reduction Ability

Mechanism for measuring reduction ability: potassium ferricyanide in faint acid environment of pH6.6 could be reduced by reductive substance to generate potassium hexacyanoferrate $K_4Fe(CN)_6$, which further reacted with ferric ion provided by $FeCl_3$ to generate Prussian blue ($Fe_4[K_4Fe(CN)_6]_3$), which had specific absorbance at 700 nm, and by using the production amount of Prussian blue as index, the greater the absorbance, the stronger the reduction ability. Thus, when hyaluronate aqueous solution was used as raw material, its reduction ability could be judged by measuring the amount of Prussian blue generated in this system (Oyaizu, M. Antioxidant activity of browing products of glucosamine fractionated by organic solvent and thin-layer chromatography. *Japanese Journal of Nutrition*, 1986, 44, 307-315).

2.5 mL of solution of each of oligomeric hyaluronates (prepared in Examples 13-18) and low-molecular-weight hyaluronates (prepared in Examples 19-26) as well as 2.5 mL of phosphate solution were precisely metered and placed in plugged test tubes, respectively, added with 2.5 mL of 1.0% potassium ferricyanide solution, mixed uniformly, and treated with 50° C. water-bath for 20 minutes. After water-bath treatment, it was cooled rapidly, added with 2.5 mL of 10% trichloroacetic acid solution, centrifuged under 3000 rpm for 10 minutes. 8 mL of supernatant was taken and added with 5 mL of water and 1 mL of 0.1% ferric trichloride solution, and isometric water was used as blank control to replace ferric trichloride solution. After standing at room temperature for 10 minutes, solution absorbance values were measured at 700 nm.

The results of reduction ability of oligomeric hyaluronates were shown in FIG. 5 (D), and the diagram showed that in comparison with the chemical degradation oligomeric hyaluronates (prepared in Comparative Example 1 or Comparative Example 2), the enzyme digestion oligomeric hyaluronates of the same concentration had greater reduction ability, p<0.05.

The results of reduction ability of low-molecular-weight hyaluronates were shown in FIG. 5 (E), and this diagram showed that with the decrease of molecular weight, the reduction ability increased in either the chemical degradation low-molecular-weight hyaluronates or the enzyme digestion low-molecular-weight hyaluronates. However, regarding to low-molecular-weight hyaluronates with similar molecular weight, the enzyme digestion low-molecular-weight hyaluronates had greater reduction ability in comparison with the chemical degradation low-molecular-weight hyaluronates. Hyaluronates with molecular weight of greater than 1000,000 almost had no reduction ability.

The above experimental results showed that the enzyme digestion oligomeric hyaluronates (for example, oligomeric sodium hyaluronate) and low-molecular-weight hyaluronates (for example, low-molecular-weight sodium hyaluronate) had greater ability of scavenging DPPH free radicals and greater reduction ability in comparison with the chemical degradation oligomeric hyaluronates (for example, oligomeric sodium hyaluronate) and low-molecular-weight hyaluronates (for example, low-molecular-weight sodium hyaluronate), and thus could effectively scavenge free radicals in human body, reduce formation of melanin, and could be used in cosmetics to provide functions such as sun-protection, post-sunburn repairing, whitening and brightening, anti-aging; could also be used in health care foods and normal foods to provide functions of scavenging free radicals in body and anti-aging; and could also be used in medicines for combating damages caused by free radicals in body.

EXPERIMENTAL EXAMPLE 8

Studying on Functions of Enzyme Digestion Hyaluronates in Health Care Foods

1. Studying on Functions of Enzyme Digestion Oligomeric Hyaluronates in Health Care Foods For example, in a health care oral solution with oligomeric hyaluronate as main functional component, the amount of the added oligomeric hyaluronate was 0.05-2%. The formulation of the oral solution was of: adding with 0.5% oligomeric hyaluronate (prepared in any one of Examples 13-18), then adding with 25% edible sugar or bee honey, and dissolving with purified water. After complete dissolution, sterilization was performed by using ultrafiltration device, then it was poured into 10 mL oral solution bottles (sterilized with high temperature or ultraviolet ozone), capped and sealed, and all above operations were carried in clean workshop. The product was then subjected to quality test to obtain oligomeric hyaluronate oral solution. The subjects had age of 30-65, divided into 6 groups, 30 persons in each group, and each person was administrated with 10-20 mL of oligomeric hyaluronate oral solution per day, for a consecutive month, and the effects were shown in Table 7. Another 30 persons were used as control group, which were administered with solution of edible sugar or honey per day.

ing immunity, delaying senescence, restoring skin gloss and elasticity. The oligomeric hyaluronates of the present invention has small molecular weight, can be absorbed by intestine of human, so as to increase content of hyaluronic acid in tissues of body, supply to skin hyaluronic acid that may decrease due to aging. In addition, small molecular weight hyaluronic acid absorbed by oral administration can generate high molecular weight hyaluronic acid in body so that skin would become tender and smooth, joints become flexible, formation of wrinkles would be prevented, and thus it can be used in food field.

2. Studying on Functions of Low-Molecular-Weight Hyaluronates in Health Care Foods For example, in a health care oral solution with low-molecular-weight hyaluronate as main functional component, the amount of the added low-molecular-weight hyaluronate was 0.05-2%. The formulation of the oral solution was of: adding with 1.0% low-molecular-weight hyaluronate (prepared in any one of Examples 19-26), then adding with 25% edible sugar or bee honey. Method of formulation: performing formulation in a clean room, taking and stirring purified water at room temperature, adding in proportion the low-molecular-weight hyaluronate, then adding with edible sugar or bee honey under stirring until complete dissolution, adding with water to 100%. After complete dissolution, sterilization was performed by moist-heat sterilization, then it was poured into 10 mL oral solution

TABLE 7

Effects of administration of oligomeric hyaluronate oral solution

| Sample | Evaluation item | Significant change | Slight change | No change |
|---|---|---|---|---|
| Example 13 | 1. skin being smooth, watery and elastic | 24 | 5 | 1 |
| | 2. rosy cheeks, wrinkle reduction, youthful | 17 | 8 | 5 |
| | 3. enhanced resistance, not easy to get sick | 23 | 4 | 3 |
| | 4. body relax and healthy, not easy to get fatigue | 12 | 13 | 5 |
| Example 14 | 1. skin being smooth, watery and elastic | 25 | 4 | 1 |
| | 2. rosy cheeks, wrinkle reduction, youthful | 21 | 6 | 3 |
| | 3. enhanced resistance, not easy to get sick | 22 | 5 | 3 |
| | 4. body relax and healthy, not easy to get fatigue | 14 | 11 | 5 |
| Example 15 | 1. skin being smooth, watery and elastic | 22 | 5 | 3 |
| | 2. rosy cheeks, wrinkle reduction, youthful | 19 | 7 | 4 |
| | 3. enhanced resistance, not easy to get sick | 21 | 5 | 4 |
| | 4. body relax and healthy, not easy to get fatigue | 13 | 12 | 5 |
| Example 16 | 1. skin being smooth, watery and elastic | 23 | 5 | 2 |
| | 2. rosy cheeks, wrinkle reduction, youthful | 17 | 9 | 4 |
| | 3. enhanced resistance, not easy to get sick | 22 | 5 | 3 |
| | 4. body relax and healthy, not easy to get fatigue | 14 | 11 | 5 |
| Example 17 | 1. skin being smooth, watery and elastic | 24 | 4 | 2 |
| | 2. rosy cheeks, wrinkle reduction, youthful | 18 | 8 | 4 |
| | 3. enhanced resistance, not easy to get sick | 23 | 5 | 2 |
| | 4. body relax and healthy, not easy to get fatigue | 13 | 13 | 4 |
| Example 18 | 1. skin being smooth, watery and elastic | 21 | 7 | 2 |
| | 2. rosy cheeks, wrinkle reduction, youthful | 19 | 6 | 5 |
| | 3. enhanced resistance, not easy to get sick | 20 | 7 | 3 |
| | 4. body relax and healthy, not easy to get fatigue | 12 | 12 | 6 |
| Control group | 1. skin being smooth, watery and elastic | 1 | 7 | 22 |
| | 2. rosy cheeks, wrinkle reduction, youthful | 0 | 7 | 23 |
| | 3. enhanced resistance, not easy to get sick | 0 | 3 | 27 |
| | 4. body relax and healthy, not easy to get fatigue | 1 | 6 | 23 |

It could be seen from Table 7 that the oligomeric sodium hyaluronate could be directly eaten as health care food, very easy for absorption, and had many functions such as enhancbottles (sterilized with high temperature or ultraviolet ozone), capped and sealed, and all above operations were carried in clean workshop. The product was then subjected to quality test to obtain low-molecular-weight hyaluronate oral solution. The subjects had age of 22-55, divided into 8 groups, 32 persons in each group, and each person was administrated with 20 mL of low-molecular-weight hyaluronate oral solution per day, for a consecutive month. Another 30 persons were used as control group, which were administered with solution of edible sugar or bee honey per day.

Skin moisture contents and water loss amounts of subjects were measured with skin moisture meter by designated persons before and after administration, in which measurement sites and room temperature and humidity were kept consistently before and after measurement. The results of human skin moisture content measurement were shown in Table 8.

TABLE 8

Results of measurement of skin moisture contents

| Sample | | Moisture content (%) | Water loss amount (%) |
|---|---|---|---|
| Example 19 | Before administration | 28.86 ± 1.55 | 9.23 ± 0.85 |
| | After administration | 39.77 ± 1.94 | 6.51 ± 0.64 |
| Example 20 | Before administration | 27.54 ± 1.51 | 9.15 ± 0.80 |
| | After administration | 36.72 ± 1.75 | 6.92 ± 0.55 |
| Example 21 | Before administration | 25.69 ± 1.68 | 9.86 ± 0.81 |
| | After administration | 33.78 ± 1.54 | 6.67 ± 0.51 |
| Example 22 | Before administration | 28.27 ± 1.55 | 10.06 ± 0.78 |
| | After administration | 37.82 ± 1.75 | 7.39 ± 0.58 |
| Example 23 | Before administration | 25.26 ± 1.55 | 9.93 ± 0.75 |
| | After administration | 35.30 ± 1.94 | 7.58 ± 0.52 |
| Example 24 | Before administration | 22.47 ± 1.58 | 10.43 ± 0.87 |
| | After administration | 32.56 ± 1.83 | 7.01 ± 0.66 |
| Example 25 | Before administration | 24.78 ± 1.48 | 10.03 ± 0.82 |
| | After administration | 35.43 ± 1.94 | 7.35 ± 0.44 |
| Example 26 | Before administration | 22.16 ± 1.44 | 9.83 ± 0.79 |
| | After administration | 33.72 ± 1.85 | 6.71 ± 0.67 |
| Control group | Before administration | 29.11 ± 1.78 | 9.45 ± 0.75 |
| | After administration | 28.65 ± 1.66 | 8.89 ± 0.81 |

It could be seen from Table 8 that the subject groups showed significant increase of moisture content and significant improvement of water loss after 1 month of administration of low-molecular-weight hyaluronate in comparison with that of before administration. It was observed that the persons of subject groups showed better gloss, compactness and elasticity of skin in comparison with the control group. Thus, the oral administration of low-molecular-weight hyaluronic acid is easy for absorption, has good moisture holding and moisturizing effects, can activate skin cells, and thus has anti-aging function.

Therefore, after oral administration of oligomeric hyaluronate or low-molecular-weight hyaluronate, the gloss, elasticity of skin of subjects could be improved, and they could be used in health care foods as well as normal foods.

EXPERIMENTAL EXAMPLE 9

Studying on Effects of Enzyme Digestion Oligomeric Hyaluronate in Promoting Angiogenesis Human umbilical vein endothelial cell (HUVEC, provided by Shandong Province Academy of Medical Sciences) culture test and chicken chorioallantoic membrane (CAM) model test (hatching eggs were purchased from the Poultry Institute of Shandong Province Academy of Agricultural Sciences) were used to study whether the enzyme digestion oligomeric hyaluronate (prepared in any one of Examples 13-18) could promote angiogenesis. HUVEC proliferation effects and CAM angiogenesis effects were shown in Table 9. Experimental steps could refer to, for example, WANG Yanhou, WANG Fengshan, GUO Xueping, Preparation of relatively low molecular weight hyaluronic acid and effects thereof on promoting angiogenesis, Chinese Journal of Biochemical Pharmaceutics, 2007, 28(2):107-109.

TABLE 9

Effects of oligomeric sodium hyaluronate on promoting angiogenesis

| Group | Molecular weight (kDa) | Concentration (μg/mL) | Number of chicken embryo (egg) | Number of CAM vessels (vessels) | HUVEC proliferation ($OD_{570\,nm}$) |
|---|---|---|---|---|---|
| Blank control/Normal saline | — | — | 10 | 10.33 ± 3.67 | 0.402 ± 0.012 |
| Example 13 | 8.6 | 10 | 10 | 13.75 ± 4.83 | 0.412 ± 0.011 |
| | | 40 | 10 | 22.79 ± 4.52 | 0.435 ± 0.006 |
| Example 14 | 3.2 | 10 | 10 | 18.71 ± 4.67 | 0.410 ± 0.010 |
| | | 40 | 10 | 28.31 ± 4.56 | 0.455 ± 0.007 |
| Example 15 | 6.2 | 10 | 10 | 17.32 ± 5.64 | 0.408 ± 0.013 |
| | | 40 | 10 | 25.89 ± 3.51 | 0.447 ± 0.009 |
| Example 16 | 5.6k | 10 | 10 | 17.23 ± 3.42 | 0.413 ± 0.014 |
| | | 40 | 10 | 26.58 ± 4.68 | 0.450 ± 0.004 |
| Example 17 | 7.6k | 10 | 10 | 15.99 ± 5.04 | 0.402 ± 0.011 |
| | | 40 | 10 | 23.24 ± 3.65 | 0.438 ± 0.005 |
| Example 18 | 9.1k | 10 | 10 | 12.89 ± 4.61 | 0.409 ± 0.010 |
| | | 40 | 10 | 22.48 ± 4.74 | 0.442 ± 0.007 |
| Positive control (bFGF*) | — | 40 IU/ml | 10 | 25.74 ± 3.67 | 0.475 ± 0.014 |

The experimental results showed that the oligomeric sodium hyaluronate had significant activity of promoting angiogenesis, could promote angiogenesis of CAM in vivo, and could promote proliferation of HUVEC cells in vitro, and could be used in medical fields such as wound healing.

EXPERIMENTAL EXAMPLE 10

Studying on Effects of Hyaluronates in Post-Sunburn Repairing and Sun-Protection Ultraviolet ray (mainly comprising UVA and UVB) in sun light is an important factor for causing sun-burn and sun-ageing of skin as well as skin cancers. All of three kinds of cells of skin body, i.e. keratinocytes, fibroblasts and melanocytes are sensitive to ultraviolet ray. UVA damage is mainly to cause oxidative damage of DNA of skin fibroblasts, which may result in occurrence of DNA mutation and skin cancers. In this experiment, mouse fibroblasts L929 (purchased from the Cell Bank of Committee on Type Culture Collection of Chinese Academy of Sciences) were exposed to certain dose of UVA, then the cells were treated with hyaluronate, so as to study effects of hyaluronates prepared by different degradation methods and hyaluronates with different molecular weights on L929 cells exposed to UVA irradiation; and mouse fibroblasts L929 were treated with hyaluronate, then the cells were exposed to a dose of UVA irradiation, so as to study effects of hyaluronates prepared by different degradation methods and hyaluronates with different molecular weights on UVA irradiation protection to L929 cells.

The used reagents and cell strains were as follows:

Fibroblast cell strain L929: purchased from the Cell Bank of the Committee on Type Culture Collection of Chinese Academy of Sciences;

Hyaluronates with different molecular weights:

Enzyme digestion oligomeric hyaluronates: prepared in Examples 13-18;

Chemical degradation oligomeric hyaluronates: prepared according to Comparative Examples 1-2;

Enzyme digestion low-molecular-weight hyaluronates: prepared in Examples 19-26;

Chemical degradation low-molecular-weight hyaluronates: prepared in Comparative Examples 3-7;

High molecular weight sodium hyaluronate (molecular weight: 1610,000, HA-1610 k): produced by Huaxi Furuida Biomedical Co., Ltd.

1. Studying on Repairing Effects of Hyaluronates Against Ultraviolet

The repairing effects of hyaluronates prepared by different preparation methods and hyaluronates with different molecular weights on L929 mouse fibroblast cells after UVA irradiation.

L929 cells during logarithmic growth phase were taken, digested with pancreatic enzyme, adjusted to have a cell density of $2 \times 10^4$/mL, inoculated on 96-well cell culture plate, 100 μL of cell suspension per well, placed in carbon dioxide incubator and conventionally cultured at 37° C., 5% $CO_2$ overnight. Culture media were removed from 96-well plate, and then 100 μL of PBS was added to per well. The negative control group was not exposed to irradiation, while the L929 cells of other test groups were exposed to 7.2 J/cm$^2$ UVA irradiation. PBS was removed after irradiation, and the cells were treated by the following operations:

Non-irradiation group (negative control group): added with 100 μL of complete culture medium;

Irradiation group (positive control group): added with 100 μL of complete culture medium;

Irradiation+hyaluronate: added with 100 μL of complete culture medium containing 0.0625% hyaluronate;

After 24 hours of continuous culture, 20 μL of MTT was added to per well, incubation was then continued in cell culture incubator for 4 hours. Culture solution was discarded, 150 μL of DMSO was added to per well, shaken under dark for 10 minutes, and light absorbance values were measured at wavelength of 570 nm with enzyme labelling instrument. The relative growth rate (RGR) of cells was calculated with the following formula:

$$RGR(\%) = \frac{A_c}{A_{c,0}} \times 100\%$$

wherein $A_c$ represents absorbance value of test group, $A_{c,0}$ represents absorbance value of negative control group.

The results were shown in FIG. 6 (A) and FIG. 6 (B), oligomeric hyaluronates prepared by different degradation methods and hyaluronates with different molecular weights all had effects of repairing damaged cells after UVA irradiation, in which the enzyme digestion oligomeric hyaluronate had best post-sunburn repairing effects, while the effects of chemical degradation oligomeric hyaluronates were next-best. In addition, with the decrease of molecular weight of hyaluronate, the repairing effects became better. The enzyme digestion oligomeric hyaluronates and low-molecular-weight hyaluronates had better post-sunburn repairing effects than that of the high molecular weight hyaluronate.

2. Studying on Ultraviolet Protection Effects of Hyaluronates

The protection effects of oligomeric hyaluronates prepared by different methods and hyaluronates with different molecular weights against UVA irradiation on L929 mouse fibroblast cells were studied.

In this experiment, hyaluronates with different molecular weights were applied to mouse fibroblast cell strain L929, then the cells were exposed to certain dose of UVA irradiation, and the protection effects of hyaluronates with different molecular weights and oligomeric hyaluronates prepared by different methods against UVA irradiation on L929 mouse fibroblast cells were studied.

Cells during logarithmic growth phase were taken, digested with pancreatic enzyme, adjusted to have a cell density of $2 \times 10^4$/mL, inoculated on 96-well cell culture plate, 100 μL of cell suspension per well, placed in carbon dioxide incubator and conventionally cultured at 37° C., 5% $CO_2$ overnight. Culture media were removed after overnight culture, and cells were treated in groups as follows, and were incubated in cell culture incubator for 12 hours.

Non-irradiation group (negative control group): added with 100 μL of complete culture medium;

Irradiation group (positive control group): added with 100 μL of complete culture medium;

Irradiation+hyaluronate: added with 100 μL of complete culture medium containing 0.0625% hyaluronate;

Culture solution in the 96-well plate was discarded, and then 100 μL of PBS was added to per well. Except non-irradiation group, the L929 cells of all test groups were exposed to 7.2 J/cm$^2$ UVA irradiation. PBS was discarded after irradiation, 20 μL of MTT was added to per well, and incubation was continued in cell culture incubator for 4 hours. Culture solution was discarded, 150 μL of DMSO was added to per well, shaken under dark for 10 minutes, and light absorbance values were measured at wavelength of 570 nm with enzyme labelling instrument. The relative growth rate (RGR) of cells was calculated with the following formula:

$$RGR(\%) = \frac{A_c}{A_{c,0}} \times 100\%$$

wherein $A_c$ represents absorbance value of test group, $A_{c,0}$ represents absorbance value of negative control group.

The results were shown in FIG. 6 (C) and FIG. 6 (D), oligomeric hyaluronates prepared by different methods and hyaluronates with different molecular weights all had protection effects against UVA irradiation. The enzyme digestion oligomeric hyaluronate had best protection effects against UVA irradiation, while the effects of enzyme digestion low-molecular-weight hyaluronates were next-best. The chemical method oligomeric hyaluronates and high molecular weight hyaluronates had worst protection effects.

In sum, the enzyme digestion oligomeric hyaluronates and low-molecular-weight hyaluronates all had repairing effects against ultraviolet rays and protection effects against ultraviolet rays, in which the enzyme digestion oligomeric hyaluronates had best repairing effects against ultraviolet rays and protection effects against ultraviolet rays; the low-molecular-weight hyaluronates had good protection effects against ultraviolet rays, and their repairing effects against ultraviolet rays were inferior to that of the chemical method oligomeric hyaluronates but were superior to that of the high molecular weight hyaluronate. Thus, the enzyme digestion oligomeric hyaluronates and low-molecular-weight hyaluronates could be used in cosmetics for sun protection and post-sunburn repairing.

It can be seen from the above-mentioned that the oligomeric hyaluronates and low-molecular-weight hyaluronates obtained by the preparation methods of the present invention can permeate into epidermal layer of skin by external use, providing nutrients and moisture to skin, preventing skin ageing, preventing harm of ultraviolet rays, repairing sunburned skin cells, and thus can be used in cosmetics; it is easily absorbable by oral administration, not only scavenging free radicals, activating skin cells, keeping skin moist, but also having good effects of enhancing immune function and anti-aging function, and thus can be used in foods and health care products. In addition, it has functions of promoting angiogenesis, cellular immune activation and bone formation, as well as good therapeutic effects for bacterial keratitis, and thus can be used in fields of medicines.

Although the specific models of the present invention are illustrated in details, those skilled in the art can understand that these details could be modified or changed according to the teachings in the art, and all these changes are in the protection scope of the present invention. The whole scope of the present invention is given by the appended claims and any equivalents thereof.

What is claimed is:

1. A process for preparing a hyaluronidase, comprising the steps of culturing the *Bacillus* sp. which was deposited at China General Microbiological Culture Collection Center (CGMCC) with a deposit access number of CGMCC NO. 5744 and a deposit date of Feb. 8, 2012, wherein the amino acid sequence of the hyaluronidase is shown by SEQ ID NO: 2, wherein said *Bacillus* sp. expresses a hyaluronidase having an amino acid sequence as set forth by SEQ ID NO: 2.

2. The process according to claim 1, comprising the following steps:
   (1) subjecting the *Bacillus* sp. to slant culture so as to obtain a slant strain;
   (2) inoculating the slant strain to a sterilized seed culture medium, and culturing under the conditions of 25° C.-40° C., 100-200 rpm for 10-24 hours, to obtain a seed solution;
   (3) inoculating the seed solution to a sterilized fermentation culture medium, and culturing under the conditions of 25° C.-40° C., 100-300 rpm for 12-24 hours, to obtain a hyaluronidase fermentation broth;

(4) separating the fermentation broth by centrifugation to obtain a supernatant;

(5) subjecting the supernatant to ammonium sulfate fractional precipitation and filtration, to obtain a crude hyaluronidase; and (6) dissolving the crude hyaluronidase obtained in step (5) in a phosphate buffer solution, removing small molecular impurities by ultrafiltration, to obtain a purified hyaluronidase.

3. A process for preparing oligomeric hyaluronic acid or oligomeric hyaluronate, comprising the step of degrading hyaluronic acid or salts thereof with molecular weight greater than 10 kDa by using a polypeptide, wherein the amino acid sequence of the polypeptide is shown by SEQ ID NO: 2.

4. The process according to claim 3, comprising the following steps:
1) preparing the solution of hyaluronic acid or salts thereof: adding hyaluronic acid or salts thereof with molecular weight greater than 10 kDa to purified water, to obtain a solution with a concentration of 1% w/v-30% w/v;
2) enzymolysis: adjusting the temperature of the solution of step 1) to 20° C.-48° C., pH to 4-9, then adding the polypeptide to the solution, degrading the hyaluronic acid or salts thereof to a desired molecular weight, to obtain a enzymolysis solution;
3) inactivation: maintaining the enzymolysis solution at 50° C.-90° C. for 10-60 minutes, to inactivate the *Bacillus* sp. hyaluronidase.

5. The process according to claim 4, wherein, in step 1), to per 1 kg of hyaluronic acid or salts thereof, $2\times10^7$-$5\times10^7$ IU of polypeptide is added.

6. The process according to claim 4, wherein, in step 2), the temperature for enzymolysis is 35° C.-45° C., the pH for enzymolysis is 5.5-7.5, and hyaluronic acid is enzymolyzed to a molecular weight of greater than or equal to 3000 Da, and less than $10^4$ Da.

7. The process according to claim 4, which is characterized by one or more of the following (A)-(F):
(A) in step 1), hyaluronate is selected from the group consisting of sodium salt, potassium salt, magnesium salt, calcium salt and zinc salt of hyaluronic acid;
(B) in step 2), an acid or a base is used to adjust pH to 4-9, said acid is selected from the group consisting of hydrochloric acid, glacial acetic acid, sulfuric acid and phosphoric acid, said base is sodium hydroxide or potassium hydroxide;
(C) in step 3), the enzymolysis solution is kept at 55° C.-65° C. for 20-30 min, to inactivate the *Bacillus* sp. hyaluronidase;
(D) in step 4), said soluble inorganic salt is selected from the group consisting of sodium salt, potassium salt, calcium salt, zinc salt and magnesium salt;
(E) in step 5), said alcohol or ketone is ethanol, acetone, methanol, propanol, or isopropanol;
(F) in step 6), the organic solvent used for dehydrating is ketone or alcohol.

8. A process for preparing low-molecular-weight hyaluronic acid or low-molecular-weight hyaluronate, comprising the step of degrading hyaluronic acid with molecular weight of greater than 1000 kDa or salts thereof by using a polypeptide, wherein the amino acid sequence of the polypeptide is shown by SEQ ID NO: 2.

9. The process according to claim 8, comprising the following steps:
1) preparing a solution of hyaluronic acid or salts thereof: adding hyaluronic acid or salts thereof with molecular weight of greater than 1000 kDa to purified water, to prepare a solution with concentration of 0.1% wt/vol-2% w/v;
2) enzymolysis: adjusting the temperature of the solution of step 1) to 20° C.-48° C., pH to 4-9, then adding the polypeptide to the solution, degrading the hyaluronic acid or salts thereof to a desired molecular weight, to obtain a enzymolysis solution;
3) inactivation: keeping the enzymolysis solution at 50° C.-90° C. for 10-60 minutes, to inactivate the *Bacillus* sp. hyaluronidase.

10. The process according to claim 9, wherein, in step 1), to per 1 kg of hyaluronic acid or salts thereof; $10^6$-$10^7$ IU of polypeptide is added.

11. The process according to claim 9, wherein, in step 2), the temperature for enzymolysis is 35° C.-45° C., pH for enzymolysis is 5.5-7.5, and hyaluronic acid is enzymolyzed to a molecular weight of 10 kda-1000 kDa.

12. The process according to claim 9, which is characterized by one or more of the following (A)-(F):
(A) in step 1), hyaluronate is selected from the group consisting of sodium salt, potassium salt, magnesium salt, calcium salt and zinc salt of hyaluronic acid;
(B) in step 2), an acid or a base is used to adjust pH to 4-9, said acid is selected from the group consisting of hydrochloric acid, glacial acetic acid, sulfuric acid and phosphoric acid, said base is sodium hydroxide or potassium hydroxide;
(C) in step 3), the enzymatic hydrolysate is kept at 55° C.-65° C. for 20-30 minutes to inactivate the *Bacillus* sp. hyaluronidase;
(D) in step 4), said soluble inorganic salt is selected from the group consisting of sodium salt, potassium salt, calcium salt, zinc salt and magnesium salt;
(E) in step 5), said alcohol or ketone is ethanol, acetone, methanol, propanol, or isopropanol;
(F) in step 6), the organic solvent used for dehydrating is ketone or alcohol.

13. The process according to claim 1, comprising the following steps:
subjecting the *Bacillus* sp. to slant culture, seed culture, fermentation culture, centrifugation, ammonium sulfate fractional precipitation, and ultrafiltration, to obtain the hyaluronidase.

14. The process according to claim 2, wherein in step (5), said filtration is performed by using a 0.65 μm microfiltration membrane.

15. The process according to claim 2, wherein step (6) comprises the following steps (6-1) to (6-3):
(6-1): dissolving the crude hyaluronidase of step (5) in a buffer solution with pH 4.5-8.0 to obtain a crude enzyme solution; loading the crude enzyme solution to a dialysis bag with a molecular cutoff of $3.0\times10^3$ - $1.4\times10^4$ Da, placing in a buffer solution with pH 4.5-8.0, dialyzing at 4° C. overnight;
(6-2): subjecting the dialyzed crude enzyme solution to ion exchange chromatography separation, in which chromatography column packing of Diethylaminoethyl Sepharose Fast Flow Medium (DEAE Sepharose FF Medium) and 0-0.5 M NaCl solution for gradient elution are used, and collecting elution peaks; and (6-3): subjecting the hyaluronidase sample obtained in step (6-2) to vacuum freeze drying to obtain white powder as hyaluronidase.

16. The process according to claim 4, which further comprises the following steps:
- 4) filtration: adding a soluble inorganic salt to the inactivated enzymolysis solution, stirring until it is completely dissolved, then filtering with 0.45 μm filtration membrane to obtain a filtrate, wherein to per 100 mL of enzymolysis solution, 0.1-10 g of the soluble inorganic salt is added;
- 5) precipitation: uniformly mixing the filtrate of step 4) with alcohol or ketone in 3-20 times volume of the filtrate, to precipitate oligomeric hyaluronate;
- 6) dehydrating and drying: separating out the oligomeric hyaluronate precipitate of step 5), dehydrating with a organic solvent, then vacuum drying, to obtain oligomeric hyaluronate.

17. The process according to claim 7, wherein in step 4), said soluble inorganic salt is selected from the group consisting of chloride, sulfate or nitrate of sodium, potassium, calcium, zinc or magnesium.

18. The process according to claim 9, which further comprises the following steps:
- 4) filtration: adding a soluble inorganic salt to the inactivated enzymatic hydrolysate, stirring until it is completely dissolved, then filtering with 0.45 μm filtration membrane to obtain a filtrate, wherein to per 100 mL of enzymolysis solution, 0.1-10 g of the soluble inorganic salt is added;
- 5) precipitation: uniformly mixing the filtrate of step 4) with alcohol or ketone in 1-10 times volume of the filtrate, to precipitate low-molecular-weight hyaluronate;
- 6) dehydrating and drying: separating out the low-molecular-weight hyaluronate precipitate of step 5), dehydrating with a organic solvent, then vacuum drying, to obtain low-molecular-weight hyaluronate.

19. The process according to claim 12, wherein in step 4), said soluble inorganic salt is selected from the group consisting of chloride, sulfate or nitrate of sodium, potassium, calcium, zinc or magnesium.

20. A recombinant vector, which comprises a polynucleotide, wherein the polynucleotide encodes a polypeptide, and wherein the amino acid sequence of the polypeptide is shown by SEQ ID NO: 2.

21. A recombinant host cell, which comprises the recombinant vector of claim 20.

22. The recombinant vector according to claim 20, wherein the sequence of the polynucleotide is shown by SEQ ID NO: 3.

23. The recombinant host cell according to claim 21, wherein the recombinant host cell comprises a recombinant vector comprising a polynucleotide with a sequence shown by SEQ ID NO: 3.

* * * * *

SEQUENCE LISTING

<160> NUMBER OF SEQ ID NOS: 5

<210> SEQ ID NO 1
<211> LENGTH: 1418
<212> TYPE: DNA
<213> ORGANISM: Bacillus sp.

<400> SEQUENCE: 1

```
gcggctggct ccttacggtt accccaccga cttcgggtgt tacaaactct cgtggtgtga      60
cgggcggtgt gtacaaggcc cgggaacgta ttcaccgcgg catgctgatc cgcgattact     120
agcgattccg gcttcatgca ggcgagttgc agcctgcaat ccgaactgag aatggtttta     180
tgggattggc taaacctcgc ggtcttgcag ccctttgtac catccattgt agcacgtgtg     240
tagcccaggt cataaggggc atgatgattt gacgtcatcc ccaccttcct ccggtttgtc     300
accggcagtc accttagagt gcccaactga atgctggcaa ctaagatcaa gggttgcgct     360
cgttgcggga cttaacccaa catctcacga cacgagctga cgacaaccat gcaccacctg     420
tcactctgtc ccccgaaggg gaacgtccta tctctaggag tgtcagagga tgtcaagacc     480
tggtaaggtt cttcgcgttg cttcgaatta aaccacatgc tccaccgctt gtgcgggccc     540
ccgtcaattc ctttgagttt cagccttgcg gccgtactcc ccaggcggag tgcttaatgc     600
gttagctgca gcactaaagg gcggaaaccc tctaacactt agcactcatc gtttacggcg     660
tggactacca gggtatctaa tcctgtttgc tccccacgct ttcgcgcctc agcgtcagtt     720
acagaccaga aagccgcctt cgccactggt gttcctccac atctctacgc atttcaccgc     780
tacacgtgga attccgcttt cctcttctgt actcaagtcc cccagtttcc aatgaccctc     840
cacggttgag ccgtgggctt tcacatcaga cttaaaggac cgcctgcgcg cgctttacgt     900
ccaataattc cggacaacgc ttgccaccta cgtattaccg cggctgctgg cacgtagtta     960
```

```
gccgtggctt tctggttagg taccgtcaag gtaccggcag ttactccggt acttgttctt    1020
ccctaacaac agagctttac gacccgaagg ccttcatcgc tcacgcggcg ttgctccgtc    1080
agactttcgt ccattgcgga agattccta ctgctgcctc ccgtaggagt ctgggccgtg     1140
tctcagtccc agtgtggccg atcaccctct caggtcggct acgcatcgtc gccttggtga    1200
gccgttacct caccaactag ctaatgcgcc gcgggcccat ctgtaagtgt cagcgtaaac    1260
cgactttcag cttttcctca tgagaggaaa aggattatcc ggtattagct ccggtttccc    1320
gaagttatcc cagtcttaca ggcaggttgc ccacgtgtta ctcacccgtc cgccgctaac    1380
caagaggtgc aagcacctca agattcgctc gacttgca                            1418
```

<210> SEQ ID NO 2
<211> LENGTH: 1106
<212> TYPE: PRT
<213> ORGANISM: Artificial Sequence
<220> FEATURE:
<223> OTHER INFORMATION: Synthetic amino acid

<400> SEQUENCE: 2

```
Asn Glu Ser Thr Leu Leu Asn Thr Ser Phe Glu Glu Thr Glu Ala
1               5                   10                  15

Pro Lys Ser Gly Trp Asp Gln Leu Gly Ala Pro Lys Trp Gly Val Trp
            20                  25                  30

Arg Pro Thr Gly Ser Pro Ile Val Thr Ile Thr Lys Glu Ala Ser Arg
        35                  40                  45

Thr Gly Glu Tyr Gly Leu Lys Ile Ala Ala Gln Ser Ala Arg Ala
    50                  55                  60

Ala Val Ser Gln Asp Val Pro Val Gln Gly Gln Thr Tyr Gln Leu
65              70                  75                  80

Gly Thr Trp Leu Lys Thr Asp Asn Ile Val Ser Gly Gln Gly Ala Arg
                85                  90                  95

Leu Arg Val Val Leu Tyr Glu Gly Thr Gln Gln Leu Gly Leu Leu Tyr
            100                 105                 110

Ser Ser Arg Leu Thr Gly Thr His Asp Trp Ser Gln Ile Lys Met Glu
        115                 120                 125

Val Lys Thr Pro Ala Asn Ala Asp Ser Ile Arg Val Gln Leu Phe Phe
    130                 135                 140

Glu Thr Gly Thr Gly Thr Ala Leu Phe Asp Asp Val Ser Leu Gln Leu
145                 150                 155                 160

Ile Gln Pro Ala Thr Ser Ile Ala Ile Glu Glu Ser Glu Ile Thr Ile
                165                 170                 175

Lys Glu Gln Glu Thr Gly Leu Leu His Ala Gln Met Val Pro Ala Asp
            180                 185                 190

Ala Ser Ser Lys Val Ser Trp Val Ser Ala Asp Pro Ser Ile Ala Thr
        195                 200                 205

Val Asp Asn Gly Lys Val Thr Gly Val Asn Pro Gly Gly Thr Thr Ile
    210                 215                 220

Met Ala Phe Thr Asp Asn Gly Leu Ala Ala Thr Ser Thr Val Lys Val
225                 230                 235                 240

Ile Lys Asn Asp Gly Ile Glu Arg Pro Glu Val Thr Gln Leu Asp Leu
                245                 250                 255

Gln Pro Lys Glu Leu Glu Leu Gly Ser Gly Gln Val Arg Leu Leu Gln
            260                 265                 270

Ala Ile Ile Ala Pro Ala Thr Ala Asp Ala Glu Lys Leu Val Trp Ser
        275                 280                 285
```

```
Ser Ser Asn Glu Ala Val Ala Ser Ile Gln Lys Gly Leu Ile Glu Ala
    290                 295                 300
Lys Ala Ser Gly Thr Ala Val Ile Thr Val Glu Thr Glu Asp Gly Ser
305                 310                 315                 320
Leu Lys Ser Glu Ser Gln Ile Thr Val Thr Asp Ala Val Val Asp Glu
                325                 330                 335
Tyr Asp Gln Leu Arg Lys Lys Trp Lys Ser Leu Met Thr Gly Leu Asp
            340                 345                 350
Ser Tyr Asp Pro Thr Asn Val Arg Met Asn Glu Met Ile Gln Asn Gln
        355                 360                 365
Thr Lys Ser Ala Glu Thr Leu Trp Lys Thr Met Phe Lys Asn Asn Asp
370                 375                 380
Arg Ser Phe Leu Trp Ile Asn Phe Ala Ser Thr Asp Asn Ser Ala Asp
385                 390                 395                 400
Ile Arg Asp Ser Tyr Arg Asn Leu Thr Thr Met Ala Lys Ala Phe Ala
                405                 410                 415
Asn Glu His Ser Ser Leu Tyr Arg Asn Pro Gln Leu Leu Lys Asp Ile
            420                 425                 430
Thr Glu Ala Leu Glu Trp Leu Tyr Gln Asn Arg Tyr Asn Glu Ser Ile
        435                 440                 445
Ala Gln Tyr Ser Asn Trp Trp His Trp Glu Ile Gly Val Pro Asn Glu
450                 455                 460
Leu Asn Ser Leu Met Val Leu Leu Tyr Asp Tyr Leu Asp Gln Asp Ser
465                 470                 475                 480
Ile His Arg Tyr Leu Lys Val Val Asp His Phe Gln Pro Asp Pro Thr
                485                 490                 495
Lys Ser Gly Ala Thr Thr Pro Glu Lys Tyr Arg Glu Ala Leu Gly Ala
            500                 505                 510
Asn Arg Ile Asp Val Ser Lys Val Val Gly Val Arg Gly Val Ile Val
        515                 520                 525
Lys Asp Ala Thr Lys Ile Ala Ala Arg Asp Ala Leu Ser Gln Thr
530                 535                 540
Phe Glu Asn Val Thr Glu Gly Asp Gly Phe Tyr Glu Asp Gly Ser Phe
545                 550                 555                 560
Val Gln His Glu Asn Ile Ala Tyr Asn Gly Ser Tyr Gly Ile Val Leu
                565                 570                 575
Ile Glu Gly Leu Thr Asp Met Leu Glu Leu Leu Ser Asn Ser Thr Trp
            580                 585                 590
Gln Val Thr Asp Pro Lys Val Thr Asn Val Tyr Asp Trp Ile Glu Thr
        595                 600                 605
Ala Tyr Glu Pro Phe Met Tyr Lys Gly Ala Leu Met Asp Met Val Arg
610                 615                 620
Gly Arg Ala Ile Ser Arg Asn Phe Leu Gln Asp His Gln Ala Gly His
625                 630                 635                 640
Thr Ile Ile Lys Ser Val Ile Arg Met Ala Gln Phe Ala Pro Glu Pro
                645                 650                 655
Tyr Ala Glu Lys Tyr Asn Ser Met Ala Lys Tyr Trp Leu Gln Glu Asp
            660                 665                 670
Thr Tyr Leu Asp Tyr Phe Lys Asn Ala Gly Asn Phe Arg Asp Ile Thr
        675                 680                 685
Leu Ala Lys Gln Leu Leu Glu Lys Gln Glu Val Thr Pro Arg Gly Asp
690                 695                 700
```

-continued

```
Leu Asp Phe His Lys Thr Phe Ala Ser Met Asp Arg Val Val His Arg
705                 710                 715                 720

Lys Ser Gly Tyr Ala Phe Gly Ile Ser Met Tyr Ser Asn Arg Ile Gln
                725                 730                 735

Asn Tyr Glu Asp Met Asn Asp Glu Asn Arg Lys Gly Trp Tyr Thr Gly
            740                 745                 750

Glu Gly Met Thr Tyr Leu Tyr Asn Gly Asp Leu Ala Gln Tyr Ser Asp
        755                 760                 765

Asp Phe Trp Pro Thr Val Asp Pro Tyr Arg Met Pro Gly Thr Thr Val
    770                 775                 780

Asp Thr Met Arg Arg Ala Asp Gly Ser Gly Glu His Arg Ser Ser Glu
785                 790                 795                 800

Ser Trp Thr Gly Gly Ser Thr Leu Lys Asn Phe Gly Ser Ala Gly Met
                805                 810                 815

Ser Tyr Asp Ala Trp Asn Ser Ser Leu Ile Ala Lys Lys Ser Trp Phe
            820                 825                 830

Met Phe Asp Asn Glu Ile Val Ala Leu Gly Ala Gly Ile Thr Ser Ser
        835                 840                 845

Glu Asp Arg Asn Val Glu Ser Ile Val Glu Asn Arg Lys Ile Arg Asn
850                 855                 860

Asp Gly Ser Asn Gln Leu Val Ile Asn Gly Glu Thr Leu Asn Leu Ser
865                 870                 875                 880

Asn Gly Gly Gln Asn Gln Thr Met Ala Ala Lys Trp Ala Phe Leu Glu
                885                 890                 895

Gly Asn Val Pro Gly Ala Asp Ile Gly Tyr Tyr Phe Pro Glu Gly Lys
            900                 905                 910

Met Leu Thr Ile Lys Lys Glu Glu Arg Thr Gly Ala Trp Lys Asp Ile
        915                 920                 925

Asn Tyr Gly Gly Pro Ala Glu Ala Ile Lys Arg Ser Tyr Thr Thr Met
    930                 935                 940

Trp Phe Asp His Gly Val Arg Pro Glu Gln Asp Thr Tyr Ser Tyr Val
945                 950                 955                 960

Leu Leu Pro Gly Leu Asn Lys Glu Gln Thr His Gln Tyr Ser Gln Asn
                965                 970                 975

Pro Asp Ile Thr Ile Leu Arg Asn Asp Ser Ala Val Gln Ala Val Gln
            980                 985                 990

Asp Val Lys Glu Asn Ile Ile Gly Ala Asn Phe Trp Lys Asp Glu Lys
        995                 1000                1005

Gln Ser Ala Gly Pro Leu Thr Val Tyr Gln Lys Ala Ser Val Thr
    1010                1015                1020

Met Gln Glu Lys Asp Gly Val Leu Glu Ile Ala Val Cys Asp Pro
    1025                1030                1035

Thr Met Glu Asn Lys Gly Ser Ile Glu Ile Glu Ile Asp Gly Lys
    1040                1045                1050

Ala Phe Lys Val Leu Glu Ala Asp Glu Ser Ile Thr Val Glu Asn
    1055                1060                1065

Thr Lys Pro Ser Ile Lys Leu Lys Val Asn Val Asn Glu Ala Lys
    1070                1075                1080

Gly Lys Thr Phe Thr Ala Lys Leu Lys Met Ile Pro Ser Gln Lys
    1085                1090                1095

Gly Asn Ser Pro Asn Ser Ile Arg
    1100                1105
```

<210> SEQ ID NO 3
<211> LENGTH: 3324
<212> TYPE: DNA
<213> ORGANISM: Artificial Sequence
<220> FEATURE:
<223> OTHER INFORMATION: Synthetic polynucleotide

<400> SEQUENCE: 3

| | | | | | |
|---|---|---|---|---|---|
| aatgaatcta | ctttactatt | gaatactagt | tttgaagaga | cggaggcgcc | aaaatcaggc | 60 |
| tgggatcaat | taggtgcacc | aaaatggggt | gtctggagac | ctaccggaag | ccccattgta | 120 |
| accattacaa | aggaagcaag | ccgtacgggt | gagtatggtt | taaaaattgc | cgcggcgcaa | 180 |
| tctgctagag | ctgccgtgtc | acaggatgta | cctgttcagg | gcgggcagac | ctatcagtta | 240 |
| ggcacctggc | tgaagacaga | taatatcgtc | agcggtcaag | gggcgcggct | gagggttgtt | 300 |
| ttatatgaag | gaacccagca | gctgggctta | ctttactctt | caagattaac | tgggacccac | 360 |
| gattggtcgc | aaataaaaat | ggaggtaaag | actcctgcca | atgccgatag | catccgtgtc | 420 |
| cagcttttct | tgaaacagg  | aacgggtaca | gccctatttg | atgatgtttc | actgcagctc | 480 |
| atccagccag | ctacgtcgat | tgctatcgaa | gaaagtgaaa | tcaccatcaa | agagcaggaa | 540 |
| acaggtttat | tgcatgcaca | gatggttcct | gctgatgcca | gctccaaagt | atcttgggtg | 600 |
| tcggcggatc | catcgattgc | caccgttgat | aacggtaagg | ttacgggtgt | aaatcccggg | 660 |
| gggacaacga | ttatggcttt | taccgataac | gggcttgctg | ccactagtac | cgtaaaagtg | 720 |
| atcaaaaatg | atggtattga | acggccggag | gtaacacagt | tggatctaca | accaaaggaa | 780 |
| ctcgagcttg | gatcaggtca | agtgcgattg | cttcaggcaa | ttatcgcacc | agccactgcc | 840 |
| gatgcagaaa | agttggtatg | gagctcttcc | aatgaagcag | tcgcttctat | tcaaaaagga | 900 |
| cttattgaag | cgaaagcctc | aggaactgct | gtgattaccg | tagaaacgga | agatggcagc | 960 |
| ttaaagagtg | aaagccagat | taccgttacc | gatgcagtcg | tagatgaata | tgatcaactt | 1020 |
| cggaaaaagt | ggaaaagcct | gatgactggt | cttgattcgt | acgacccgac | gaatgtgcgg | 1080 |
| atgaacgaaa | tgattcagaa | ccagacaaaa | tcagcggaaa | ccctttggaa | aacaatgttt | 1140 |
| aaaaataacg | atcgttcgtt | cttatggatt | aactttgcaa | gcactgacaa | ttcggctgat | 1200 |
| attcgcgaca | gctaccggaa | tctaacgacc | atggctaaag | cgtttgccaa | tgaacactcc | 1260 |
| agcctttatc | gaaatccgca | attgctaaag | gatatcacgg | aggcgctaga | gtggctgtac | 1320 |
| caaaatcgct | ataacgaaag | tattgctcaa | tatagcaatt | ggtggcattg | ggaaatcggt | 1380 |
| gtcccgaatg | aattaaacag | tttaatggtt | cttctatatg | attatttgga | tcaagatagt | 1440 |
| attcatcgct | acttgaaagt | agtcgaccac | tttcaaccag | atccaacgaa | atccggagcc | 1500 |
| accactcccg | agaaataccg | ggaagctctt | ggcgccaatc | ggattgatgt | cagcaaggta | 1560 |
| gtcggtgtgc | gagggtaat  | tgtgaaggac | gccacgaaaa | ttgcggctgc | acgagatgcc | 1620 |
| ctaagccaaa | cttttgaaaa | cgtaactgaa | ggagacggtt | tttatgaaga | tggctccttc | 1680 |
| gttcagcatg | agaatatcgc | ctataacggg | tcatacggca | ttgtcttaat | tgaaggcttg | 1740 |
| actgacatgc | tcgaactctt | aagtaattct | acttggcaag | tgactgaccc | taaggttacc | 1800 |
| aatgtttatg | actggattga | aactgcctat | gaaccattta | tgtataaagg | tgctttgatg | 1860 |
| gatatggtga | gaggaagagc | gatttcacgt | aatttccttc | aggatcatca | ggctggacac | 1920 |
| accattatca | aaagtgtgat | tcgaatggca | caatttgctc | cagagccata | tgcagagaag | 1980 |
| tataattcca | tggcaaaata | ctggcttcaa | gaagatactt | acctggatta | ttttaaaaac | 2040 |
| gcgggtaact | tccgcgatat | cactcttgca | aagcagcttt | tggaaaaaca | agaggtcacc | 2100 |

```
cctcgcggag atcttgattt tcataagact ttcgcctcca tggaccgggt tgtccacaga    2160
aaatcgggct atgcgtttgg tatcagtatg tattcaaaca ggattcaaaa ttatgaagac    2220
atgaatgatg aaaaccgcaa aggctggtat accggagaag ggatgaccta cttatataat    2280
ggtgacctcg ctcaatatag tgatgatttc tggccgacag tggacccgta ccggatgcca    2340
gggacaacgg ttgatacgat gagacgagcg gatggaagtg gtgagcacag gtcgtcagag    2400
tcatggactg gcggttcaac cctaaagaat tttggttctg caggaatgtc ttatgatgct    2460
tggaatagtt cattgattgc caaaaagtca tggtttatgt tcgataacga aatcgttgcc    2520
cttggtgcag ggattactag cagtgaagac cggaatgttg agagtattgt cgaaaaccga    2580
aagattcgaa atgacggttc caatcaattg gtcatcaatg gtgaaacgct gaatttaagc    2640
aatggtggtc aaaaccaaac gatggccgct aaatgggctt ttcttgaagg gaatgtccca    2700
ggagcagata ttggttacta tttcccagaa ggtaaaatgc tgacgattaa aaaagaagaa    2760
cgtaccggtg catggaaaga tattaattat ggcggtccag ctgaagcgat caagcgatcc    2820
tacacaacga tgtggtttga ccatggtgtc cgtcctgagc aggatacgta ctcctatgtt    2880
ctattgccag gtttaaataa ggaacaaaca caccaatatt ctcaaaatcc tgatattacg    2940
attttacgaa atgattctgc tgtccaagcg gtacaagacg taaaggagaa tatcataggg    3000
gctaatttct ggaaggatga aaagcaaagt gctggtccgt taactgttta tcaaaaagcc    3060
tccgtgacca tgcaggagaa ggatggagtc cttgagattg ctgtatgtga tccgacgatg    3120
gaaaacaagg gttctatcga aatcgaaatt gatggcaagg cgttcaaggt tttagaagcc    3180
gatgaaagta tcacggtaga aaatacgaag ccgtcaatca agttgaaggt caatgtgaat    3240
gaggcaaaag ggaaaacgtt cacagcgaaa ttgaaaatga ttccgagcca aaagggcaat    3300
agcccgaact caatcagata ataa                                           3324

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
agagtttgat cctggctcag                                                  20

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
ggttaccttg ttacgactt                                                   19
```